US010089437B2

(12) United States Patent
Green, Jr. et al.

(10) Patent No.: US 10,089,437 B2
(45) Date of Patent: *Oct. 2, 2018

(54) METHODS FOR GENOME ASSEMBLY AND HAPLOTYPE PHASING

(71) Applicant: The Regents of the University of California, Oakland, CA (US)

(72) Inventors: Richard E. Green, Jr., Santa Cruz, CA (US); Liana F. Lareau, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 260 days.

This patent is subject to a terminal disclaimer.

(21) Appl. No.: 14/764,945

(22) PCT Filed: Jan. 31, 2014

(86) PCT No.: PCT/US2014/014184
§ 371 (c)(1),
(2) Date: Jul. 30, 2015

(87) PCT Pub. No.: WO2014/121091
PCT Pub. Date: Aug. 7, 2014

(65) Prior Publication Data
US 2015/0363550 A1   Dec. 17, 2015

Related U.S. Application Data

(60) Provisional application No. 61/759,941, filed on Feb. 1, 2013, provisional application No. 61/892,355, filed on Oct. 17, 2013.

(51) Int. Cl.
*C12Q 1/68* (2018.01)
*G06F 19/22* (2011.01)
*C12Q 1/6869* (2018.01)
*C40B 30/02* (2006.01)

(52) U.S. Cl.
CPC ........... *G06F 19/22* (2013.01); *C12Q 1/6869* (2013.01); *C40B 30/02* (2013.01)

(58) Field of Classification Search
None
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,988,617 A | 1/1991 | Landergren et al. |
| 5,143,854 A | 9/1992 | Pirrung et al. |
| 5,234,809 A | 8/1993 | Boom et al. |
| 5,242,794 A | 9/1993 | Whiteley et al. |
| 5,348,853 A | 9/1994 | Wang et al. |
| 5,476,930 A | 12/1995 | Letsinger et al. |
| 5,494,810 A | 2/1996 | Barany et al. |
| 5,567,583 A | 10/1996 | Wang et al. |
| 5,571,639 A | 11/1996 | Hubbell et al. |
| 5,593,839 A | 1/1997 | Hubbell et al. |
| 5,705,628 A | 1/1998 | Hawkins |
| 5,780,613 A | 7/1998 | Letsinger et al. |
| 5,786,146 A | 7/1998 | Herman et al. |
| 5,837,832 A | 11/1998 | Chee et al. |
| 5,989,823 A | 11/1999 | Jayasena et al. |
| 5,994,056 A | 11/1999 | Higuchi |
| 6,033,854 A | 3/2000 | Kurnit et al. |
| 6,110,709 A | 8/2000 | Aubel et al. |
| 6,117,635 A | 9/2000 | Nazarenko et al. |
| 6,171,785 B1 | 1/2001 | Higuchi |
| 6,174,670 B1 | 1/2001 | Wittwer et al. |
| 6,225,109 B1 | 5/2001 | Juncosa et al. |
| 6,287,766 B1 | 9/2001 | Nolan et al. |
| 6,326,145 B1 | 12/2001 | Whitcombe et al. |
| 6,416,950 B1 | 7/2002 | Lohse et al. |
| 6,449,562 B1 | 9/2002 | Chandler et al. |
| 6,582,938 B1 | 6/2003 | Su et al. |
| 6,787,308 B2 | 9/2004 | Balasubramanian et al. |
| 6,833,246 B2 | 12/2004 | Balasubramanian |
| 6,897,023 B2 | 5/2005 | Fu et al. |
| 6,969,488 B2 | 11/2005 | Bridgham et al. |
| 7,001,724 B1 | 2/2006 | Greenfield |
| 7,361,468 B2 | 4/2008 | Liu et al. |
| 7,414,117 B2 | 8/2008 | Saito et al. |

(Continued)

FOREIGN PATENT DOCUMENTS

| | | |
|---|---|---|
| EP | 476014 A1 | 3/1992 |
| EP | 717113 A2 | 6/1996 |

(Continued)

OTHER PUBLICATIONS

Schena et al., "Genes genomes and chips," DNA microarrays: A practical approach. 1999 : 1-15.
Schena et al. Parallel analysis with biological chips. PCR applications: protocols for functional genomics. 1999 : 445-456.
Schena M. (ed.), Microarray Biochip Technology (2000), ISBN-10: 1881299376 | ISBN-13: 978-1881299370.
Schwartz et al., "Separation of yeast chromosome-sized DNAs by pulsed field gradient gel electrophoresis," Cell, 1984, 37: 67-75.
Selvaraj, et al. Whole-genome haplotype reconstruction using proximity-ligation and shotgun sequencing. Nat. Biotechnol. 2013, 31: 1113-1119.
Sewards, Richard, Application No. GB1501001.0, Examination Report, United Kingdom Patent Office, dated May 6, 2015.

(Continued)

*Primary Examiner* — David C Thomas
(74) *Attorney, Agent, or Firm* — Joseph R. Baker, Jr.; Gavrilovich, Dodd & Lindsey LLP

(57) ABSTRACT

The disclosure provides methods to assemble genomes of eukaryotic or prokaryotic organisms. The disclosure further provides methods for haplotype phasing and meta-genomics assemblies.

18 Claims, 9 Drawing Sheets

(56) References Cited

U.S. PATENT DOCUMENTS

| | | |
|---|---|---|
| 7,425,415 B2 | 9/2008 | Pfeifer et al. |
| 7,709,179 B2 | 5/2010 | Iwashita |
| 7,709,197 B2 | 5/2010 | Drmanac et al. |
| 7,901,891 B2 | 3/2011 | Drmanac |
| 7,985,546 B2 | 7/2011 | Church et al. |
| 8,058,004 B2 | 11/2011 | Oleinikov |
| 8,071,296 B2 | 12/2011 | Ruan et al. |
| 8,076,070 B2 | 12/2011 | Chen et al. |
| 8,153,373 B2 | 4/2012 | De Laat et al. |
| 8,278,112 B2 | 10/2012 | Shokat et al. |
| 8,367,322 B2 | 5/2013 | Barany et al. |
| 8,642,295 B2 | 2/2014 | De Laat et al. |
| 8,673,562 B2 | 3/2014 | Drmanac et al. |
| 9,411,930 B2 * | 8/2016 | Green, Jr. ............ C12Q 1/6874 |
| 9,910,955 B2 * | 3/2018 | Green, Jr. ............ C12Q 1/6874 |
| 2002/0012930 A1 | 1/2002 | Rothberg et al. |
| 2002/0190663 A1 | 12/2002 | Rasmsen |
| 2003/0022207 A1 | 1/2003 | Balasubramanian et al. |
| 2003/0044781 A1 | 3/2003 | Korlach et al. |
| 2003/0064398 A1 | 4/2003 | Barnes |
| 2003/0068629 A1 | 4/2003 | Rothberg et al. |
| 2003/0100102 A1 | 5/2003 | Rothberg et al. |
| 2003/0148344 A1 | 8/2003 | Rothberg et al. |
| 2004/0106110 A1 | 6/2004 | Balasubramanian et al. |
| 2004/0248161 A1 | 12/2004 | Rothberg et al. |
| 2005/0079510 A1 | 4/2005 | Berka et al. |
| 2005/0100932 A1 | 5/2005 | Lapid et al. |
| 2005/0124022 A1 | 6/2005 | Srinivasan et al. |
| 2005/0130161 A1 | 6/2005 | Fraser et al. |
| 2006/0012784 A1 | 1/2006 | Ulmer |
| 2006/0012793 A1 | 1/2006 | Harris |
| 2006/0024678 A1 | 2/2006 | Buzby |
| 2006/0024711 A1 | 2/2006 | Lapid et al. |
| 2006/0078909 A1 | 4/2006 | Srinivasan et al. |
| 2006/0078937 A1 | 4/2006 | Korlach et al. |
| 2007/0172839 A1 | 7/2007 | Smith et al. |
| 2009/0111115 A1 | 4/2009 | Drmanac et al. |
| 2009/0233291 A1 | 9/2009 | Chen et al. |
| 2009/0298064 A1 | 12/2009 | Batzoglou et al. |
| 2010/0062947 A1 | 3/2010 | De Laat et al. |
| 2010/0093986 A1 | 4/2010 | Zwick et al. |
| 2010/0130373 A1 | 5/2010 | Dekker et al. |
| 2011/0033854 A1 | 2/2011 | Drmanac et al. |
| 2011/0287947 A1 | 11/2011 | Chen et al. |
| 2012/0197533 A1 | 8/2012 | Nazarenko et al. |
| 2012/0302449 A1 | 11/2012 | Dong et al. |
| 2013/0096009 A1 | 4/2013 | Dekker et al. |
| 2013/0183672 A1 | 7/2013 | De Laat et al. |
| 2013/0203605 A1 | 8/2013 | Shendure et al. |

FOREIGN PATENT DOCUMENTS

| | | |
|---|---|---|
| EP | 728520 A1 | 8/1996 |
| EP | 2624059 A1 | 8/2013 |
| GB | 2519255 A | 4/2015 |
| WO | 90/15070 A1 | 12/1990 |
| WO | 92/10092 A1 | 6/1992 |
| WO | 93/09668 A1 | 5/1993 |
| WO | 95/11995 A1 | 5/1995 |
| WO | 97/29212 A1 | 8/1997 |
| WO | 98/041651 A1 | 9/1998 |
| WO | 02/088382 A2 | 11/2002 |
| WO | 02/103046 A2 | 12/2002 |
| WO | 03/020968 A2 | 3/2003 |
| WO | 03/031947 A2 | 4/2003 |
| WO | 05/005655 A1 | 1/2005 |
| WO | 05/005657 A1 | 1/2005 |
| WO | 05/044836 A2 | 5/2005 |
| WO | 08/024473 A2 | 2/2008 |
| WO | 09/053039 A1 | 4/2009 |
| WO | 10/036323 A | 4/2010 |
| WO | 12/005595 A2 | 1/2012 |
| WO | 12/047726 A1 | 4/2012 |
| WO | 12/106546 A2 | 8/2012 |
| WO | 2012/106546 A2 | 8/2012 |
| WO | 12/142531 A2 | 10/2012 |
| WO | 12/142611 A2 | 10/2012 |
| WO | 2012/142531 A2 | 10/2012 |
| WO | 12/150317 A1 | 11/2012 |
| WO | 14/121091 A1 | 8/2014 |

OTHER PUBLICATIONS

Shalon et al., "A DNA microarray system for analyzing complex DNA samples using two-color fluorescent probe hybridization," Genome Research, 1996, 6: 639-645.

Simpson, et al., "Efficient de novo assembly of large genomes using compressed data structures," Genome Res., Mar. 2012, 22(3): 549-556.

Solomon et al., "Mapping protein-DNA interactions in vivo with formaldehyde: evidence that histone H4 is retained on a highly transcribed gene," Cell, 1988, 53(6):937-947.

Solomon et al., "Formaldehyde-mediated DNA-protein crosslinking: a probe for in vivo chromatin structures." Proceedings of the National Academy of Sciences, 1985, 82: 6470-6474.

Soni, et al., "Progress toward ultrafast DNA sequencing using solid-state nanopores," Clin Chem., Nov. 2007, 53: 1996-2001. Epub Sep. 21, 2007.

Splinter, E. 3C Technology: Analyzing the Spatial Organization of Genomic Loci In Vivo Methods in Enzymology, vol. 375, pp. 493-507 (2004).

Syed, Fraz et al. Optimized library preparation method for next-generation sequencing. Nature Methods Oct. 2009, pp. i-ii.

Tanizawa, et al. "Mapping of long-range associations throughout the fission yeast genome reveals global genome organization linked to transcriptional regulation," Nucleic Acids Research, 2010, 38: 8164-8177.

Teague, et al. "High-resolution human genome structure by single-molecule analysis." Proceedings of the National Academy of Sciences. 2010, 107(24): 10848-10853.

Tyagi, et al., "Molecular beacons: probes that fluoresce upon hybridization," Nature biotechnology, 1996, 14: 303-308.

Venter, et al., "The sequence of the human genome," Science, Feb. 16, 2001, 291:1304-51.

Whitcombe, et al., "Detection of PCR Products Using Self-probing Amplicons and Fluorescence," Nature Biotechnology,1999, 17:804-807.

Wing, et al., "An improved method of plant megabase DNA isolation in agarose microbeads suitable for physical mapping and YAC cloning," The Plant Journal, 1993, 4(5): 893-898.

Zhou, et al., "A single molecule scaffold for the maize genome," PLoS Genetics, 2009, 5(11): e1000711.

Adams et al., "The Genome Sequence of *Drosophila melanogaster*," Science, Mar. 24, 2000, 287.5461: 2185-2195.

Allison, Lizabeth, 2007, Fundamental Molecular Biology. Wiley-Blackwell, Chapter 8.

Ausubel, et al., eds. 1993. Current Protocols in Molecular Biology. Part 1: *E. coli*, plasmids, and bacteriophages.

Bansal et al., "Hapcut: an efficient and accurate algorithm for the haplotype assembly problem," Bioinformatics, 2006, 24(16): i153-i159.

Burton, Joshua et al. Chromosome-scale scaffolding of de novo genome assemblies based on chromatin interactions. Nature Biotechnology. 2013, 31: 1119-1125.

Cai et al., "SATB1 packages densely looped transcriptionally active chromatin for coordinated expression of cytokine genes," Nature Genetics, 2006, 38.11: 1278-1288.

Chapman et al., "Meraculo: de novo genome assembly with short paired-end reads," PLoS one, 2011, 6.8: e23501.

Constans A., "Microarrays in Microtubes," Scientist. 2003 17.13: 36.

Copenheaver, Blaine R., Search Report and Written Opinion issued in PCT/US2014/014184, United States Patent and Trademark Office, dated Apr. 23, 2014.

Cortese J., "Array of options," Scientist, 2000 14.11: 26.

Cortese J., "The array of today," Scientist, 2000 14.17: 25.

(56) References Cited

OTHER PUBLICATIONS

Dekker et al., A Closer look at long-range chromosomal interactions (2003) Trends in Biochemical Science 28:277-280.
Dekker et al., "Capturing chromosome conformation," Science, 2002, 295:1306-1311.
Dostie et al., "Chromosome Conformation Capture Carbon Copy (5C): a massively parallel solution for mapping interactions between genomic elements," Genome research, 2006, 16.10: 1299-1309.
Dower, et al. Recombinant and synthetic randomized peptide libraries. Ann. Rep. Med. Chem. 1991, 26:271-280.
Drmanac et al., "Human Genome Sequencing Unchained Base Reads on Self-Assembling DNA Nanoarrays," Science, Jan. 1, 2010, 327.5961: 78-81.
Ekins et al., "Microarrays: their origins and applications," Trends in Biotechnology, 1999, 17: 217-218.
Fan et al. "A versatile assay for high-throughput gene expression profiling on universal array matrices." Genome Research, 2004, 14.5: 878-885.
Fangman et al., "Activation of replication origins within yeast chromosomes," Annual Review of Cell Biology, 1991 7.1: 375-402.
Fodor et al., "Light-directed spatially addressable parallel chemical synthesis," Science, Feb. 15, 1991, 251.4995: 767-773.
Fullwood, MJ. Et al. Chromatin interaction analysis using paired-end tag sequencing. Jan. 2010 Curr. Prot. In Mol. Biol. Chapter 21; unit 21 .15.1-25. doi: 10.1002/0471142727.mb2115s89.
Fyodorov et al., "Chromatin assembly in vitro with purified recombinant ACF and NAP-1," Methods in Enzymology, 2002, 371: 499-515.
Garaj et al., "Graphene as a sub-nanometer trans-electrode membrane," Nature, Sep. 9, 2010, 467(7312): 190-193.
Gilmour et al., "Detecting protein-DNA interactions in vivo: distribution of RNA polymerase on specific bacterial genes." Proceedings of the National Academy of Sciences, 1984, 81:4275-4279.
Grunenwald et al., "Rapid, high-throughput library preparation for next-generation sequencing" 2010 Nature Methods, vol. 7.
Gwynne et al., "Microarray analysis: the next revolution in molecular biology," Science, Aug. 6, 1999.
Heid et al., "Real time quantitative PCR," Genome Research, 1996: 6(10): 986-994.
Herschleb et al., "Pulsed-field gel electrophoresis," Nat Protoc., 2007, 2(3): 677-84.
Kalhor et al., "Genome architectures revealed by tethered chromosome conformation capture and population-based modeling," Nature Biotechnology, 2012, 30(1): 90-98.
Kaplan, et al. High-throughput genome scaffolding from in vivo DNA interaction Frequency. Nat. Biotechnol. vol. 31 pp. 1139-1143 (2013).
Kitzman et al., "Haplotype-resolved genome sequencing of a Gujarati Indian individual," Nature Biotechnology, 2011, 29(1): 59-63.
Kotoulas, et al. The chipping forecast. Special supplement to Nature Genetics vol. 21 (1999).
Kundu et al., "Activator-dependent transcription from chromatin in vitro involving targeted histone acetylation by p300," Molecular Cell, 2000, 6(3): 551-561.
Lasken et al., "Mechanism of chimera formation during the Multiple Displacement Amplification reaction," BMC Biotechnology, 2007, 7(1): 19.
Lemieux et al., "Overview of DNA chip technology," Molecular Breeding, 1998, 4(4): 277-289.

Levene et al., "Zero-Mode Waveguides for Single-Molecule Analysis at High Concentrations," Science, Jan. 31, 2003, 299: 682-686.
Lieberman-Aiden et al. "Comprehensive mapping of long range interactions reveals folding principles of the human genome." Science, Oct. 9, 2009; 326:289-293.
Lupski et al., "Whole-genome sequencing in a patient with Charcot-Marie-Tooth neuropathy," New England Journal of Medicine, 2010, 362:1181-1191.
Lusser et al., "Strategies for the reconstitution of chromatin." Nature Methods. 2004 1(1): 19-26.
Ma et al., "Application of Real-time Polymerase Chain Reaction (RT-PCR)", The Journal of American Science, 2006, 2(3):1-15.
Maniatis et al., Molecular Cloning: A Laboratory Manual Cold Spring Harbor N.Y. pp. 280-281 (1982).
Margulies et al., Genome Sequencing in Open Microfabricated High Density Picoliter Reactors, Nature, Sep. 15, 2005; 437(7057): 376-380.
Marshall et al., "DNA chips: an array of possibilities.," Nat Biotechnol. ,Jan. 1998, 16:27-31.
Miller et al. A Simple salting out procedure for extracting DNA from human nucleated cells. Nucleic Acids Research vol. 16, No. 3, 1215 (1988).
Myers, E.W. A Whole-genome assembly of *Drosophila*. Science 287 (5461), 2196-204, Mar. 24, 2000.
Nazarenko et al., "A closed tube format for amplification and detection of DNA based on energy transfer," Nucleic acids research, 1997 25(12): 2516-2521.
Peng et al., "Generation of long insert pairs using a Cre-LoxP Inverse PCR approach," PLoS One, 2012, 7(1): e29437.
Peters et al., "Accurate whole-genome sequencing and haplotyping from 10 to 20 human cells", Nature, Jul. 12, 2012, vol. 487, pp. 190-195.
Rios et al., "Identification by whole-genome resequencing of gene defect responsible for severe hypercholesterolemia," Human Molecular Genetics., 2010, 19(22): 4313-4318.
Sambrook et al., "Mixed Oligonucleotide-primed Amplification of cDNA (MOPAC)," Cold Spring Harbor Protocols, 2006.
Becamel, Philippe, International Preliminary Report on Patentability and Written Opinion, PCT/US2014/014184, The International Bureau of WIPO, dated Aug. 13, 2015.
Barz, Wolfgang, Extended European Search Report, Application No. 14745949.9, European Patent Office, dated Nov. 21, 2016.
Peters et al., "Accurate whole-genome sequencing and haplotyping from 10 to 20 human cells", Nature, vol. 487, No. 7406, Jul. 11, 2012, pp. 190-195.
Mary, Isabelle et al., "Metaproteomic and metagenomic analyses of defined oceanic microbial populations using microwave cell fixation and flow cytometric sorting", FEMS Microbiol. Ecol., 74, 2010, pp. 10-18.
Sewards, Richard, Combined Search and Examination Report under Sections 17 & 18(3), Great Britain Patent Application No. GB1520448. 0, dated May 31, 2016.
Umbarger, M.A., "Chromosome conformation capture assays in bacteria", Methods, 58, 2012, pp. 212-220.
Fuji, Miho, Office Action, Japanese Patent Office, Application No. 2015-556175, dated Jan. 16, 2018.
Jansen et al., "Nucleosome Positioning in *Saccharomyces cerevisiae*", Microbiology and Molecular Biology Reviews, Jun. 2011, pp. 301-320.

\* cited by examiner

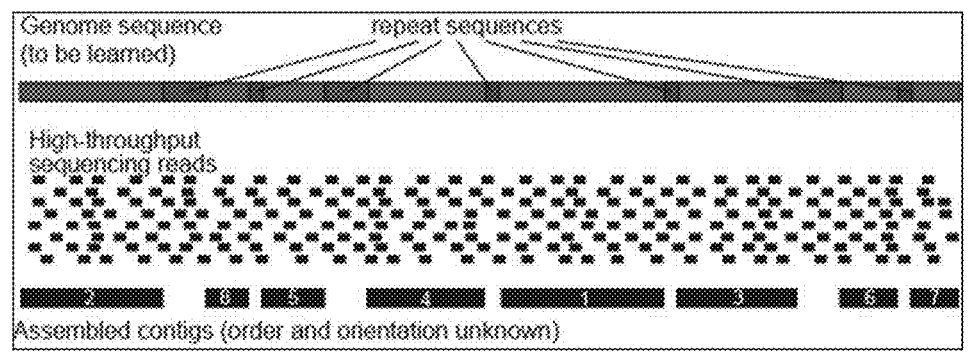
FIGURE 1
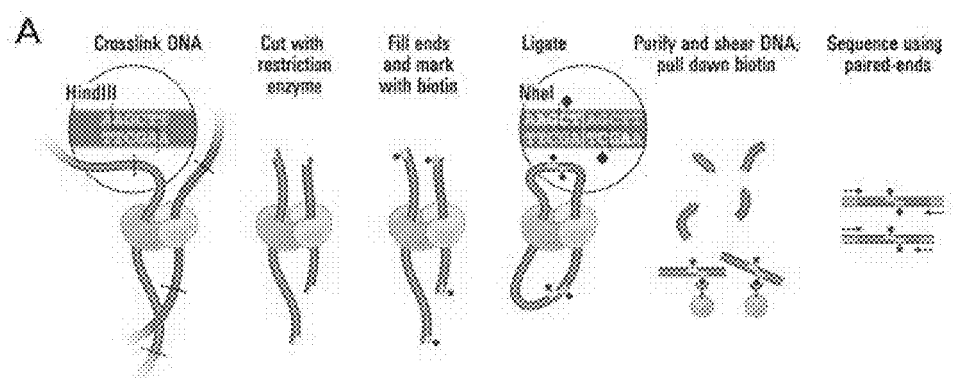
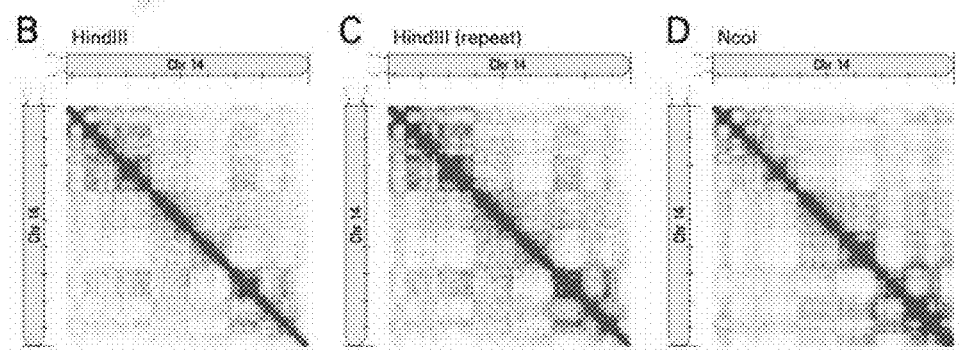
FIGURE 2A-D

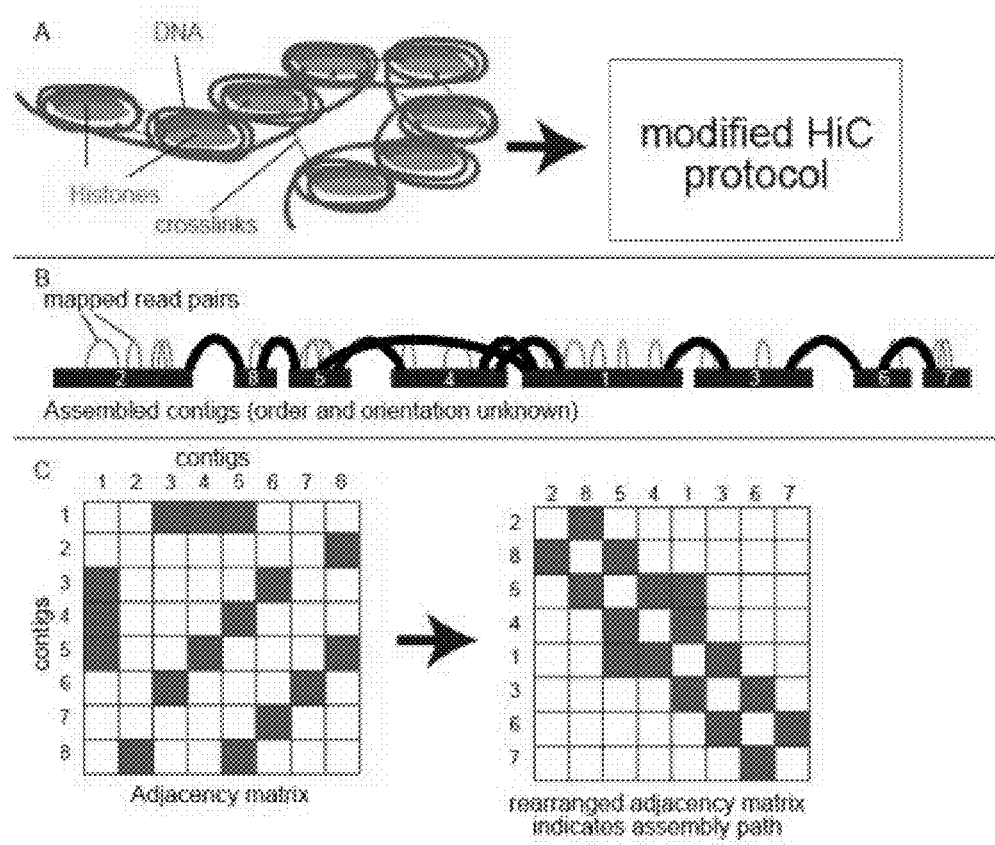
FIGURE 3A-C

FIGURE 5A-B

METHODS FOR GENOME ASSEMBLY AND HAPLOTYPE PHASING

CROSS REFERENCE TO RELATED APPLICATIONS

This application is a U.S. National Stage Application filed under 35 U.S.C. § 371 and claims the benefit of International Application No. PCT/US2014/014184, filed Jan. 31, 2014, which claims the benefit of Provisional Application Ser. No. 61/759,941, filed Feb. 1, 2013, and from Provisional Application Ser. No. 61/892,355 filed Oct. 17, 2013, the disclosures of which are incorporated herein by reference.

TECHNICAL FIELD

The disclosure provides for methods of genome assembly and haplotype phasing for identifying short, intermediate and long term connections within a genome.

BACKGROUND

It remains difficult in theory and in practice to produce high-quality, highly contiguous genome sequences.

SUMMARY

A persistent shortcoming of next generation sequencing (NGS) data is the inability to span large repetitive regions of genomes due to short read lengths and relatively small insert sizes. This deficiency significantly affects de novo assembly. Contigs separated by long repetitive regions cannot be linked or re-sequenced, since the nature and placement of genomic rearrangements are uncertain. Further, since variants cannot be confidently associated with haplotypes over long-distances, phasing information is indeterminable. The disclosure can address all of these problems simultaneously by generating extremely long-range read pairs (XLRPs) that span genomic distances on the order of hundreds of kilobases, and up to megabases with the appropriate input DNA. Such data can be invaluable for overcoming the substantial barriers presented by large repetitive regions in genomes, including centromeres; enable cost-effective de novo assembly; and produce re-sequencing data of sufficient integrity and accuracy for personalized medicine.

Of significant importance is the use of reconstituted chromatin in forming associations among very distant, but molecularly-linked, segments of DNA. The disclosure enables distant segments to be brought together and covalently linked by chromatin conformation, thereby physically connecting previously distant portions of the DNA molecule. Subsequent processing can allow for the sequence of the associated segments to be ascertained, yielding read pairs whose separation on the genome extends up to the full length of the input DNA molecules. Since the read pairs are derived from the same molecule, these pairs also contain phase information.

In some embodiments, the disclosure provides methods that can produce high quality assemblies with far less data than previously required. For example, the methods disclosed herein provide for genomic assembly from only two lanes of Illumina HiSeq data.

In other embodiments, the disclosure provides methods that can generate chromosome-level phasing using a long-distance read pair approach. For example, the methods disclosed herein can phase 90% or more of the heterozygous single nucleotide polymorphisms (SNPs) for that individual to an accuracy of at least 99% or greater. This accuracy is on par with phasing produced by substantially more costly and laborious methods.

In some examples, methods that can produce fragments of genomic DNA up to megabase scale can be used with the methods disclosed herein. Long DNA fragments can be generated to confirm the ability of the present methods to generate read pairs spanning the longest fragments offered by those extractions. In some cases, DNA fragments beyond 150 kbp in length can be extracted and used to generate XLRP libraries.

The disclosure provides methods for greatly accelerating and improving de novo genome assembly. The methods disclosed herein utilize methods for data analysis that allow for rapid and inexpensive de novo assembly of genomes from one or more subjects. The disclosure further provides that the methods disclosed herein can be used in a variety of applications, including haplotype phasing, and metagenomics analysis.

In certain embodiments, the disclosure provides for a method for genome assembly comprising the steps of: generating a plurality of contigs; generating a plurality of read pairs from data produced by probing the physical layout of chromosomes, chromatin, or reconstituted chromatin; mapping or assembling the plurality of read pairs to the plurality of contigs; constructing an adjacency matrix of contigs using the read-mapping or assembly data; and analyzing the adjacency matrix to determine a path through the contigs that represent their order and/or orientation to the genome. In further embodiments, the disclosure provides that at least about 90% of the read pairs are weighted by taking a function of each read's distance to the edge of the contig so as to incorporate information about which read pairs indicate short-range contacts and which read pairs indicate longer-range contacts. In other embodiments, the adjacency matrix can be re-scaled to down-weight the high number of contacts on some contigs that represent promiscuous regions of the genome, such as conserved binding sites for one or more agents that regulate the scaffolding interactions of chromatin, like transcriptional repressor CTCF. In other embodiments, the disclosure provides for a method for the genome assembly of a human subject, whereby the plurality of contigs is generated from the human subject's DNA, and whereby the plurality of read pairs is generated from analyzing the human subject's chromosomes, chromatin, or reconstituted chromatin made from the subject's naked DNA.

In further embodiments, the disclosure provides that a plurality of contigs can be generated by using a shotgun sequencing method comprising: fragmenting long stretches of a subject's DNA into random fragments of indeterminate size; sequencing the fragments using high throughput sequencing methods to generate a plurality of sequencing reads; and assembling the sequencing reads so as to form a plurality of contigs.

In certain embodiments, the disclosure provides that a plurality of read pairs can be generated by probing the physical layout of chromosomes, chromatin, or reconstituted chromatin using a Hi-C based technique. In further embodiments, the Hi-C based technique comprises, crosslinking chromosomes, chromatin, or reconstituted chromatin with a fixative agent, such as formaldehyde, to form DNA-protein cross links; cutting the cross-linked DNA-Protein with one or more restriction enzymes so as to generate a plurality of DNA-protein complexes comprising sticky ends; filling in the sticky ends with nucleotides containing one or more markers, such as biotin, to create blunt ends that are then ligated together; fragmenting the plurality of DNA-protein complexes into fragments; pulling down junction containing fragments by using the one or more of the markers; and sequencing the junction containing fragments using high throughput sequencing methods to generate a plurality of read pairs. In further embodiments, the plurality of read pairs for the methods disclosed herein is generated from data produced by probing the physical layout of reconstituted chromatin.

In various embodiments, the disclosure provides that a plurality of read pairs can be determined by probing the physical layout of chromosomes or chromatin isolated from cultured cells or primary tissue. In other embodiments, the plurality of read pairs can be determined by probing the physical layout of reconstituted chromatin formed by complexing naked DNA obtained from a sample of one or more subjects with isolated histones.

In other embodiments, the disclosure provides a method to determine haplotype phasing comprising a step of identifying one or more sites of heterozygosity in the plurality of read pairs, wherein phasing data for allelic variants can be determined by identifying read pairs that comprise a pair of heterozygous sites.

In various embodiments, the disclosure provides a method for high-throughput bacterial genome assembly, comprising a step of generating a plurality of read pairs by probing the physical layout of a plurality of microbial chromosomes using a modified Hi-C based method, comprising the modified steps of: collecting microbes from an environment; adding a fixative agent, such as formaldehyde, so as to form cross-links within each microbial cell, and wherein read pairs mapping to different contigs indicate which contigs are from the same species.

In some embodiments, the disclosure provides a method for genome assembly comprising: (a) generating a plurality of contigs; (b) determining a plurality of read pairs from data generated by probing the physical layout of chromosomes, chromatin, or reconstituted chromatin; (c) mapping the plurality of read pairs to the plurality of contigs; (d) constructing an adjacency matrix of contigs using the read-mapping data; and (e) analyzing the adjacency matrix to determine a path through the contigs that represent their order and/or orientation to the genome.

In further embodiments, the disclosure provides a method to generate a plurality of read pairs by probing the physical layout of chromosomes, chromatin, or reconstituted chromatin using a Hi-C based technique. In further embodiments, the Hi-C based technique comprises (a) crosslinking chromosomes, chromatin, or reconstituted chromatin with a fixative agent to form DNA-protein cross links; (b) cutting the crosslinked DNA-Protein with one or more restriction enzymes so as to generate a plurality of DNA-protein complexes comprising sticky ends; (c) filling in the sticky ends with nucleotides containing one or more markers to create blunt ends that are then ligated together; (d) shearing the plurality of DNA-protein complexes into fragments; (e) pulling down junction containing fragments by using one or more of the markers; and (f) sequencing the junction containing fragments using high throughput sequencing methods to generate a plurality of read pairs.

In certain embodiments, the plurality of read pairs is determined by probing the physical layout of chromosomes or chromatin isolated from cultured cells or primary tissue. In other embodiments, the plurality of read pairs is determined by probing the physical layout of reconstituted chromatin formed by complexing naked DNA obtained from a sample of one or more subjects with isolated histones.

In some embodiments, at least about 50%, about 60%, about 70%, about 80%, about 90%, about 95% or about 99% or more of the plurality of read pairs are weighted by taking a function of the read's distance to the edge of the contig so as to incorporate a higher probability of shorter contacts than longer contacts. In some embodiments, the adjacency matrix is re-scaled to down-weight the high number of contacts on some contigs that represent promiscuous regions of the genome.

In certain embodiments, the promiscuous regions of the genome include one or more conserved binding sites for one or more agents that regulate the scaffolding interactions of chromatin. In some examples, the agent is transcriptional repressor CTCF.

In some embodiments, the methods disclosed herein provide for the genome assembly of a human subject, whereby the plurality of contigs is generated from the human subject's DNA, and whereby the plurality of read pairs is generated from analyzing the human subject's chromosomes, chromatin, or reconstituted chromatin made from the subject's naked DNA.

In other embodiments, the disclosure provides a method for determining haplotype phasing, comprising identifying one or more sites of heterozygosity in the plurality of read pairs, wherein phasing data for allelic variants can be determined by identifying read pairs that comprise a pair of heterozygous sites.

In yet other embodiments, the disclosure provides a method for meta-genomics assemblies, wherein the plurality of read pairs is generated by probing the physical layout of a plurality of microbial chromosomes using a modified Hi-C based method, comprising: collecting microbes from an environment; and adding a fixative agent so as to form cross-links within each microbial cell, and wherein read pairs mapping to different contigs indicate which contigs are from the same species. In some examples, the fixative agent is formaldehyde.

In some embodiments, the disclosure provides a method of assembling a plurality of contigs originating from a single DNA molecule, comprising generating a plurality of read-pairs from the single DNA molecule and assembling the contigs using the read-pairs, wherein at least 1% of the read-pairs span a distance greater than 50 kB on the single DNA molecule and the read-pairs are generated within 14 days. In some embodiments, at least 10% of the read-pairs span a distance greater than 50 kB on the single DNA molecule. In other embodiments, at least 1% of the read-pairs span a distance greater than 100 kB on the single DNA molecule. In further embodiments, the read-pairs are generated within 7 days.

In other embodiments, the disclosure provides a method of assembling a plurality of contigs originating from a single DNA molecule, comprising generating a plurality of read-pairs from the single DNA molecule in vitro and assembling the contigs using the read-pairs, wherein at least 1% of the read-pairs span a distance greater than 30 kB on the single DNA molecule. In some embodiments, at least 10% of the read-pairs span a distance greater than 30 kB on the single DNA molecule. In other embodiments, at least 1% of the read-pairs span a distance greater than 50 kB on the single DNA molecule.

In yet other embodiments, the disclosure provides a method of haplotype phasing, comprising generating a plurality of read-pairs from a single DNA molecule and assembling a plurality of contigs of the DNA molecule using the read-pairs, wherein at least 1% of the read-pairs spans a distance greater than 50 kB on the single DNA molecule and the haplotype phasing is performed at greater than 70% accuracy. In some embodiments, at least 10% of the read-pairs span a distance greater than 50 kB on the single DNA molecule. In other embodiments, at least 1% of the read-pairs span a distance greater than 100 kB on the single DNA molecule. In further embodiments, the haplotype phasing is performed at greater than 90% accuracy.

In further embodiments, the disclosure provides a method of haplotype phasing, comprising generating a plurality of read-pairs from a single DNA molecule in vitro and assembling a plurality of contigs of the DNA molecule using the read-pairs, wherein at least 1% of the read-pairs spans a distance greater than 30 kB on the single DNA molecule and the haplotype phasing is performed at greater than 70% accuracy. In some embodiments, at least 10% of the read-pairs span a distance greater than 30 kB on the single DNA molecule. In other embodiments, at least 1% of the read-pairs span a distance greater than 50 kB on the single DNA molecule. In yet other embodiments, the haplotype phasing is performed at greater than 90% accuracy. In further embodiments, the haplotype phasing is performed at greater than 70% accuracy.

In some embodiments, the disclosure provides a method of generating a first read-pair from a first DNA molecule, comprising: (a) crosslinking the first DNA molecule in vitro, wherein the first DNA molecule comprises a first DNA segment and a second DNA segment; (b) linking the first DNA segment with the second DNA segment and thereby forming a linked DNA segment; and (c) sequencing the linked DNA segment and thereby obtaining the first read-pair.

In some embodiments, a plurality of association molecules, such as from reconstituted chromatin, are cross-linked to the first DNA molecule. In some examples, the association molecules comprise amino acids. In further examples, the association molecules are peptides or proteins. In certain embodiments, the first DNA molecule is cross-linked with a fixative agent. In some examples, the fixative agent is formaldehyde. In some embodiments, the first DNA segment and the second DNA segment are generated by severing the first DNA molecule. In certain embodiments, the method further comprises assembling a plurality of contigs of the first DNA molecule using the first read-pair. In some embodiments, each of the first and the second DNA segment is connected to at least one affinity label and the linked DNA segment is captured using the affinity label.

In further embodiments, the method further comprises: (a) providing a plurality of association molecules, such as from reconstituted chromatin, to at least a second DNA molecule; (b) crosslinking the association molecules to the second DNA molecule and thereby forming a second complex in vitro; (c) severing the second complex thereby generating a third DNA segment and a fourth segment; (d) linking the third DNA segment with the fourth DNA segment and thereby forming a second linked DNA segment; and (e) sequencing the second linked DNA segment and thereby obtaining a second read-pair. In some examples, less than 40% of the DNA segments from the DNA molecules are linked with DNA segments from any other DNA molecule. In further examples, less than 20% of the DNA segments from the DNA molecules are linked with DNA segments from any other DNA molecule.

In other embodiments, the disclosure provides a method of generating a first read-pair from a first DNA molecule comprising a predetermined sequence, comprising: (a) providing one or more DNA-binding molecules to the first DNA molecule, wherein the one or more DNA-binding molecules bind to the predetermined sequence; (b) cross-linking the first DNA molecule in vitro, wherein the first DNA molecule comprises a first DNA segment and a second DNA segment; (c) linking the first DNA segment with the second DNA segment and thereby forming a first linked DNA segment; and (d) sequencing the first linked DNA segment and thereby obtaining the first read-pair; wherein the probability that the predetermined sequence appears in the read-pair is affected by the binding of the DNA-binding molecule to the predetermined sequence.

In some embodiments, the DNA-binding molecule is a nucleic acid that can hybridize to the predetermined sequence. In some examples the nucleic acid is RNA. In other examples, the nucleic acid is DNA. In other embodiments, the DNA-binding molecule is a small molecule. In some examples, the small molecule binds to the predetermined sequence with a binding affinity less than 100 µM. In further examples, the small molecule binds to the predetermined sequence with a binding affinity less than 1 µM. In further embodiments, the DNA-binding molecule is immobilized on a surface or a solid support.

In some embodiments, the probability that the predetermined sequence appears in the read-pair is decreased. In other embodiments, the probability that the predetermined sequence appears in the read-pair is increased.

In yet other embodiments, the disclosure provides an in vitro library comprising a plurality of read-pairs each comprising at least a first sequence element and a second sequence element, wherein the first and the second sequence elements originate from a single DNA molecule and wherein at least 1% of the read-pairs comprise first and second sequence elements that are at least 50 kB apart on the single DNA molecule.

In some embodiments, at least 10% of the read-pairs comprise first and second sequence elements that are at least 50 kB apart on the single DNA molecule. In other embodiments, at least 1% of the read-pairs comprise first and second sequence elements that are at least 100 kB apart on the single DNA molecule.

In further embodiments, less than 20% of the read-pairs comprise one or more predetermined sequences. In further embodiments, less than 10% of the read-pairs comprise one or more predetermined sequences. In yet further embodiments, less than 5% of the read-pairs comprise one or more predetermined sequences.

In some embodiments, the predetermined sequences are determined by one or more nucleic acids that can hybridize to the predetermined sequences. In some examples, the one or more nucleic acids is RNA. In other examples, the one or more nucleic acids is DNA. In further examples, the one or more nucleic acids is immobilized to a surface or a solid support.

In other embodiments, the predetermined sequences are determined by one or more small molecule. In some examples, the one or more small molecule binds to the predetermined sequences with a binding affinity less than 100 µM. In further examples, the one or more small molecule binds to the predetermined sequences with a binding affinity less than 1 µM.

In some embodiments, the disclosure provides a composition comprising a DNA fragment and a plurality of association molecules, such as from reconstituted chromatin, wherein: (a) the association molecules are cross-linked to the DNA fragment in an in vitro complex; and (b) the in vitro complex is immobilized on a solid support.

In other embodiments, the disclosure provides a composition comprising a DNA fragment, a plurality of association molecules, and a DNA-binding molecule, wherein: (a) the DNA-binding molecule is bound to a predetermined sequence of the DNA fragment; and (b) the association molecules are cross-linked to the DNA fragment.

In some embodiments, the DNA-binding molecule is a nucleic acid that can hybridize to the predetermined sequence. In some examples, the nucleic acid is RNA. In other examples, the nucleic acid is DNA. In further examples, the nucleic acid is immobilized to a surface or a solid support.

In other embodiments, the DNA-binding molecule is a small molecule. In some examples, the small molecule binds to the predetermined sequence with a binding affinity less than 100 µM. In other examples, the small molecule binds to the predetermined sequence with a binding affinity less than 1 µM.

INCORPORATION BY REFERENCE

All publications, patents, and patent applications mentioned in this specification are herein incorporated by reference to the same extent as if each individual publication, patent, or patent application was specifically and individually indicated to be incorporated by reference. All publications, patents, and patent applications mentioned in this specification are herein incorporated by reference in its entirety as well as any references cited therein.

BRIEF DESCRIPTION OF THE DRAWINGS

The novel features of the disclosure are set forth with particularity in the appended claims. A better understanding of the features and advantages of the disclosure will be obtained by reference to the following detailed description that sets forth illustrative embodiments, in which the principles of the disclosure are utilized, and the accompanying drawings of which:

FIG. 1 presents an illustration of genome assembly using high-throughput sequencing reads. The genome to be assembled is shown (top). Typically, genomes have many repeat sequences that are difficult to assemble. Random, high-throughput sequence data from genomes (middle) are collected and assembled into "contigs" in regions that are unique in the genome (bottom). Contig assembly generally stops at the many repeat sequences. The final output is a set of thousands of contigs whose order and orientation relative to one another are not known. In the figure, they are arbitrarily numbered from longest to shortest.

FIG. 2A-D illustrates a Hi-C based protocol of the disclosure: (A) demonstrates where DNA is cross-linked and processed to created biotinylated junction fragments for sequencing; and (B-D) provide contact map data on human chr14 for a variety of restriction enzymes. As shown, most contacts are local along the chromosome.

FIG. 3A-C provides a method of the disclosure using Hi-C sequence data to assist genome assembly: (A) illustrates where DNA is cross-linked and processed using a Hi-C based protocol; (B) demonstrates where read-pair data is mapped to assembled contigs, generated from random shotgun sequencing and assembly; and (C) illustrates that after filtering and weighting, an adjacency matrix summarizing all inter-contig read pair data can be constructed. This matrix can be re-ordered to indicate the correct assembly path. As shown, most of the read pairs will map within a contig. From which, it is possible to learn the distribution of contact distances (e.g., see FIG. 6). Read pairs that map to different contigs provide data about which contigs are adjacent in a correct genome assembly.

DETAILED DESCRIPTION

Figure 4:
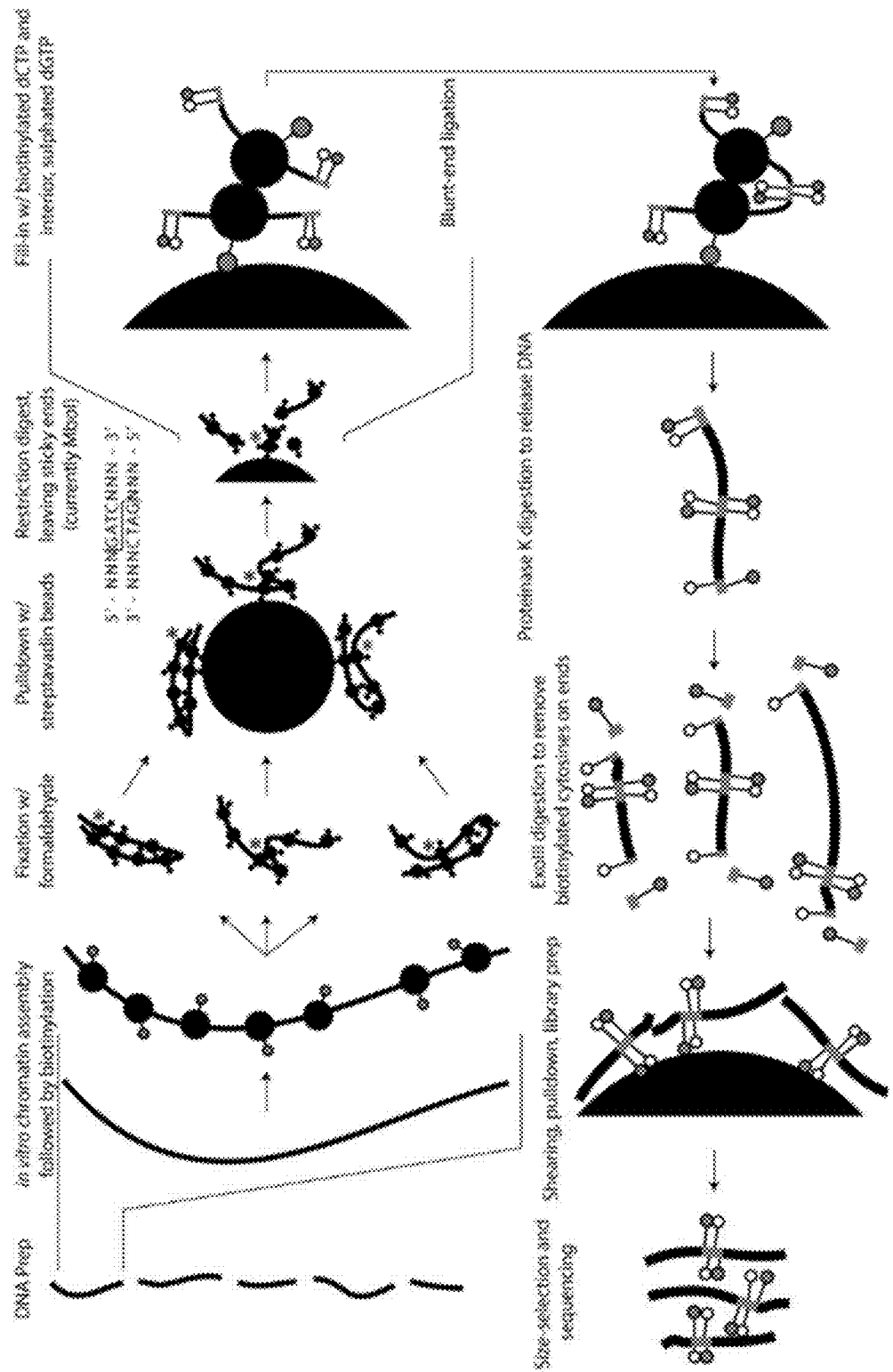
FIG. 4 illustrates an exemplary protocol of the disclosure: DNA fragments are first generated and prepared; followed by in vitro chromatin assembly and biotinylation; the chromatin/DNA complex is then fixed with formaldehyde and pulled down with streptavadin beads; the complexes are then restriction digested to generate sticky ends that are then filled with biotinylated dCTP and interior, sulfated GTP; following blunt-end ligation, the chromatin/DNA complex undergoes proteinase digestion, exonuclease digestion and shearing; after which the DNA fragments are pulled pulled-down with biotin and ligated with a sequencing adaptor; and finally, the DNA fragments are selected by size and sequenced.

As used herein and in the appended claims, the singular forms "a," "and," and "the" include plural referents unless the context clearly dictates otherwise. Thus, for example, reference to "contig" includes a plurality of such contigs and reference to "probing the physical layout of chromosomes" includes reference to one or more methods for probing the physical layout of chromosomes and equivalents thereof known to those skilled in the art, and so forth.

Also, the use of "and" means "and/or" unless stated otherwise. Similarly, "comprise," "comprises," "comprising" "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

The term "sequencing read" as used herein, refers to a fragment of DNA in which the sequence has been determined.

The term "contigs" as used herein, refers to contiguous regions of DNA sequence. "Contigs" can be determined by any number methods known in the art, such as, by comparing sequencing reads for overlapping sequences, and/or by comparing sequencing reads against a databases of known sequences in order to identify which sequencing reads have a high probability of being contiguous.

The term "subject" as used herein can refer to any eukaryotic or prokaryotic organism.

The term "naked DNA" as used herein can refer to DNA that is substantially free of complexed proteins. For example, it can refer to DNA complexed with less than about 50%, about 40%, about 30%, about 20%, about 10%, about 5%, or about 1% of the endogenous proteins found in the cell nucleus.

The term "reconstituted chromatin" as used herein can refer to forming chromatin formed by complexing isolated nuclear proteins to naked DNA.

The term "read pair" or "read-pair" as used herein can refer to two or more elements that are linked to provide sequence information. In some cases, the number of read-pairs can refer to the number of mappable read-pairs. In other cases, the number of read-pairs can refer to the total number of generated read-pairs.

Unless defined otherwise, all technical and scientific terms used herein have the same meaning as commonly understood to one of ordinary skill in the art to which this disclosure belongs. Although any methods and reagents similar or equivalent to those described herein can be used in the practice of the disclosed methods and compositions, the exemplary methods and materials are now described.

The disclosure provides methods for generating extremely long-range read pairs and to utilize that data for the advancement of all of the aforementioned pursuits. In some embodiments, the disclosure provides methods that produce a highly contiguous and accurate human genomic assembly with only ~300 million read pairs. In other embodiments, the disclosure provides methods that phase 90% or more of heterozygous variants in a human genome with 99% or greater accuracy. Further, the range of the read pairs generated by the disclosure can be extended to span much larger genomic distances. The assembly is produced from a standard shotgun library in addition to an extremely long-range read pair library. In yet other embodiments, the disclosure provides software that is capable of utilizing both of these sets of sequencing data. Phased variants are produced with a single long-range read pair library, the reads from which are mapped to a reference genome and then used to assign variants to one of the individual's two parental chromosomes. Finally, the disclosure provides for the extraction of even larger DNA fragments using known techniques, so as to generate exceptionally long reads.

Figure 5:
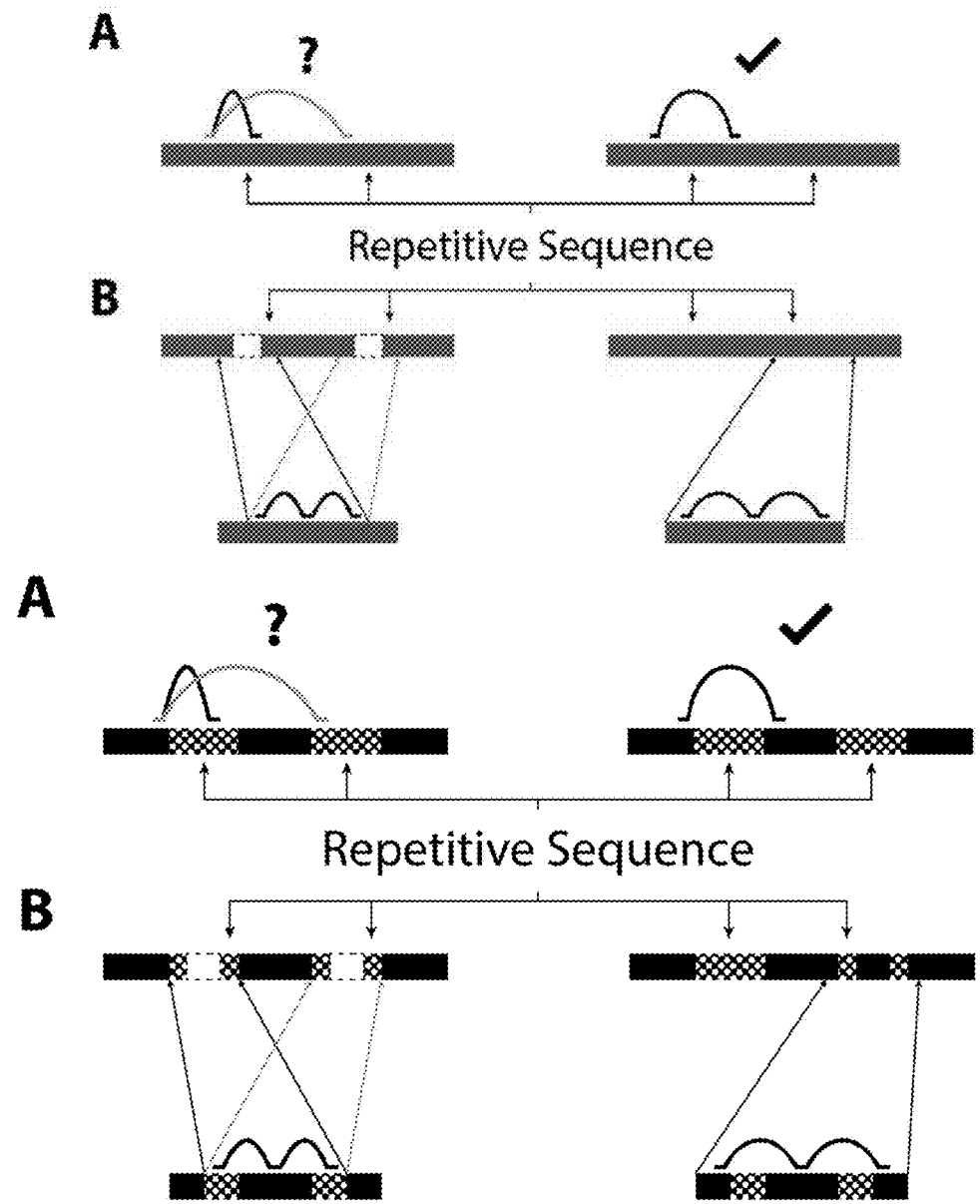
FIG. 5A-B provides an illustration of the ambiguities that arise in genomic assembly and alignment from repetitive regions in the genome. (A) Uncertainty in linkage results from read pairs that cannot bridge repetitive regions. (B) Uncertainty in placement of segment because read pairs cannot span bordering repeats.

The mechanism by which these repeats obstruct assembly and alignment processes is fairly straightforward and is ultimately a consequence of ambiguity (FIG. 5). In the case of large repetitive regions the difficulty is one of span. If a read or read pair is not long enough to span a repetitive region, one cannot confidently connect regions bordering the repetitive element. In the case of smaller repetitive elements the problem is primarily placement. When a region is flanked by two repetitive elements that are common in the genome, determining its exact placement becomes difficult if not impossible due to the similarity of the flanking elements to all others of their class. In both cases it is the lack of distinguishing information in the repeat that makes the identification, and thus placement of a particular repeat challenging. What is needed is the ability to experimentally establish connection between unique segments hemmed or separated by repetitive regions.

The methods of the disclosure greatly advance the field of genomics by overcoming the substantial barriers posed by these repetitive regions, and can thereby enable important advances in many domains of genomic analysis. To perform a de novo assembly with previous technologies, one must either settle for an assembly fragmented into many small scaffolds or commit substantial time and resources to producing a large-insert library or using other approaches to generate a more contiguous assembly. Such approaches may include acquiring very deep sequencing coverage, constructing BAC or fosmid libraries, optical mapping, or, most likely, some combination of these and other techniques. The intense resource and time requirements put such approaches out of reach for most small labs and prevents studying non-model organisms. Since the methods described herein can produce very long-range read pairs, de novo assembly can be achieved with a single sequencing run. This would cut assembly costs by orders of magnitude and shorten the time required from months or years to weeks. In some cases, the methods disclosed herein allow for generating a plurality of read-pairs in less than 14 days, less than 13 days, less than 12 days, less than 11 days, less than 10 days, less than 9 days, less than 8 days, less than 7 days, less than 6 days, less than 5 days, less than 4 days, or in a range between any two of foregoing specified time periods. For example, the methods can allow for generating a plurality of read-pairs in about 10 days to 14 days. Building genomes for even the most niche of organisms would become routine, phylogenetic analyses would suffer no lack of comparisons, and projects such as Genome 10k could be realized.

Similarly, structural and phasing analyses for medical purposes also remain challenging. There is astounding heterogeneity among cancers, individuals with the same type of cancer, or even within the same tumor. Teasing out the causative from consequential effects requires very high precision and throughput at a low per-sample cost. In the domain of personalized medicine, one of the gold standards of genomic care is a sequenced genome with all variants thoroughly characterized and phased, including large and small structural rearrangements and novel mutations. To achieve this with previous technologies demands effort akin to that required for a de novo assembly, which is currently too expensive and laborious to be a routine medical procedure. The disclosed methods can rapidly produce complete, accurate genomes at low cost and can thereby yield many highly sought capabilities in the study and treatment of human disease.

Finally, applying the methods disclosed herein to phasing can combine the convenience of statistical approaches with the accuracy of familial analysis, providing savings—money, labor, and samples—than using either method alone. De novo variant phasing, a highly desirable phasing analysis that is prohibitive with previous technologies, can be performed readily using the methods disclosed herein. This is particularly important as the vast majority of human variation is rare (less than 5% minor allele frequency). Phasing information is valuable for population genetic studies that gain significant advantages from networks of highly connected haplotypes (collections of variants assigned to a single chromosome), relative to unlinked genotypes. Haplotype information can enable higher resolution studies of historical changes in population size, migrations, and exchange between subpopulations, and allows us to trace specific variants back to particular parents and grandparents. This in turn clarifies the genetic transmission of variants associated with disease, and the interplay between variants when brought together in a single individual. The methods of the disclosure can eventually enable the preparation, sequencing, and analysis of extremely long range read pair (XLRP) libraries.

In some embodiments of the disclosure, a tissue or a DNA sample from a subject can be provided and the method can return an assembled genome, alignments with called variants (including large structural variants), phased variant calls, or any additional analyses. In other embodiments, the methods disclosed herein can provide XLRP libraries directly for the individual.

In various embodiments of the disclosure, the methods disclosed herein can generate extremely long-range read pairs separated by large distances. The upper limit of this distance may be improved by the ability to collect DNA samples of large size. In some cases, the read pairs can span up to 50, 60, 70, 80, 90, 100, 125, 150, 175, 200, 225, 250, 300, 400, 500, 600, 700, 800, 900, 1000, 1500, 2000, 2500, 3000, 4000, 5000 kbp or more in genomic distance. In some examples, the read pairs can span up to 500 kbp in genomic distance. In other examples, the read pairs can span up to 2000 kbp in genomic distance. The methods disclosed herein can integrate and build upon standard techniques in molecular biology, and are further well-suited for increases in efficiency, specificity, and genomic coverage. In some cases, the read pairs can be generated in less than about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 60, or 90 days. In some examples, the read pairs can be generated in less than about 14 days. In further examples, the read pairs can be generated in less about 10 days. In some cases, the methods of the present disclosure can provide greater than about 5%, about 10%, about 15%, about 20%, about 30%, about 40%, about 50%, about 60%, about 70%, about 80%, about 90%, about 95%, about 99%, or about 100% of the read pairs with at least about 50%, about 60%, about 70%, about 80%, about 90%, about 95%, about 99%, or about 100% accuracy in correctly ordering and/or orientating the plurality of contigs. For example, the methods can provide about 90 to 100% accuracy in correctly ordering and/or orientating the plurality of contigs.

In other embodiments, the methods disclosed herein can be used with currently employed sequencing technology. For example, the methods can be used in combination with well-tested and/or widely deployed sequencing instruments. In further embodiments, the methods disclosed herein can be used with technologies and approaches derived from currently employed sequencing technology.

The methods of the disclosure dramatically simplify de novo genomic assembly for a wide range of organisms. Using previous technologies, such assemblies are currently limited by the short inserts of economical mate-pair libraries. While it may be possible to generate read pairs at genomic distances up to the 40-50 kbp accessible with fosmids, these are expensive, cumbersome, and too short to span the longest repetitive stretches, including those within centromeres, which in humans range in size from 300 kbp to 5 Mbp. The methods disclosed herein can provide read pairs capable of spanning large distances (e.g., megabases or longer) and thereby overcome these scaffold integrity challenges. Accordingly, producing chromosome-level assemblies can be routine by utilizing the methods of the disclosure. More laborious avenues for assembly—currently costing research labs incredible amounts of time and money, and prohibiting expansive genomic catalogs—may become unnecessary, freeing up resources for more meaningful analyses. Similarly, the acquisition of long-range phasing information can provide tremendous additional power to population genomic, phylogenetic, and disease studies. The methods disclosed herein enable accurate phasing for large numbers of individuals, thus extending the breadth and depth of our ability to probe genomes at the population and deep-time levels.

In the realm of personalized medicine, the XLRP read pairs generated from the methods disclosed herein represents a meaningful advance toward accurate, low-cost, phased, and rapidly produced personal genomes. Current methods are insufficient in their ability to phase variants at long distances, thereby preventing the characterization of the phenotypic impact of compound heterozygous genotypes. Additionally, structural variants of substantial interest for genomic diseases are difficult to accurately identify and characterize with current techniques due to their large size in comparison to reads and read pair inserts used to study them. Read pairs spanning tens of kilobases to megabases or longer can help alleviate this difficulty, thereby allowing for highly parallel and personalized analyses of structural variation.

Basic evolutionary and biomedical research is being driven by technological advances in high-throughput sequencing. Whereas whole genome sequencing and assembly used to be the provenance of large genome sequencing centers, commercially available sequencers are now inexpensive enough that most research universities have one or several of these machines. It is now relatively inexpensive to generate massive quantities of DNA sequence data. However it remains difficult in theory and in practice to produce high-quality, highly contiguous genome sequences with current technology. Furthermore, because most organisms that one would care to analyze, including humans, are diploid, each individual has two haploid copies of the genome. At sites of heterozygosity (e.g., where the allele given by the mother differs from the allele given by the father), it is difficult to know which sets of alleles came from which parent (known as haplotype phasing). This information can be used for performing a number of evolutionary and biomedical studies such as disease and trait association studies.

In various embodiments, the disclosure provides methods for genome assembly that combine technologies for DNA preparation with paired-end sequencing for high-throughput discovery of short, intermediate and long term connections within a given genome. The disclosure further provides methods using these connections to assist in genome assembly, for haplotype phasing, and/or for metagenomic studies. While the methods presented herein can be used to determine the assembly of a subject's genome, it should also be understood that the methods presented herein can also be used to determine the assembly of portions of the subject's genome such as chromosomes, or the assembly of the subject's chromatin of varying lengths.

In some embodiments, the disclosure provides for one or more methods disclosed herein that comprise the step of generating a plurality of contigs from sequencing fragments of target DNA obtained from a subject. Long stretches of target DNA can be fragmented by cutting the DNA with one or more restriction enzymes, shearing the DNA, or a combination thereof. The resulting fragments can be sequenced using high throughput sequencing methods to obtain a plurality of sequencing reads. Examples of high throughput sequencing methods which can be used with the methods of the disclosure include, but are not limited to, 454 pyrosequencing methods developed Roche Diagnostics, "clusters" sequencing methods developed by Illumina, SOLiD and Ion semiconductor sequencing methods developed by Life Technologies, and DNA nanoball sequencing methods developed by Complete Genomics. Overlapping ends of different sequencing reads can then be assembled to form a contig. Alternatively, fragmented target DNA can be cloned into vectors. Cells or organisms are then transfected with the DNA vectors to form a library. After replicating the transfected cells or organisms, the vectors are isolated and sequenced to generate a plurality of sequencing reads. The overlapping ends of different sequencing reads can then be assembled to form a contig.

As shown in FIG. 1, genome assembly, especially with high-throughput sequencing technology can be problematic. Often, the assembly consists of thousands or tens of thousands of short contigs. The order and orientation of these contigs is generally unknown, limiting the usefulness of the genome assembly. Technologies exist to order and orient these scaffolds, but they are generally expensive, labor intensive, and often fail in discovering very long range interactions.

Samples comprising target DNA used to generate contigs can be obtained from a subject by any number of means, including by taking bodily fluids (e.g., blood, urine, serum, lymph, saliva, anal and vaginal secretions, perspiration and semen), taking tissue, or by collecting cells/organisms. The sample obtained may be comprised of a single type of cell/organism, or may be comprised multiple types of cells/organisms. The DNA can be extracted and prepared from the subject's sample. For example, the sample may be treated to lyse a cell comprising the polynucleotide, using known lysis buffers, sonication techniques, electroporation, and the like. The target DNA may be further purified to remove contaminants, such as proteins, by using alcohol extractions, cesium gradients, and/or column chromatography.

In other embodiments of the disclosure, a method to extract very high molecular weight DNA is provided. In some cases, the data from an XLRP library can be improved by increasing the fragment size of the input DNA. In some examples, extracting megabase-sized fragments of DNA from a cell can produce read pairs separated by megabases in the genome. In some cases, the produced read-pairs can provide sequence information over a span of greater than about 10 kB, about 50 kB, about 100 kB, about 200 kB, about 500 kB, about 1 Mb, about 2 Mb, about 5 Mb, about 10 Mb, or about 100 Mb. In some examples, the read-pairs can provide sequence information over a span of greater than about 500 kB. In further examples, the read-pairs can provide sequence information over a span of greater than about 2 Mb. In some cases, the very high molecular weight DNA can be extracted by very gentle cell lysis (Teague, B. et al. (2010) *Proc. Nat. Acad. Sci. USA* 107(24), 10848-53) and agarose plugs (Schwartz, D. C., & Cantor, C. R. (1984) *Cell*, 37(1), 67-75). In other cases, commercially available machines that can purify DNA molecules up to megabases in length can be used to extract very high molecular weight DNA.

In various embodiments, the disclosure provides for one or more methods disclosed herein that comprise the step of probing the physical layout of chromosomes within living cells. Examples of techniques to probe the physical layout of chromosomes through sequencing include the "C" family of techniques, such as chromosome conformation capture ("3C"), circularized chromosome conformation capture ("4C"), carbon-copy chromosome capture ("5C"), and Hi-C based methods; and ChIP based methods, such as ChIP-loop, ChIP-PET. These techniques utilize the fixation of chromatin in live cells to cement spatial relationships in the nucleus. Subsequent processing and sequencing of the products allows a researcher to recover a matrix of proximate associations among genomic regions. With further analysis these associations can be used to produce a three-dimensional geometric map of the chromosomes as they are physically arranged in live nuclei. Such techniques describe the discrete spatial organization of chromosomes in live cells, and provide an accurate view of the functional interactions among chromosomal loci. One issue that plagued these functional studies was the presence of nonspecific interactions, associations present in the data that are attributable to nothing more than chromosomal proximity. In the disclosure, these nonspecific intrachromosomal interactions are captured by the methods presented herein so as to provide valuable information for assembly.

In some embodiments, the intrachromosomal interactions correlate with chromosomal connectivity. In some cases, the intrachromosomal data can aid genomic assembly. In some cases, the chromatin is reconstructed in vitro. This can be advantageous because chromatin—particularly histones, the major protein component of chromatin—is important for fixation under the most common "C" family of techniques for detecting chromatin conformation and structure through sequencing: 3C, 4C, 5C, and Hi-C. Chromatin is highly non-specific in terms of sequence and will generally assemble uniformly across the genome. In some cases, the genomes of species that do not use chromatin can be assembled on a reconstructed chromatin and thereby extend the horizon for the disclosure to all domains of life.

A chromatin conformation capture technique is summarized in FIG. 2. In brief, cross-links are created between genome regions that are in close physical proximity. Crosslinking of proteins (such as histones) to the DNA molecule, e.g. genomic DNA, within chromatin can be accomplished according to a suitable method described in further detail elsewhere herein or otherwise known in the art. In some cases, two or more nucleotide sequences can be cross-linked via proteins bound to one or more nucleotide sequences. One approach is to expose the chromatin to ultraviolet irradiation (Gilmour et al., Proc. Nat'l. Acad. Sci. USA 81:4275-4279, 1984). Crosslinking of polynucleotide segments may also be performed utilizing other approaches, such as chemical or physical (e.g. optical) crosslinking. Suitable chemical crosslinking agents include, but are not limited to, formaldehyde and psoralen (Solomon et al., Proc. NatL. Acad. Sci. USA 82:6470-6474, 1985; Solomon et al., Cell 53:937-947, 1988). For example, cross-linking can be performed by adding 2% formaldehyde to a mixture comprising the DNA molecule and chromatin proteins. Other examples of agents that can be used to cross-link DNA include, but are not limited to, UV light, mitomycin C, nitrogen mustard, melphalan, 1,3-butadiene diepoxide, cis diaminedichloroplatinum(II) and cyclophosphamide. Suitably, the cross-linking agent will form cross-links that bridge relatively short distances such as about 2 Å—thereby selecting intimate interactions that can be reversed.

In some embodiments, the DNA molecule may be immunoprecipitated prior to or after crosslinking. In some cases, the DNA molecule can be fragmented. Fragments may be contacted with a binding partner, such as an antibody that specifically recognizes and binds to acetylated histones, e.g., H3. Examples of such antibodies include, but are not limited to, Anti Acetylated Histone H3, available from Upstate Biotechnology, Lake Placid, N.Y. The polynucleotides from the immunoprecipitate can subsequently be collected from the immunoprecipitate. Prior to fragmenting the chromatin, the acetylated histones can be crosslinked to adjacent polynucleotide sequences. The mixture is then treated to fractionate polynucleotides in the mixture. Fractionation techniques are known in the art and include, for example, shearing techniques to generate smaller genomic fragments. Fragmentation can be accomplished using established methods for fragmenting chromatin, including, for example, sonication, shearing and/or the use of restriction enzymes. The restriction enzyme can have a restriction site of 1, 2, 3, 4, 5, or 6 bases long. Examples restriction enzymes include but are not limited to AatII, Acc65I, AccI, AciI, AclI, AcuI, AfeI, AflII, AflIII, AgeI, AhdI, AleI, AluI, AlwI, AlwNI, ApaI, ApaLI, ApeKI, ApoI, AscI, AseI, AsiSI, AvaI, AvaII, AvrII, BaeGI, BaeI, BamHI, BanI, BanII, BbsI, BbvCI, BbvI, BccI, BceAI, BcgI, BciVI, BclI, BfaI, BfuAI, BfuCI, BglI, BglII, BlpI, BmgBI, BmrI, BmtI, BpmI, Bpu10I, BpuEI, BsaAI, BsaBI, BsaHI, BsaI, BsaJI, BsaWI, BsaXI, BscRI, BscYI, BsgI, BsiEI, BsiHKAI, BsiWI, BslI, BsmAI, BsmBI, BsmFI, BsmI, BsoBI, Bsp1286I, BspCNI, BspDI, BspEI, BspHI, BspMI, BspQI, BsrBI, BerDI, BsrFI, BsrGI, BsrI, BssHII, BssKI, BssSI, BstAPI, BstBI, BstEII, BstNI, BstUI, BstXI, BstYI, BstZ17I, Bsu36I, BtgI, BtgZI, BtsCI, BtsI, Cac8I, ClaI, CspCI, CviAII, CviKI-1, CviQI, DdcI, DpnI, DpnII, DraI, DraIII, DrdI, EacI, EagI, EarI, EciI, Eco53kI, EcoNI, EcoO109I, FooP151I, EcoRI, EcoRV, FatI, FauI, Fnu4HI, FokI, FseI, FspI, HaeII, HaeIII, HgaI, HhaI, HincII, HindIII, HinfI, HinPII, HpaI, HpaII, HphI, Hpy166II, Hpy188I, Hpy188III, Hpy99I, HpyAV, HpyCH4III, HpyCH4IV, HpyCH4V, KasI, KpnI, MboI, MboII, MfeI, MluI, MlyI, MmeI, MnlI, MscI, MseI, MslI, MspA1I, MspI, MwoI, NaeI, NarI, Nb.BbvCI, Nb.BsmI, Nb.BsrDI, Nb.BtsI, NciI, NcoI, NdeI, NgoMIV, NheI, NlaIII, NlaIV, NmeAIII, NotI, NruI, NsiI, NspI, Nt.AlwI, Nt.BbvCI, Nt.BsmAI, Nt.BspQI, Nt.BstNBI, Nt.CviPII, PacI, PaeR7I, PciI, PflFI, PflMI, PhoI, PleI, PmeI, PmlI, PpuMI, PshAI, PsiI, PsuGI, PspOMI, PspXI, PstI, PvuI, PvuII, RsaI, RsrII, SacI, SacII, SalI, SapI, Sau3AI, Sau96I, SbfI, ScaI, ScrFI, SexAI, SfaNI, SfcI, SfiI, SfoI, SgrAI, SmaI, SmlI, SnaBI, SpeI, SphI, SspI, StuI, StyD4I, StyI, SwaI, T, Tagαl, TfiI, TliI, TseI, Tsp45I, Tsp509I, TspMI, TspRI, Tth111I, XbaI, XcmI, XhoI, XmaI, XmnI, and ZraI. The resulting fragments can vary in size. The resulting fragments may also comprise a single-stranded overhand at the 5' or 3' end.

In some embodiments, using sonication techniques, fragments of about 100 to 5000 nucleotides can be obtained. Alternatively, fragments of about 100 to 1000, about 150 to 1000, about 150 to 500, about 200 to 500, or about 200 to 400 nucleotides can be obtained. The sample can be prepared for sequencing of coupled sequence segments that are cross-linked. In some cases, a single, short stretch of polynucleotide can be created, for example, by ligating two sequence segments that were intramolecularly crosslinked. Sequence information may be obtained from the sample using any suitable sequencing technique described in further detail elsewhere herein or otherwise known in the art, such as a high throughput sequencing method. For example, ligation products can be subjected to paired-end sequencing obtaining sequence information from each end of a fragment. Pairs of sequence segments can be represented in the obtained sequence information, associating haplotyping information over a linear distance separating the two sequence segments along the polynucleotide.

One feature of the data generated by Hi-C is that most reads pairs, when mapped back to the genome, are found to be in close linear proximity. That is, most read pairs are found to be close to one another in the genome. In the resulting data sets, the probability of intrachromosomal contacts is on average much higher than that of interchromosomal contacts, as expected if chromosomes occupy distinct territories. Moreover, although the probability of interaction decays rapidly with linear distance, even loci separated by >200 Mb on the same chromosome are more likely to interact than loci on different chromosomes. In detecting long-range intra-chromosomal and especially inter-chromosomal contacts, this "background" of short and intermediate range intra-chromosomal contacts are background noise to be factored out using Hi-C analysis.

Notably, Hi-C experiments in eukaryotes have shown, in addition to species-specific and cell type-specific chromatin interactions, two canonical interaction patterns. One pattern, distance-dependent decay (DDD), is a general trend of decay in interaction frequency as a function of genomic distance. The second pattern, cis-trans ratio (CTR), is a significantly higher interaction frequency between loci located on the same chromosome, even when separated by tens of megabases of sequence, versus loci on different chromosomes. These patterns may reflect general polymer dynamics, where proximal loci have a higher probability of randomly interacting, as well as specific nuclear organization features such as the formation of chromosome territories, the phenomenon of interphase chromosomes tending to occupy distinct volumes in the nucleus with little mixing. Although the exact details of these two patterns may vary between species, cell types and cellular conditions, they are ubiquitous and prominent. These patterns are so strong and consistent that they are used to assess experiment quality and are usually normalized out of the data in order to reveal detailed interactions. However, in the methods disclosed herein, genome assembly can take advantage of the three-dimensional structure of genomes. Features which make the canonical Hi-C interaction patterns a hindrance for the analysis of specific looping interactions, namely their ubiquity, strength and consistency, can be used as powerful tool for estimating the genomic position of contigs.

In a particular implementation, examination of the physical distance between intra-chromosomal read pairs indicates several useful features of the data with respect to genome assembly. First, shorter range interactions are more common than longer-range interactions (e.g., see FIG. 6). That is, each read of a read-pair is more likely to be mated with a region close by in the actual genome than it is to be with a region that is far away. Second, there is a long tail of intermediate and long-range interactions. That is, read-pairs carry information about intra-chromosomal arrangement at kilobase (kB) or even megabase (Mb) distances. For example, read-pairs can provide sequence information over a span of greater than about 10 kB, about 50 kB, about 100 kB, about 200 kB, about 500 kB, about 1 Mb, about 2 Mb, about 5 Mb, about 10 Mb, or about 100 Mb. These features of the data simply indicate that regions of the genome that are nearby on the same chromosome are more likely to be in close physical proximity—an expected result because they are chemically linked to one another through the DNA backbone. It was speculated that genome-wide chromatin interaction data sets, such as those generated by Hi-C., would provide long-range information about the grouping and linear organization of sequences along entire chromosomes.

Although the experimental methods for Hi-C are straightforward and relatively low cost, current protocols for genome assembly and haplotyping require $10^6$-$10^8$ cells, a fairly large amount of material that may not be feasible to obtain, particularly from certain human patient samples. By contrast, the methods disclosed herein include methods that allow for accurate and predictive results for genotype assembly, haplotype phasing, and metagenomics with significantly less material from cells. For example, less than about 0.1 µg, about 0.2 µg, about 0.3 µg, about 0.4 µg, about 0.5 µg, about 0.6 µg, about 0.7 µg, about 0.8 µg, about 0.9 µg, about 1.0 µg, about 1.2 µg, about 1.4 µg, about 1.6 µg, about 1.8 µg, about 2.0 µg, about 2.5 µg, about 3.0 µg, about 3.5 µg, about 4.0 µg, about 4.5 µg, about 5.0 µg, about 6.0 µg, about 7.0 µg, about 8.0 µg, about 9.0 µg, about 10 µg, about 15 µg, about 20 µg, about 30 µg, about 40 µg, about 50 µg, about 60 µg, about 70 µg, about 80 µg, about 90 µg, about 100 µg, about 150 µg, about 200 µg, about 300 µg, about 400 µg, about 500 µg, about 600 µg, about 700 µg, about 800 µg, about 900 µg, or about 1000 µg of DNA can be used with the methods disclosed herein. In some examples, the DNA used in the methods disclosed herein can be extracted from less than about 1,000,000, about 500,000, about 100,000, about 50,000, about 10,000, about 5,000, about 1,000, about 5,000, or about 1,000, about 500, or about 100 cells.

Universally, procedures for probing the physical layout of chromosomes, such as Hi-C based techniques, utilize chromatin that is formed within a cell/organism, such as chromatin isolated from cultured cells or primary tissue. The disclosure provides not only for the use of such techniques with chromatin isolated from a cell/organism but also with reconstituted chromatin. Reconstituted chromatin is differentiated from chromatin formed within a cell/organism over various features. First, for many samples, the collection of naked DNA samples can be achieved by using a variety of noninvasive to invasive methods, such as by collecting bodily fluids, swabbing buccal or rectal areas, taking epithelial samples, etc. Second, reconstituting chromatin substantially prevents the formation of inter-chromosomal and other long-range interactions that generate artifacts for genome assembly and haplotype phasing. In some cases, a sample may have less than about 20, 15, 12, 11, 10, 9, 8, 7, 6, 5, 4, 3, 2, 1, 0.5, 0.4, 0.3, 0.2, 0.1% or less inter-chromosomal or intermolecular crosslinking according to the methods and compositions of the disclosure. In some examples, the sample may have less than about 5% inter-chromosomal or intermolecular crosslinking. In some examples, the sample may have less than about 3% inter-chromosomal or intermolecular crosslinking. In further examples, may have less than about 1% inter-chromosomal or intermolecular crosslinking. Third, the frequency of sites that are capable of crosslinking and thus the frequency of intramolecular crosslinks within the polynucleotide can be adjusted. For example, the ratio of DNA to histones can be varied, such that the nucleosome density can be adjusted to a desired value. In some cases, the nucleosome density is reduced below the physiological level. Accordingly, the distribution of crosslinks can be altered to favor longer-range interactions. In some embodiments, sub-samples with varying cross-linking density may be prepared to cover both short- and long-range associations. For example, the cross-linking conditions can be adjusted such that at least about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 25%, about 30%, about 40%, about 45%, about 50%, about 60%, about 70%, about 80%, about 90%, about 95%, or about 100% of the crosslinks occur between DNA segments that are at least about 50 kb, about 60 kb, about 70 kb, about 80 kb, about 90 kb, about 100 kb, about 110 kb, about 120 kb, about 130 kb, about 140 kb, about 150 kb, about 160 kb, about 180 kb, about 200 kb, about 250 kb, about 300 kb, about 350 kb, about 400 kb, about 450 kb, or about 500 kb apart on the sample DNA molecule.

In various embodiments, the disclosure provides a variety of methods that enable the mapping of the plurality of read pairs to the plurality of contigs. There are several publicly available computer programs for mapping reads to contig sequences. These read-mapping programs data also provide data describing how unique a particular read-mapping is within the genome. From the population of reads that map uniquely, with high confidence within a contig, we can infer the distribution of distances between reads in each read pair. These are the data shown in FIG. 6. For read pairs whose reads map confidently to different contigs, this mapping data implies a connection between the two contigs in question. It also implies a distance between the two contigs that is proportional to the distribution of distances learned from the analysis described above. Thus, each read pair whose reads map to different contigs implies a connection between those two contigs in a correct assembly. The connections inferred from all such mapped read pairs can be summarized in an adjacency matrix wherein each contig is represented by both a row and column. Read pairs that connect contigs are marked as a non-zero value in the corresponding row and column denoting the contigs to which the reads in the read pair were mapped. Most of the read pairs will map within in a contig, and from which the distribution of distances between read pairs can be learned, and from which an adjacency matrix of contigs can be constructed using read pairs that map to different contigs.

In various embodiments, the disclosure provides methods comprising constructing an adjacency matrix of contigs using the read-mapping data from the read-pair data. In some embodiments, the adjacency matrix uses a weighting scheme for read pairs that incorporate the tendency for short-range interactions over long-range interactions (e.g., see FIG. 3). Read pairs spanning shorter distances are generally more common than read pairs that span longer distances. A function describing the probability of a particular distance can be fit using the read pair data that map to a single contig to learn this distribution. Therefore, one important feature of read pairs that map to different contigs is the position on the contig where they map. For read pairs that both map near one end of a contig, the inferred distance between these contigs can be short and therefore the distance between the joined reads small. Since shorter distances between read pairs are more common than longer distances, this configuration provides stronger evidence that these two contigs are adjacent than would reads mapping far from the edges of the contig. Therefore, the connections in the adjacency matrix are further weighted by the distance of the reads to the edge of the contigs. In further embodiments, the adjacency matrix can further be re-scaled to down-weight the high number of contacts on some contigs that represent promiscuous regions of the genome. These regions of the genome, identifiable by having a high proportion of reads mapping to them, are a priori more likely to contain spurious read mappings that might misinform assembly. In yet further embodiments, this scaling can be directed by searching for one or more conserved binding sites for one or more agents that regulate the scaffolding interactions of chromatin, such as transcriptional repressor CTCF, endocrine receptors, cohesins, or covalently modified histones.

In some embodiments, the disclosure provides for one or more methods disclosed herein that comprise a step of analyzing the adjacency matrix to determine a path through the contigs that represent their order and/or orientation to the genome. In other embodiments, the path through the contigs can be chosen so that each contig is visited exactly once. In further embodiments, the path through the contigs is chosen so that the path through the adjacency matrix maximizes the sum of edge-weights visited. In this way, the most probably contig connections are proposed for the correct assembly. In yet further embodiments, the path through the contigs can be chosen so that each contig is visited exactly once and that edge-weighting of adjacency matrix is maximized.

In diploid genomes, it often important to know which allelic variants are linked on the same chromosome. This is known as the haplotype phasing. Short reads from high-throughput sequence data rarely allow one to directly observe which allelic variants are linked. Computational inference of haplotype phasing can be unreliable at long distances. The disclosure provides one or methods that allow for determining which allelic variants are linked using allelic variants on read pairs.

In various embodiments, the methods and compositions of the disclosure enable the haplotype phasing of diploid or polyploid genomes with regard to a plurality of allelic variants. The methods described herein can thus provide for the determination of linked allelic variants are linked based on variant information from read pairs and/or assembled contigs using the same. Examples of allelic variants include, but are not limited to those that are known from the 1000 genomes, UK10K, HapMap and other projects for discovering genetic variation among humans. Disease association to a specific gene can be revealed more easily by having haplotype phasing data as demonstrated, for example, by the finding of unlinked, inactivating mutations in both copies SH3TC2 leading to Charcot-Marie-Tooth neuropathy (Lupski J R, Reid J G, Gonzaga-Jauregui C, et al. *N. Engl. J. Med.* 362:1181-91, 2010) and unlinked, inactivating mutations in both copies of ABCG5 leading to hypercholesterolemia 9 (Rios J, Stein E, Shendure J, et al. *Hum. Mol. Genet.* 19:4313-18, 2010).

Humans are heterozygous at an average of 1 site in 1,000. In some cases, a single lane of data using high throughput sequencing methods can generate at least about 150,000,000 read pairs. Read pairs can be about 100 base pairs long. From these parameters, one-tenth of all reads from a human sample is estimated to cover a heterozygous site. Thus, on average one-hundredth of all read pairs from a human sample is estimated to cover a pair of heterozygous sites. Accordingly, about 1,500,000 read pairs (one-hundredth of 150,000,000) provide phasing data using a single lane. With approximately 3 billion bases in the human genome, and one in one-thousand being heterozygous, there are approximately 3 million heterozygous sites in an average human genome. With about 1,500,000 read pairs that represent a pair of heterozygous sites, the average coverage of each heterozygous site to be phased using a single lane of a high throughput sequence method is about (1×), using a typical high throughput sequencing machine. A diploid human genome can therefore be reliably and completely phased with one lane of a high-throughput sequence data relating sequence variants from a sample that is prepared using the methods disclosed herein. In some examples, a lane of data can be a set of DNA sequence read data. In further examples, a lane of data can be a set of DNA sequence read data from a single run of a high throughput sequencing instrument.

As the human genome consists of two homologous sets of chromosomes, understanding the true genetic makeup of an individual requires delineation of the maternal and paternal copies or haplotypes of the genetic material. Obtaining a haplotype in an individual is useful in several ways. First, haplotypes are useful clinically in predicting outcomes for donor-host matching in organ transplantation and are increasingly used as a means to detect disease associations. Second, in genes that show compound heterozygosity, haplotypes provide information as to whether two deleterious variants are located on the same allele, greatly affecting the prediction of whether inheritance of these variants is harmful. Third, haplotypes from groups of individuals have provided information on population structure and the evolutionary history of the human race. Lastly, recently described widespread allelic imbalances in gene expression suggest that genetic or epigenetic differences between alleles may contribute to quantitative differences in expression. An understanding of haplotype structure will delineate the mechanisms of variants that contribute to allelic imbalances.

In certain embodiments, the methods disclosed herein comprise an in vitro technique to fix and capture associations among distant regions of a genome as needed for long-range linkage and phasing. In some cases, the method comprises constructing and sequencing an XLRP library to deliver very genomically distant read pairs. In some cases, the interactions primarily arise from the random associations within a single DNA fragment. In some examples, the genomic distance between segments can be inferred because segments that are near to each other in a DNA molecule interact more often and with higher probability, while interactions between distant portions of the molecule will be less frequent. Consequently there is a systematic relationship between the number of pairs connecting two loci and their proximity on the input DNA. The disclosure can produce read pairs capable of spanning the largest DNA fragments in an extraction, as demonstrated in FIG. 2. The input DNA for this library had a maximum length of 150 kbp, which is the longest meaningful read pair we observe from the sequencing data. This suggests that the present method can link still more genomically distant loci if provided larger input DNA fragments. By applying improved assembly software tools that are specifically adapted to handle the type of data produced by the present method, a complete genomic assembly may be possible.

Extremely high phasing accuracy can be achieved by the data produced using the methods and compositions of the disclosure. In comparison to previous methods, the methods described herein can phase a higher proportion of the variants. Phasing can be achieved while maintaining high levels of accuracy. This phase information can be extended to longer ranges, for example greater than about 200 kbp, about 300 kbp, about 400 kbp, about 500 kbp, about 600 kbp, about 700 kbp, about 800 kbp, about 900 kbp, about 1 Mbp, about 2 Mbp, about 3 Mbp, about 4 Mbp, about 5 Mbp, or about 10 Mbp. In some embodiments, more than 90% of the heterozygous SNPs for a human sample can be phased at an accuracy greater than 99% using less than about 250 million reads or read pairs, e.g. by using only 1 lane of Illumina HiSeq data. In other cases, more than about 40%, 50%, 60%, 70%, 80%, 90%, 95% or 99% of the heterozygous SNPs for a human sample can be phased at an accuracy greater than about 70%, 80%, 90%, 95%, or 99% using less than about 250 million or about 500 million reads or read pairs, e.g. by using only 1 or 2 lanes of Illumina HiSeq data. For example, more than 950 or 990 of the heterozygous SNPs for a human sample can be phase at an accuracy greater than about 95% or 99% using less about 250 million or about 500 million reads. In further cases, additional variants can be captured by increasing the read length to about 200 bp, 250 bp, 300 bp, 350 bp, 400 bp, 450 bp, 500 bp, 600 bp, 800 bp, 1000 bp, 1500 bp, 2 kbp, 3 kbp, 4 kbp, 5 kbp, 10 kbp, 20 kbp, 50 kbp, or 100 kbp.

Figure 6:
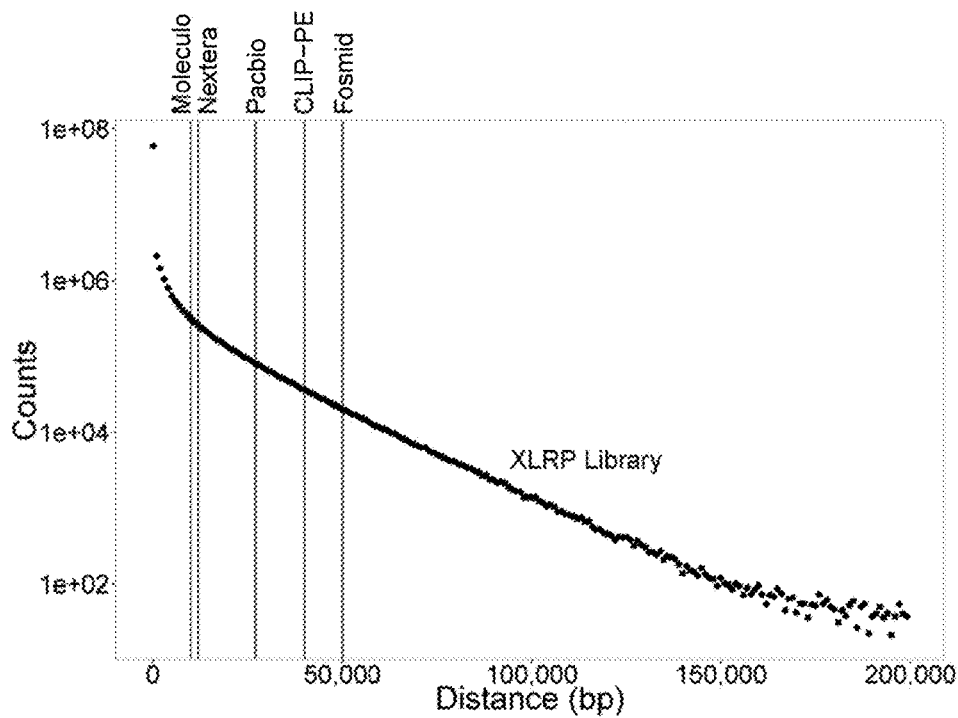
FIG. 6 illustrates the distribution of genomic distances between read pairs from a human XLRP library. Maximum distances achievable with other technologies are indicated for comparison.

In other embodiments of the disclosure, the data from an XLRP library can be used to confirm the phasing capabilities of the long-range read pairs. As shown in FIG. 6, the accuracy of those results is on par with the best technologies previously available, but further extending to significantly longer distances. The current sample preparation protocol for a particular sequencing method recognizes variants located within a read-length, e.g. 150 bp, of a targeted restriction site for phasing. In one example, from an XLRP library built for NA12878, a benchmark sample for assembly, 44% of the 1,703,909 heterozygous SNPs present were phased with an accuracy greater than 99%. In some cases, this proportion can be expanded to nearly all variable sites with the judicious choice of restriction enzyme or with combinations of different enzymes.

In some embodiments, the compositions and methods described herein allow for the investigation of meta-genomes, for example those found in the human gut. Accordingly, the partial or whole genomic sequences of some or all organisms that inhabit a given ecological environment can be investigated. Examples include random sequencing of all gut microbes, the microbes found on certain areas of skin, and the microbes that live in toxic waste sites. The composition of the microbe population in these environments can be determined using the compositions and methods described herein and as well as the aspects of interrelated biochemistries encoded by their respective genomes. The methods described herein can enable metagenomic studies from complex biological environments, for example, those that comprise more than 2, 3, 4, 5, 6, 7, 8, 9, 10, 12, 15, 20, 25, 30, 40, 50, 60, 70, 80, 90, 100, 125, 150, 175, 200, 250, 300, 400, 500, 600, 700, 800, 900, 1000, 5000, 10000 or more organisms and/or variants of organisms.

High degrees of accuracy required by cancer genome sequencing can be achieved using the methods and systems described herein. Inaccurate reference genomes can make base-calling challenges when sequencing cancer genomes. Heterogeneous samples and small starting materials, for example a sample obtained by biopsy introduce additional challenges. Further, detection of large scale structural variants and/or losses of heterozygosity is often crucial for cancer genome sequencing, as well as the ability to differentiate between somatic variants and errors in base-calling.

Systems and methods described herein may generate accurate long sequences from complex samples containing 2, 3, 4, 5, 6, 7, 8, 9, 10, 12, 15, 20 or more varying genomes. Mixed samples of normal, benign, and/or tumor origin may be analyzed, optionally without the need for a normal control. In some embodiments, starting samples as little as 100 ng or even as little as hundreds of genome equivalents are utilized to generate accurate long sequences. Systems and methods described herein may allow for detection of large scale structural variants and rearrangements. Phased variant calls may be obtained over long sequences spanning about 1 kbp, about 2 kbp, about 5 kbp, about 10 kbp, 20 kbp, about 50 kbp, about 100 kbp, about 200 kbp, about 500 kbp, about 1 Mbp, about 2 Mbp, about 5 Mbp, about 10 Mbp, about 20 Mbp, about 50 Mbp, or about 100 Mbp or more nucleotides. For example, phase variant call may be obtained over long sequences spanning about 1 Mbp or about 2 Mbp.

Haplotypes determined using the methods and systems described herein may be assigned to computational resources, for example computational resources over a network, such as a cloud system. Short variant calls can be corrected, if necessary, using relevant information that is stored in the computational resources. Structural variants can be detected based on the combined information from short variant calls and the information stored in the computational resources. Problematic parts of the genome, such as segmental duplications, regions prone to structural variation, the highly variable and medically relevant MHC region, centromeric and telomeric regions, and other heterochromatic regions including but limited to those with repeat regions, low sequence accuracy, high variant rates, ALU repeats, segmental duplications, or any other relevant problematic parts known in the art, can be reassembled for increased accuracy.

A sample type can be assigned to the sequence information either locally or in a networked computational resource, such as a cloud. In cases where the source of the information is known, for example when the source of the information is from a cancer or normal tissue, the source can be assigned to the sample as part of a sample type. Other sample type examples generally include, but are not limited to, tissue type, sample collection method, presence of infection, type of infection, processing method, size of the sample, etc. In cases where a complete or partial comparison genome sequence is available, such as a normal genome in comparison to a cancer genome, the differences between the sample data and the comparison genome sequence can be determined and optionally output.

The methods of the can be used in the analysis of genetic information of selective genomic regions of interest as well as genomic regions which may interact with the selective region of interest. Amplification methods as disclosed herein can be used in the devices, kits, and methods known to the art for genetic analysis, such as, but not limited to those found in U.S. Pat. Nos. 6,449,562, 6,287,766, 7,361,468, 7,414,117, 6,225,109, and 6,110,709. In some cases, amplification methods of the present disclosure can be used to amplify target nucleic acid for DNA hybridization studies to determine the presence or absence of polymorphisms. The polymorphisms, or alleles, can be associated with diseases or conditions such as genetic disease. In other cases the polymorphisms can be associated with susceptibility to diseases or conditions, for example, polymorphisms associated with addiction, degenerative and age related conditions, cancer, and the like. In other cases, the polymorphisms can be associated with beneficial traits such as increased coronary health, or resistance to diseases such as HIV or malaria, or resistance to degenerative diseases such as osteoporosis, Alzheimer's or dementia.

The compositions and methods of the disclosure can be used for diagnostic, prognostic, therapeutic, patient stratification, drug development, treatment selection, and screening purposes. The present disclosure provides the advantage that many different target molecules can be analyzed at one time from a single biomolecular sample using the methods of the disclosure. This allows, for example, for several diagnostic tests to be performed on one sample.

The composition and methods of the disclosure can be used in genomics. The methods described herein can provide an answer rapidly which is very desirable for this application. The methods and composition described herein can be used in the process of finding biomarkers that may be used for diagnostics or prognostics and as indicators of health and disease. The methods and composition described herein can be used to screen for drugs, e.g., drug development, selection of treatment, determination of treatment efficacy and/or identify targets for pharmaceutical development. The ability to test gene expression on screening assays involving drugs is very important because proteins are the final gene product in the body. In some embodiments, the methods and compositions described herein will measure both protein and gene expression simultaneously which will provide the most information regarding the particular screening being performed.

The composition and methods of the disclosure can be used in gene expression analysis. The methods described herein discriminate between nucleotide sequences. The difference between the target nucleotide sequences can be, for example, a single nucleic acid base difference, a nucleic acid deletion, a nucleic acid insertion, or rearrangement. Such sequence differences involving more than one base can also be detected. The process of the present disclosure is able to detect infectious diseases, genetic diseases, and cancer. It is also useful in environmental monitoring, forensics, and food science. Examples of genetic analyses that can be performed on nucleic acids include e.g., SNP detection, STR detection, RNA expression analysis, promoter methylation, gene expression, virus detection, viral subtyping and drug resistance.

The present methods can be applied to the analysis of biomolecular samples obtained or derived from a patient so as to determine whether a diseased cell type is present in the sample, the stage of the disease, the prognosis for the patient, the ability to the patient to respond to a particular treatment, or the best treatment for the patient. The present methods can also be applied to identify biomarkers for a particular disease.

In some embodiments, the methods described herein are used in the diagnosis of a condition. As used herein the term "diagnose" or "diagnosis" of a condition may include predicting or diagnosing the condition, determining predisposition to the condition, monitoring treatment of the condition, diagnosing a therapeutic response of the disease, or prognosis of the condition, condition progression, or response to particular treatment of the condition. For example, a blood sample can be assayed according to any of the methods described herein to determine the presence and/or quantity of markers of a disease or malignant cell type in the sample, thereby diagnosing or staging the a disease or a cancer.

In some embodiments, the methods and composition described herein are used for the diagnosis and prognosis of a condition.

Numerous immunologic, proliferative and malignant diseases and disorders are especially amenable to the methods described herein. Immunologic diseases and disorders include allergic diseases and disorders, disorders of immune function, and autoimmune diseases and conditions. Allergic diseases and disorders include but are not limited to allergic rhinitis, allergic conjunctivitis, allergic asthma, atopic eczema, atopic dermatitis, and food allergy. Immunodeficiencies include but are not limited to severe combined immunodeficiency (SCID), hypereosinophilic syndrome, chronic granulomatous disease, leukocyte adhesion deficiency I and II, hyper IgE syndrome, Chediak Higashi, neutrophilias, neutropenias, aplasias, Agammaglobulinemia, hyper-IgM syndromes, DiGeorge/Velocardial-facial syndromes and Interferon gamma-TH1 pathway defects. Autoimmune and immune dysregulation disorders include but are not limited to rheumatoid arthritis, diabetes, systemic lupus erythematosus, Graves' disease, Graves ophthalmopathy, Crohn's disease, multiple sclerosis, psoriasis, systemic sclerosis, goiter and struma lymphomatosa (Hashimoto's thyroiditis, lymphadenoid goiter), alopecia aerata, autoimmune myocarditis, lichen sclerosis, autoimmune uveitis, Addison's disease, atrophic gastritis, myasthenia gravis, idiopathic thrombocytopenic purpura, hemolytic anemia, primary biliary cirrhosis, Wegener's granulomatosis, polyarteritis nodosa, and inflammatory bowel disease, allograft rejection and tissue destructive from allergic reactions to infectious microorganisms or to environmental antigens.

Proliferative diseases and disorders that may be evaluated by the methods of the disclosure include, but are not limited to, hemangiomatosis in newborns; secondary progressive multiple sclerosis; chronic progressive myelodegenerative disease; neurofibromatosis; ganglioneuromatosis; keloid formation; Paget's Disease of the bone; fibrocystic disease (e.g., of the breast or uterus); sarcoidosis; Peronies and Duputren's fibrosis, cirrhosis, atherosclerosis and vascular restenosis.

Malignant diseases and disorders that may be evaluated by the methods of the disclosure include both hematologic malignancies and solid tumors.

Hematologic malignancies are especially amenable to the methods of the disclosure when the sample is a blood sample, because such malignancies involve changes in blood-borne cells. Such malignancies include non-Hodgkin's lymphoma, Hodgkin's lymphoma, non-B cell lymphomas, and other lymphomas, acute or chronic leukemias, polycythemias, thrombocythemias, multiple myeloma, myelodysplastic disorders, myeloproliferative disorders, myelofibroses, atypical immune lymphoproliferations and plasma cell disorders.

Plasma cell disorders that may be evaluated by the methods of the disclosure include multiple myeloma, amyloidosis and Waldenstrom's macroglobulinemia.

Example of solid tumors include, but are not limited to, colon cancer, breast cancer, lung cancer, prostate cancer, brain tumors, central nervous system tumors, bladder tumors, melanomas, liver cancer, osteosarcoma and other bone cancers, testicular and ovarian carcinomas, head and neck tumors, and cervical neoplasms.

Genetic diseases can also be detected by the process of the present disclosure. This can be carried out by prenatal or post-natal screening for chromosomal and genetic aberrations or for genetic diseases. Examples of detectable genetic diseases include: 21 hydroxylase deficiency, cystic fibrosis, Fragile X Syndrome, Turner Syndrome, Duchenne Muscular Dystrophy, Down Syndrome or other trisomies, heart disease, single gene diseases, HLA typing, phenylketonuria, sickle cell anemia, Tay-Sachs Disease, thalassemia, Klinefelter Syndrome, Huntington Disease, autoimmune diseases, lipidosis, obesity defects, hemophilia, inborn errors of metabolism, and diabetes.

The methods described herein can be used to diagnose pathogen infections, for example infections by intracellular bacteria and viruses, by determining the presence and/or quantity of markers of bacterium or virus, respectively, in the sample.

A wide variety of infectious diseases can be detected by the process of the present disclosure. The infectious diseases can be caused by bacterial, viral, parasite, and fungal infectious agents. The resistance of various infectious agents to drugs can also be determined using the present disclosure.

Bacterial infectious agents which can be detected by the present disclosure include *Escherichia coli, Salmonella, Shigella, KlESBiella, Pseudomonas, Listeria monocytogenes, Mycobacterium tuberculosis, Mycobacterium avium-intracellulare, Yersinia, Francisella, Pasteurella, Brucella, Clostridia, Bordetella pertussis, Bacteroides, Staphylococcus aureus, Streptococcus pneumonia,* B-Hemolytic strep., *Corynebacteria, Legionella, Mycoplasma, Ureaplasma, Chlamydia, Neisseria gonorrhea, Neisseria meningitides,*

*Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia*, and *Acitnomycetes*.

Fungal infectious agents which can be detected by the present disclosure include *Cryptococcus neoformans, Blastomyces dermatitidis, Histoplasma capsulatum, Coccidioides immitis, Paracoccidioides brasiliensis, Candida albicans, Aspergillus fumigautus, Phycomycetes (Rhizopus), Sporothrix schenckii, Chromomycosis*, and *Maduromycosis*.

Viral infectious agents which can be detected by the present disclosure include human immunodeficiency virus, human T-cell lymphocytotrophic virus, hepatitis viruses (e.g., Hepatitis B Virus and Hepatitis C Virus), Epstein-Barr virus, cytomegalovirus, human papillomaviruses, orthomyxo viruses, paramyxo viruses, adenoviruses, corona viruses, rhabdo viruses, polio viruses, toga viruses, bunya viruses, arena viruses, rubella viruses, and reo viruses.

Parasitic agents which can be detected by the present disclosure include *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis, trematodes, Diphyllobothrium latum, Taenia* spp., *Pneumocystis carinii*, and *Necator americanis*.

The present disclosure is also useful for detection of drug resistance by infectious agents. For example, vancomycin-resistant *Enterococcus faecium*, methicillin-resistant *Staphylococcus aureus*, penicillin-resistant *Streptococcus pneumoniae*, multi-drug resistant *Mycobacterium tuberculosis*, and AZT-resistant human immunodeficiency virus can all be identified with the present disclosure Thus, the target molecules detected using the compositions and methods of the disclosure can be either patient markers (such as a cancer marker) or markers of infection with a foreign agent, such as bacterial or viral markers.

The compositions and methods of the disclosure can be used to identify and/or quantify a target molecule whose abundance is indicative of a biological state or disease condition, for example, blood markers that are upregulated or downregulated as a result of a disease state.

In some embodiments, the methods and compositions of the present disclosure can be used for cytokine expression. The low sensitivity of the methods described herein would be helpful for early detection of cytokines, e.g., as biomarkers of a condition, diagnosis or prognosis of a disease such as cancer, and the identification of subclinical conditions.

The different samples from which the target polynucleotides are derived can comprise multiple samples from the same individual, samples from different individuals, or combinations thereof. In some embodiments, a sample comprises a plurality of polynucleotides from a single individual. In some embodiments, a sample comprises a plurality of polynucleotides from two or more individuals. An individual is any organism or portion thereof from which target polynucleotides can be derived, non-limiting examples of which include plants, animals, fungi, protists, monerans, viruses, mitochondria, and chloroplasts. Sample polynucleotides can be isolated from a subject, such as a cell sample, tissue sample, or organ sample derived therefrom, including, for example, cultured cell lines, biopsy, blood sample, or fluid sample containing a cell. The subject may be an animal, including but not limited to, an animal such as a cow, a pig, a mouse, a rat, a chicken, a cat, a dog, etc., and is usually a mammal, such as a human. Samples can also be artificially derived, such as by chemical synthesis. In some embodiments, the samples comprise DNA. In some embodiments, the samples comprise genomic DNA. In some embodiments, the samples comprise mitochondrial DNA, chloroplast DNA, plasmid DNA, bacterial artificial chromosomes, yeast artificial chromosomes, oligonucleotide tags, or combinations thereof. In some embodiments, the samples comprise DNA generated by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can comprise sequences specific to one or more targets, random sequences, partially random sequences, and combinations thereof. Reaction conditions suitable for primer extension reactions are known in the art. In general, sample polynucleotides comprise any polynucleotide present in a sample, which may or may not include target polynucleotides.

In some embodiments, nucleic acid template molecules (e.g., DNA or RNA) are isolated from a biological sample containing a variety of other components, such as proteins, lipids and non-template nucleic acids. Nucleic acid template molecules can be obtained from any cellular material, obtained from an animal, plant, bacterium, fungus, or any other cellular organism. Biological samples for use in the present disclosure include viral particles or preparations. Nucleic acid template molecules can be obtained directly from an organism or from a biological sample obtained from an organism, e.g., from blood, urine, cerebrospinal fluid, seminal fluid, saliva, sputum, stool and tissue. Any tissue or body fluid specimen may be used as a source for nucleic acid for use in the disclosure. Nucleic acid template molecules can also be isolated from cultured cells, such as a primary cell culture or a cell line. The cells or tissues from which template nucleic acids are obtained can be infected with a virus or other intracellular pathogen. A sample can also be total RNA extracted from a biological specimen, a cDNA library, viral, or genomic DNA. A sample may also be isolated DNA from a non-cellular origin, e.g. amplified/isolated DNA from the freezer.

Methods for the extraction and purification of nucleic acids are well known in the art. For example, nucleic acids can be purified by organic extraction with phenol, phenol/chloroform/isoamyl alcohol, or similar formulations, including TRIzol and TriReagent. Other non-limiting examples of extraction techniques include: (1) organic extraction followed by ethanol precipitation, e.g., using a phenol/chloroform organic reagent (Ausubel et al., 1993), with or without the use of an automated nucleic acid extractor, e.g., the Model 341 DNA Extractor available from Applied Biosystems (Foster City, Calif.); (2) stationary phase adsorption methods (U.S. Pat. No. 5,234,809; Walsh et al., 1991); and (3) salt-induced nucleic acid precipitation methods (Miller et al., (1988), such precipitation methods being typically referred to as "salting-out" methods. Another example of nucleic acid isolation and/or purification includes the use of magnetic particles to which nucleic acids can specifically or non-specifically bind, followed by isolation of the beads using a magnet, and washing and eluting the nucleic acids from the beads (see e.g. U.S. Pat. No. 5,705,628). In some embodiments, the above isolation methods may be preceded by an enzyme digestion step to help eliminate unwanted protein from the sample, e.g., digestion with proteinase K, or other like proteases. See, e.g., U.S. Pat. No. 7,001,724. If desired, RNase inhibitors may be added to the lysis buffer. For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic. In addition to an initial nucleic isolation step, purification of nucleic acids can be performed after any step in the methods of the disclosure, such as to remove excess or unwanted reagents, reactants, or products.

Nucleic acid template molecules can be obtained as described in U.S. Patent Application Publication Number US2002/0190663 A1, published Oct. 9, 2003. Generally, nucleic acid can be extracted from a biological sample by a variety of techniques such as those described by Maniatis, et al., Molecular Cloning: A Laboratory Manual, Cold Spring Harbor, N.Y., pp. 280-281 (1982). In some cases, the nucleic acids can be first extract from the biological samples and then cross-linked in vitro. In some cases, native association proteins (e.g. histones) can be further removed from the nucleic acids.

In other embodiments, the disclosure can be easily applied to any high molecular weight double stranded DNA including, for example, DNA isolated from tissues, cell culture, bodily fluids, animal tissue, plant, bacteria, fungi, viruses, etc.

In some embodiments, each of the plurality of independent samples can independently comprise at least about 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, 5 µg, 10 µg, 20 µg, 50 µg, 100 µg, 200 µg, 500 µg, or 1000 µg, or more of nucleic acid material. In some embodiments, each of the plurality of independent samples can independently comprise less than about 1 ng, 2 ng, 5 ng, 10 ng, 20 ng, 30 ng, 40 ng, 50 ng, 75 ng, 100 ng, 150 ng, 200 ng, 250 ng, 300 ng, 400 ng, 500 ng, 1 µg, 1.5 µg, 2 µg, 5 µg, 10 µg, 20 µg, 50 µg, 100 µg, 200 µg, 500 µg, or 1000 µg, or more of nucleic acid.

In some embodiments, end repair is performed to generate blunt end 5' phosphorylated nucleic acid ends using commercial kits, such as those available from Epicentre Biotechnologies (Madison, Wis.).

An adapter oligonucleotide includes any oligonucleotide having a sequence, at least a portion of which is known, that can be joined to a target polynucleotide. Adapter oligonucleotides can comprise DNA, RNA, nucleotide analogues, non-canonical nucleotides, labeled nucleotides, modified nucleotides, or combinations thereof. Adapter oligonucleotides can be single-stranded, double-stranded, or partial duplex. In general, a partial-duplex adapter comprises one or more single-stranded regions and one or more double-stranded regions. Double-stranded adapters can comprise two separate oligonucleotides hybridized to one another (also referred to as an "oligonucleotide duplex"), and hybridization may leave one or more blunt ends, one or more 3' overhangs, one or more 5' overhangs, one or more bulges resulting from mismatched and/or unpaired nucleotides, or any combination of these. In some embodiments, a single-stranded adapter comprises two or more sequences that are able to hybridize with one another. When two such hybridizable sequences are contained in a single-stranded adapter, hybridization yields a hairpin structure (hairpin adapter). When two hybridized regions of an adapter are separated from one another by a non-hybridized region, a "bubble" structure results. Adapters comprising a bubble structure can consist of a single adapter oligonucleotide comprising internal hybridizations, or may comprise two or more adapter oligonucleotides hybridized to one another. Internal sequence hybridization, such as between two hybridizable sequences in an adapter, can produce a double-stranded structure in a single-stranded adapter oligonucleotide. Adapters of different kinds can be used in combination, such as a hairpin adapter and a double-stranded adapter, or adapters of different sequences. Hybridizable sequences in a hairpin adapter may or may not include one or both ends of the oligonucleotide. When neither of the ends are included in the hybridizable sequences, both ends are "free" or "overhanging." When only one end is hybridizable to another sequence in the adapter, the other end forms an overhang, such as a 3' overhang or a 5' overhang. When both the 5'-terminal nucleotide and the 3'-terminal nucleotide are included in the hybridizable sequences, such that the 5'-terminal nucleotide and the 3'-terminal nucleotide are complementary and hybridize with one another, the end is referred to as "blunt." Different adapters can be joined to target polynucleotides in sequential reactions or simultaneously. For example, the first and second adapters can be added to the same reaction. Adapters can be manipulated prior to combining with target polynucleotides. For example, terminal phosphates can be added or removed.

Adapters can contain one or more of a variety of sequence elements, including but not limited to, one or more amplification primer annealing sequences or complements thereof, one or more sequencing primer annealing sequences or complements thereof, one or more barcode sequences, one or more common sequences shared among multiple different adapters or subsets of different adapters, one or more restriction enzyme recognition sites, one or more overhangs complementary to one or more target polynucleotide overhangs, one or more probe binding sites (e.g. for attachment to a sequencing platform, such as a flow cell for massive parallel sequencing, such as developed by Illumina, Inc.), one or more random or near-random sequences (e.g. one or more nucleotides selected at random from a set of two or more different nucleotides at one or more positions, with each of the different nucleotides selected at one or more positions represented in a pool of adapters comprising the random sequence), and combinations thereof. Two or more sequence elements can be non-adjacent to one another (e.g. separated by one or more nucleotides), adjacent to one another, partially overlapping, or completely overlapping. For example, an amplification primer annealing sequence can also serve as a sequencing primer annealing sequence. Sequence elements can be located at or near the 3' end, at or near the 5' end, or in the interior of the adapter oligonucleotide. When an adapter oligonucleotide is capable of forming secondary structure, such as a hairpin, sequence elements can be located partially or completely outside the secondary structure, partially or completely inside the secondary structure, or in between sequences participating in the secondary structure. For example, when an adapter oligonucleotide comprises a hairpin structure, sequence elements can be located partially or completely inside or outside the hybridizable sequences (the "stem"), including in the sequence between the hybridizable sequences (the "loop"). In some embodiments, the first adapter oligonucleotides in a plurality of first adapter oligonucleotides having different barcode sequences comprise a sequence element common among all first adapter oligonucleotides in the plurality. In some embodiments, all second adapter oligonucleotides comprise a sequence element common among all second adapter oligonucleotides that is different from the common sequence element shared by the first adapter oligonucleotides. A difference in sequence elements can be any such that at least a portion of different adapters do not completely align, for example, due to changes in sequence length, deletion or insertion of one or more nucleotides, or a change in the nucleotide composition at one or more nucleotide positions (such as a base change or base modification). In some embodiments, an adapter oligonucleotide comprises a 5' overhang, a 3' overhang, or both that is complementary to one or more target polynucleotides. Complementary overhangs can be one or more nucleotides in length, including but not limited to 1, 2, 3, 4, 5, 6, 7, 8, 9, 10, 11, 12, 13, 14, 15, or more nucleotides in length. For example, the complementary overhangs can be about 1, 2, 3, 4, 5 or 6 nucleotides in length. Complementary overhangs may comprise a fixed sequence. Complementary overhangs may comprise a random sequence of one or more nucleotides, such that one or more nucleotides are selected at random from a set of two or more different nucleotides at one or more positions, with each of the different nucleotides selected at one or more positions represented in a pool of adapters with complementary overhangs comprising the random sequence. In some embodiments, an adapter overhang is complementary to a target polynucleotide overhang produced by restriction endonuclease digestion. In some embodiments, an adapter overhang consists of an adenine or a thymine.

Adapter oligonucleotides can have any suitable length, at least sufficient to accommodate the one or more sequence elements of which they are comprised. In some embodiments, adapters are about, less than about, or more than about 10, 15, 20, 25, 30, 35, 40, 45, 50, 55, 60, 65, 70, 75, 80, 90, 100, 200, or more nucleotides in length. In some examples, the adaptors can be about 10 to about 50 nucleotides in length. In further examples, the adaptors can be about 20 to about 40 nucleotides in length.

As used herein, the term "barcode" refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes can be at least 3, 4, 5, 6, 7, 8, 9, 10, 11, 12, 13, 14, 15, or more nucleotides in length. For example, barcodes can be at least 10, 11, 12, 13, 14, or 15 nucleotides in length. In some embodiments, barcodes can be shorter than 10, 9, 8, 7, 6, 5, or 4 nucleotides in length. For example, barcodes can be shorter than 10 nucleotides in length. In some embodiments, barcodes associated with some polynucleotides are of different length than barcodes associated with other polynucleotides. In general, barcodes are of sufficient length and comprise sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some examples, 1, 2 or 3 nucleotides can be mutated, inserted and/or deleted. In some embodiments, each barcode in a plurality of barcodes differ from every other barcode in the plurality at least two nucleotide positions, such as at least 2, 3, 4, 5, 6, 7, 8, 9, 10, or more positions. In some examples, each barcode can differ from every other barcode by in at least 2, 3, 4 or 5 positions. In some embodiments, both a first site and a second site comprise at least one of a plurality of barcode sequences. In some embodiments, barcodes for second sites are selected independently from barcodes for first adapter oligonucleotides. In some embodiments, first sites and second sites having barcodes are paired, such that sequences of the pair comprise the same or different one or more barcodes. In some embodiments, the methods of the disclosure further comprise identifying the sample from which a target polynucleotide is derived based on a barcode sequence to which the target polynucleotide is joined. In general, a barcode may comprise a nucleic acid sequence that when joined to a target polynucleotide serves as an identifier of the sample from which the target polynucleotide was derived.

In eukaryotes, genomic DNA is packed into chromatin to consist as chromosomes within the nucleus. The basic structural unit of chromatin is the nucleosome, which consists of 146 base pairs (bp) of DNA wrapped around a histone octamer. The histone octamer consists of two copies each of the core histone H2A-H2B dimers and H3-H4 dimers. Nucleosomes are regularly spaced along the DNA in what is commonly referred to as "beads on a string".

The assembly of core histones and DNA into nucleosomes is mediated by chaperone proteins and associated assembly factors. Nearly all of these factors are core histone-binding proteins. Some of the histone chaperones, such as nucleosome assembly protein-1 (NAP-1), exhibit a preference for binding to histones H3 and H4. It has also been observed that newly synthesized histones are acetylated and then subsequently deacetylated after assembly into chromatin. The factors that mediate histone acetylation or deacetylation therefore play an important role in the chromatin assembly process.

In general, two in vitro methods have been developed for reconstituting or assembling chromatin. One method is ATP-independent, while the second is ATP-dependent. The ATP-independent method for reconstituting chromatin involves the DNA and core histones plus either a protein like NAP-1 or salt to act as a histone chaperone. This method results in a random arrangement of histones on the DNA that does not accurately mimic the native core nucleosome particle in the cell. These particles are often referred to as mononucleosomes because they are not regularly ordered, extended nucleosome arrays and the DNA sequence used is usually not longer than 250 bp (Kundu, T. K. et al., Mol. Cell 6: 551-561, 2000). To generate an extended array of ordered nucleosomes on a greater length of DNA sequence, the chromatin must be assembled through an ATP-dependent process.

The ATP-dependent assembly of periodic nucleosome arrays, which are similar to those seen in native chromatin, requires the DNA sequence, core histone particles, a chaperone protein and ATP-utilizing chromatin assembly factors. ACF (ATP-utilizing chromatin assembly and remodeling factor) or RSF (remodeling and spacing factor) are two widely researched assembly factors that are used to generate extended ordered arrays of nucleosomes into chromatin in vitro (Fyodorov, D. V., and Kadonaga, J. T. Method Enzymol. 371: 499-515, 2003; Kundu, T. K. et al. Mol. Cell 6: 551-561, 2000).

In particular embodiments, the methods of the disclosure can be easily applied to any type of fragmented double stranded DNA including but not limited to, for example, free DNA isolated from plasma, serum, and/or urine; apoptotic DNA from cells and/or tissues; DNA fragmented enzymatically in vitro (for example, by DNase I and/or restriction endonuclease); and/or DNA fragmented by mechanical forces (hydro-shear, sonication, nebulization, etc.).

Nucleic acid obtained from biological samples can be fragmented to produce suitable fragments for analysis. Template nucleic acids may be fragmented or sheared to desired length, using a variety of mechanical, chemical and/or enzymatic methods. DNA may be randomly sheared via sonication, e.g. Covaris method, brief exposure to a DNase, or using a mixture of one or more restriction enzymes, or a transposase or nicking enzyme. RNA may be fragmented by brief exposure to an RNase, heat plus magnesium, or by shearing. The RNA may be converted to cDNA. If fragmentation is employed, the RNA may be converted to cDNA before or after fragmentation. In some embodiments, nucleic acid from a biological sample is fragmented by sonication. In other embodiments, nucleic acid is fragmented by a hydroshear instrument. Generally, individual nucleic acid template molecules can be from about 2 kb bases to about 40 kb. In various embodiments, nucleic acids can be about 6 kb-10 kb fragments. Nucleic acid molecules may be single-stranded, double-stranded, or double-stranded with single-stranded regions (for example, stem- and loop-structures).

In some embodiments, cross-linked DNA molecules may be subjected to a size selection step. Size selection of the nucleic acids may be performed to cross-linked DNA molecules below or above a certain size. Size selection may further be affected by the frequency of cross-links and/or by the fragmentation method, for example by choosing a frequent or rare cutter restriction enzyme. In some embodiments, a composition may be prepared comprising cross-linking a DNA molecule in the range of about 1 kb to 5 Mb, about 5 kb to 5 Mb, about 5 kB to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 150 kb to 1 Mb).

In some embodiments, sample polynucleotides are fragmented into a population of fragmented DNA molecules of one or more specific size range(s). In some embodiments, fragments can be generated from at least about 1, about 2, about 5, about 10, about 20, about 50, about 100, about 200, about 500, about 1000, about 2000, about 5000, about 10,000, about 20,000, about 50,000, about 100,000, about 200,000, about 500,000, about 1,000,000, about 2,000,000, about 5,000,000, about 10,000,000, or more genome-equivalents of starting DNA. Fragmentation may be accomplished by methods known in the art, including chemical, enzymatic, and mechanical fragmentation. In some embodiments, the fragments have an average length from about 10 to about 10,000, about 20,000, about 30,000, about 40,000, about 50,000, about 60,000, about 70,000, about 80,000, about 90,000, about 100,000, about 150,000, about 200,000, about 300,000, about 400,000, about 500,000, about 600,000, about 700,000, about 800,000, about 900,000, about 1,000,000, about 2,000,000, about 5,000,000, about 10,000,000, or more nucleotides. In some embodiments, the fragments have an average length from about 1 kb to about 10 Mb. In some embodiments, the fragments have an average length from about 1 kb to 5 Mb, about 5 kb to 5 Mb, about 5 kB to 2 Mb, about 10 kb to 2 Mb, about 10 kb to 1 Mb, about 20 kb to 1 Mb about 20 kb to 500 kb, about 50 kb to 500 kb, about 50 kb to 200 kb, about 60 kb to 200 kb, about 60 kb to 150 kb, about 80 kb to 150 kb, about 80 kb to 120 kb, or about 100 kb to 120 kb, or any range bounded by any of these values (e.g. about 60 to 120 kb). In some embodiments, the fragments have an average length less than about 10 Mb, less than about 5 Mb, less than about 1 Mb, less than about 500 kb, less than about 200 kb, less than about 100 kb, or less than about 50 kb. In other embodiments, the fragments have an average length more than about 5 kb, more than about 10 kb, more than about 50 kb, more than about 100 kb, more than about 200 kb, more than about 500 kb, more than about 1 Mb, more than about 5 Mb, or more than about 10 Mb. In some embodiments, the fragmentation is accomplished mechanically comprising subjection sample DNA molecules to acoustic sonication. In some embodiments, the fragmentation comprises treating the sample DNA molecules with one or more enzymes under conditions suitable for the one or more enzymes to generate double-stranded nucleic acid breaks. Examples of enzymes useful in the generation of DNA fragments include sequence specific and non-sequence specific nucleases. Non-limiting examples of nucleases include DNase I, Fragmentase, restriction endonucleases, variants thereof, and combinations thereof. For example, digestion with DNase I can induce random double-stranded breaks in DNA in the absence of $Mg^{++}$ and in the presence of $Mn^{++}$. In some embodiments, fragmentation comprises treating the sample DNA molecules with one or more restriction endonucleases. Fragmentation can produce fragments having 5' overhangs, 3' overhangs, blunt ends, or a combination thereof. In some embodiments, such as when fragmentation comprises the use of one or more restriction endonucleases, cleavage of sample DNA molecules leaves overhangs having a predictable sequence. In some embodiments, the method includes the step of size selecting the fragments via standard methods such as column purification or isolation from an agarose gel.

In some embodiments, the 5' and/or 3' end nucleotide sequences of fragmented DNA are not modified prior to ligation. For example, fragmentation by a restriction endonuclease can be used to leave a predictable overhang, followed by ligation with a nucleic acid end comprising an overhang complementary to the predictable overhang on a DNA fragment. In another example, cleavage by an enzyme that leaves a predictable blunt end can be followed by ligation of blunt-ended DNA fragments to nucleic acids, such as adapters, oligonucleotides, or polynucleotides, comprising a blunt end. In some embodiments, the fragmented DNA molecules are blunt-end polished (or "end repaired") to produce DNA fragments having blunt ends, prior to being joined to adapters. The blunt-end polishing step may be accomplished by incubation with a suitable enzyme, such as a DNA polymerase that has both 3' to 5' exonuclease activity and 5' to 3' polymerase activity, for example T4 polymerase. In some embodiments, end repair can be followed by an addition of 1, 2, 3, 4, 5, 6, 7, 8, 9, 10, 11, 12, 13, 14, 15, 16, 17, 18, 19, 20 or more nucleotides, such as one or more adenine, one or more thymine, one or more guanine, or one or more cytosine, to produce an overhang. For example, the end pair can be followed by an addition of 1, 2, 3, 4, 5, or 6 nucleotides. DNA fragments having an overhang can be joined to one or more nucleic acids, such as oligonucleotides, adapter oligonucleotides, or polynucleotides, having a complementary overhang, such as in a ligation reaction. For example, a single adenine can be added the 3' ends of end repaired DNA fragments using a template independent polymerase, followed by ligation to one or more adapters each having a thymine at a 3' end. In some embodiments, nucleic acid, such as oligonucleotides or polynucleotides can be joined to blunt end double-stranded DNA molecules which have been modified by extension of the 3' end with one or more nucleotides followed by 5' phosphorylation. In some cases, extension of the 3' end may be performed with a polymerase such as, Klenow polymerase or any of the suitable polymerases provided herein, or by use of a terminal deoxynucleotide transferase, in the presence of one or more dNTPs in a suitable buffer that can contain magnesium. In some embodiments, target polynucleotides having blunt ends are joined to one or more adapters comprising a blunt end. Phosphorylation of 5' ends of DNA fragment molecules may be performed for example with T4 polynucleotide kinase in a suitable buffer containing ATP and magnesium. The fragmented DNA molecules may optionally be treated to dephosphorylate 5' ends or 3' ends, for example, by using enzymes known in the art, such as phosphatases.

The terms "connecting", "joining" and "ligation" as used herein, with respect to two polynucleotides, such as an adapter oligonucleotide and a target polynucleotide, refers to the covalent attachment of two separate DNA segments to produce a single larger polynucleotide with a contiguous backbone. Methods for joining two DNA segments are known in the art, and include without limitation, enzymatic and non-enzymatic (e.g. chemical) methods. Examples of ligation reactions that are non-enzymatic include the non-enzymatic ligation techniques described in U.S. Pat. Nos. 5,780,613 and 5,476,930, which are herein incorporated by reference. In some embodiments, an adapter oligonucleotide is joined to a target polynucleotide by a ligase, for example a DNA ligase or RNA ligase. Multiple ligases, each having characterized reaction conditions, are known in the art, and include, without limitation NAD$^+$-dependent ligases including tRNA ligase, Tag DNA ligase, *Thermus filiformis* DNA ligase, *Escherichia coli* DNA ligase, Tth DNA ligase, *Thermus scotoductus* DNA ligase (I and II), thermostable ligase, Ampligase thermostable DNA ligase, VanC-type ligase, 9° N DNA Ligase, Tsp DNA ligase, and novel ligases discovered by bioprospecting; ATP-dependent ligases including T4 RNA ligase, T4 DNA ligase T3 DNA ligase, T7 DNA Ligase, Pfu DNA ligase DNA ligase 1, DNA ligase III, DNA ligase IV, and novel ligases discovered by bioprospecting; and wild-type, mutant isoforms, and genetically engineered variants thereof.

Ligation can be between DNA segments having hybridizable sequences, such as complementary overhangs. Ligation can also be between two blunt ends. Generally, a 5' phosphate is utilized in a ligation reaction. The 5' phosphate can be provided by the target polynucleotide, the adapter oligonucleotide, or both. 5' phosphates can be added to or removed from DNA segments to be joined, as needed. Methods for the addition or removal of 5' phosphates are known in the art, and include without limitation enzymatic and chemical processes. Enzymes useful in the addition and/or removal of 5' phosphates include kinases, phosphatases, and polymerases. In some embodiments, both of the two ends joined in a ligation reaction (e.g. an adapter end and a target polynucleotide end) provide a 5' phosphate, such that two covalent linkages are made in joining the two ends. In some embodiments, only one of the two ends joined in a ligation reaction (e.g. only one of an adapter end and a target polynucleotide end) provides a 5' phosphate, such that only one covalent linkage is made in joining the two ends.

In some embodiments, only one strand at one or both ends of a target polynucleotide is joined to an adapter oligonucleotide. In some embodiments, both strands at one or both ends of a target polynucleotide al, joined to an adapter oligonucleotide. In some embodiments, 3' phosphates are removed prior to ligation. In some embodiments, an adapter oligonucleotide is added to both ends of a target polynucleotide, wherein one or both strands at each end are joined to one or more adapter oligonucleotides. When both strands at both ends are joined to an adapter oligonucleotide, joining can be followed by a cleavage reaction that leaves a 5' overhang that can serve as a template for the extension of the corresponding 3' end, which 3' end may or may not include one or more nucleotides derived from the adapter oligonucleotide. In some embodiments, a target polynucleotide is joined to a first adapter oligonucleotide on one end and a second adapter oligonucleotide on the other end. In some embodiments, two ends of a target polynucleotide are joined to the opposite ends of a single adapter oligonucleotide. In some embodiments, the target polynucleotide and the adapter oligonucleotide to which it is joined comprise blunt ends. In some embodiments, separate ligation reactions can be carried out for each sample, using a different first adapter oligonucleotide comprising at least one barcode sequence for each sample, such that no barcode sequence is joined to the target polynucleotides of more than one sample. A DNA segment or a target polynucleotide that has art adapter oligonucleotide joined to it is considered "tagged" by the joined adapter.

In some cases, the ligation reaction can be performed at a DNA segment or target polynucleotide concentration of about 0.1 ng/µL, about 0.2 ng/µL, about 0.3 ng/µL, about 0.4 ng/µL, about 0.5 ng/µL, about 0.6 ng/µL, about 0.7 ng/µL, about 0.8 ng/µL, about 0.9 ng/µL, about 1.0 ng/µL, about 1.2 ng/µL, about 1.4 ng/µL, about 1.6 ng/µL, about 1.8 ng/µL, about 2.0 ng/µL, about 2.5 ng/µL, about 3.0 ng/µL, about 3.5 ng/µL, about 4.0 ng/µL, about 4.5 ng/µL, about 5.0 ng/µL, about 6.0 ng/µL, about 7.0 ng/µL, about 8.0 ng/µL, about 9.0 ng/µL, about 10 ng/µL, about 15 ng/µL, about 20 ng/µL, about 30 ng/µL, about 40 ng/µL, about 50 ng/µL, about 60 ng/µL, about 70 ng/µL, about 80 ng/µL, about 90 ng/µL, about 100 ng/µL, about 150 ng/µL, about 200 ng/µL, about 300 ng/µL, about 400 ng/µL, about 500 ng/µL, about 600 ng/µL, about 800 ng/µL, or about 1000 ng/µL. For example, the ligation can be performed at a DNA segment or target polynucleotide concentration of about 100 ng/µL, about 150 ng/µL, about 200 ng/µL, about 300 ng/µL, about 400 ng/µL, or about 500 ng/µL.

In some cases, the ligation reaction can be performed at a DNA segment or target polynucleotide concentration of about 0.1 to 1000 ng/µL, about 1 to 1000 ng/µL, about 1 to 800 ng/µL, about 10 to 800 ng/µL, about 10 to 600 ng/µL, about 100 to 600 ng/µL, or about 100 to 500 ng/µL.

In some cases, the ligation reaction can be performed for more than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. In other cases, the ligation reaction can be performed for less than about 5 minutes, about 10 minutes, about 20 minutes, about 30 minutes, about 40 minutes, about 50 minutes, about 60 minutes, about 90 minutes, about 2 hours, about 3 hours, about 4 hours, about 5 hours, about 6 hours, about 8 hours, about 10 hours, about 12 hours, about 18 hours, about 24 hours, about 36 hours, about 48 hours, or about 96 hours. For example, the ligation reaction can be performed for about 30 minutes to about 90 minutes. In some embodiments, joining of an adapter to a target polynucleotide produces a joined product polynucleotide having a 3' overhang comprising a nucleotide sequence derived from the adapter.

In some embodiments, after joining at least one adapter oligonucleotide to a target polynucleotide, the 3' end of one or more target polynucleotides is extended using the one or more joined adapter oligonucleotides as template. For example, an adapter comprising two hybridized oligonucleotides that is joined to only the 5' end of a target polynucleotide allows for the extension of the unjoined 3' end of the target using the joined strand of the adapter as template, concurrently with or following displacement of the unjoined strand. Both strands of an adapter comprising two hybridized oligonucleotides may be joined to target polynucleotide such that the joined product has a 5' overhang, and the complementary 3' end can be extended using the 5' overhang as template. As a further example, a hairpin adapter oligonucleotide can be joined the 5' end of a target polynucleotide. In some embodiments, the 3' end of the target polynucleotide that is extended comprises one or more nucleotides from an adapter oligonucleotide. For target polynucleotides to which adapters are joined on both ends, extension can be carried out for both 3' ends of a double-stranded target polynucleotide having 5' overhangs. This 3' end extension, or "fill-in" reaction, generates a complementary sequence, or "complement," to the adapter oligonucleotide template that is hybridized to the template, thus filling in the 5' overhang to produce a double-stranded sequence region. Where both ends of a double-stranded target polynucleotide have 5 overhangs that are filled in by extension of the complementary strands' 3' ends, the product is completely double-stranded. Extension can be carried out by any suitable polymerase known in the art, such as a DNP polymerase, many of which are commercially available, DNA polymerases can comprise DNA-dependent DNA polymerase activity, RNA-dependent DNA polymerase activity, or DNA-dependent and RNA-dependent DNA polymerase activity. DNA polymerases can be thermostable or non-thermostable. Examples of DNA polymerases include, but are not limited to, Taq polymerase, Tth polymerase, Tli polymerase, Pfu polymerase, Pfutubo polymerase, Pyrobest polymerase, Pwo polymerase, KOD polymerase, Bst polymerase, Sac polymerase, Sso polymerase, Poc polymerase, Pab polymerase, Mth polymerase, Pho polymerase, ES4 polymerase, VENT polymerase, DEEPVENT polymerase, EX-Taq polymerase, LA-Taq polymerase, Expand polymerases, Platinum Taq polymerases, Hi-Fi polymerase, Tbr polymerase, Tfl polymerase, Tru polymerase, Tac polymerase, Tne polymerase, Tma polymerase, Tih polymerase, Tfi polymerase, Klenow fragment, and variants, modified products and derivatives thereof 3' end extension can be performed before or after pooling of target polynucleotides from independent samples.

In certain embodiments, the disclosure provides methods for the enrichment of a target nucleic acids and analysis of the target nucleic acids. In some cases, the methods for enrichment is in a solution based format. In some cases, the target nucleic acid can be labeled with a labeling agent. In other cases, the target nucleic acid can be crosslinked to one or more association molecules that are labeled with a labeling agent. Examples of labeling agents include but are not limited to biotin, polyhistidine tags, and chemical tags (e.g. alkyne and azide derivatives used in Click Chemistry methods). Further, the labeled target nucleic acid can be captured and thereby enriched by using a capturing agent. The capturing agent can be streptavidin and/or avidin, an antibody, a chemical moiety (e.g. alkyne, azide), and any biological, chemical, physical, or enzymatic agents used for affinity purification known in the art.

In some cases, immobilized or non-immobilized nucleic acid probes can be used to capture the target nucleic acids. For example, the target nucleic acids can be enriched from a sample by hybridization to the probes on a solid support or in solution. In some examples, the sample can be a genomic sample. In some examples, the probes can be an amplicon. The amplicon can comprise a predetermined sequence. Further, the hybridized target nucleic acids can be washed and/or eluted off of the probes. The target nucleic acid can be a DNA, RNA, cDNA, or mRNA molecule.

In some cases, the enrichment method can comprise contacting the sample comprising the target nucleic acid to the probes and binding the target nucleic acid to a solid support. In some cases, the sample can be fragmented using chemical, physical or enzymatic methods to yield the target nucleic acids. In some cases, the probes can be specifically hybridized to the target nucleic acids. In some cases, the target nucleic acids can have an average size of about 50 to 5000, about 50 to 2000, about 100 to 2000, about 100 to 1000, about 200 to 1000, about 200 to 800, or about 300 to 800, about 300 to 600, or about 400 to 600 nucleotide residues. The target nucleic acids can be further separated from the unbound nucleic acids in the sample. The solid support can be washed and/or eluted to provide the enriched target nucleic acids. In some examples, the enrichment steps can be repeated for about 1, 2, 3, 4, 5, 6, 7, 8, 9, or 10 times. For example, the enrichment steps can be repeated for about 1, 2, or 3 times.

In some cases, the enrichment method can comprise providing probe derived amplicons wherein said probes for amplification are attached to a solid support. The solid support can comprise support immobilized nucleic acid probes to capture specific target nucleic acid from a sample. The probe derived amplicons can hybridize to the target nucleic acids. Following hybridization to the probe amplicons, the target nucleic acids a the sample can be enriched by capturing (e.g., via capturing agents as biotin, antibodies, etc.) and ashing and/or eluting the hybridized target nucleic acids from the captured probes (FIG. 4). The target nucleic acid sequence (s) may be further amplified using, for example, PCR methods to produce an amplified pool of enriched PCR products.

In some cases, the solid support can be a microarray, a slide, a chip, a microwell, a column, a tube, a particle or a bead. In some examples, the solid support can be coated with streptavidin and/or avidin. In other examples, the solid support can be coated with an antibody. Further, the solid support can comprise a glass, metal, ceramic or polymeric material. In some embodiments, the solid support can be a nucleic acid microarray (e.g. a DNA microarray). In other embodiments, the solid support can be a paramagnetic bead.

In some cases, the enrichment method can comprise digestion with a secondary restriction enzyme, self-ligation (e.g. self-circularization), and re-digestion with the original restriction enzyme. In particular examples, only the ligation products will be linearized and available for adapter-ligation and sequencing. In other cases, the ligation junction sequence itself can be used for hybridization based enrichment using a bait-probe complimentary to the junction sequence.

In particular embodiments, the disclosure provides methods for amplifying the enriched DNA. In some cases, the enriched DNA is a read-pair. The read-pair can be obtained by the methods of the present disclosure.

In some embodiments, the one or more amplification and/or replication steps are used for the preparation of a library to be sequenced. Any amplification method known in the art may be used. Examples of amplification techniques that can be used include, but are not limited to, quantitative PCR, quantitative fluorescent PCR (QF-PCR), multiplex fluorescent PCR (MF-PCR), real time PCR (RTPCR), single cell PCR, restriction fragment length polymorphism PCR (PCR-RFLP), PCK-RFLPIRT-PCR-IRFLP, hot start PCR, nested PCR, in situ polonony PCR, in situ rolling circle amplification (RCA), bridge PCR, ligation mediated PCR, Qb replicase amplification, inverse PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

In particular embodiments, PCR is used to amplify DNA molecules after they are dispensed into individual partitions. In some cases, one or more specific priming sequences within amplification adapters are utilized for PCR amplification. The amplification adapters may be ligated to fragmented DNA molecules before or after dispensing into individual partitions. Polynucleotides comprising amplification adapters with suitable priming sequences on both ends can be PCR amplified exponentially. Polynucleotides with only one suitable priming sequence due to, for example, imperfect ligation efficiency of amplification adapters comprising priming sequences, may only undergo linear amplification. Further, polynucleotides can be eliminated from amplification, for example PCR amplification, all together, if no adapters comprising suitable priming sequences are ligated. In some embodiments, the number of PCR cycles vary between 10-30, but can be as low as 9, 8, 7, 6, 5, 4, 3, 2 or less or as high as 40, 45, 50, 55, 60 or more. As a result, exponentially amplifiable fragments carrying amplification adapters with a suitable priming sequence can be present in much higher (1000 fold or more) concentration compared to linearly amplifiable or un-amplifiable fragments, after a PCR amplification. Benefits of PCR, as compared to whole genome amplification techniques (such as amplification with randomized primers or Multiple Displacement Amplification using phi29 polymerase) include, but are not limited to a more uniform relative sequence coverage—as each fragment can be copied at most once per cycle and as the amplification is controlled by thermocycling program, a substantially lower rate of forming chimeric molecules than for example MDA (Lasken et al., 2007, BMC Biotechnology)—as chimeric molecules pose significant challenges for accurate sequence assembly by presenting nonbiological sequences in the assembly graph, which may result in higher rate of misassemblies or highly ambiguous and fragmented assembly, reduced sequence specific biases that may result from binding of randomized primers commonly used in MDA versus using specific priming sites with a specific sequence, a higher reproducibility in the amount of final amplified DNA product, which can be controlled by selection of the number of PCR cycles, and a higher fidelity in replication with the polymerases that are commonly used in PCR as compared to common whole genome amplification techniques known in the art.

In some embodiments, the fill-in reaction is followed by or performed as part of amplification of one or more target polynucleotides using a first primer and a second primer, wherein the first primer comprises a sequence that is hybridizable to at least a portion of the complement of one or more of the first adapter oligonucleotides, and further wherein the second primer comprises a sequence that is hybridizable to at least a portion of the complement of one or more of the second adapter oligonucleotides. Each of the first and second primers may be of any suitable length, such as about, less than about, or more than about 10, 15, 20, 25, 30, 35, 40, 45, 50, 55, 60, 65, 70, 75, 80, 90, 100, or more nucleotides, any portion or all of which may be complementary to the corresponding target sequence (e.g. about, less than about, or more than about 5, 10, 15, 20, 25, 30, 35, 40, 45, 50, or more nucleotides). For example, about 10 to 50 nucleotides can be complementary to the corresponding target sequence.

"Amplification" refers to any process by which the copy number of a target sequence is increased. In some cases, replication reaction may produce only a complementary copy/replica of a polynucleotide. Methods for primer-directed amplification of target polynucleotides are known in the art, and include without limitation, methods based on the polymerase chain reaction (PCR). Conditions favorable to the amplification of target sequences by PCR are known in art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, and others, some or all of which can be altered. In general, PCR involves the steps of denaturation of the target to be amplified (if double stranded), hybridization of one or more primers to the target, and extension of the primers by a DNA polymerase, with the steps repeated (or "cycled") in order to amplify the target sequence. Steps in this process can be optimized for various outcomes, such as to enhance yield, decrease the formation of spurious products, and/or increase or decrease specificity of primer annealing. Methods of optimization are well known in the art and include adjustments to the type or amount of elements in the amplification reaction and/or to the conditions of a given step in the process, such as temperature at a particular step, duration of a particular step, and/or number of cycles.

In some embodiments, an amplification reaction can comprise at least about 5, 10, 15, 20, 25, 30, 35, 40, 50, 60, 70, 80, 90, 100, 150, 200 or more cycles. In some examples, an amplification reaction can comprise at least about 20, 25, 30, 35 or 40 cycles. In some embodiments, an amplification reaction comprises no more than about 5, 10, 15, 20, 25, 35, 40, 50, 60, 70, 80, 90, 100, 150, 200 or more cycles. Cycles can contain any number of steps, such as 1, 2, 3, 4, 5, 6, 7, 8, 9, 10 or more steps. Steps can comprise any temperature or gradient of temperatures, suitable for achieving the purpose of the given step, including but not limited to, 3' end extension (e.g. adapter fill-in), primer annealing, primer extension, and strand denaturation. Steps can be of any duration, including but not limited to about, less than about, or more than about 1, 5, 10, 15, 20, 25, 30, 35, 40, 45, 50, 55, 60, 70, 80, 90, 100, 120, 180, 240, 300, 360, 420, 480, 540, 600, 1200, 1800, or more seconds, including indefinitely until manually interrupted. Cycles of any number comprising different steps can be combined in any order. In some embodiments, different cycles comprising different steps are combined such that the total number of cycles in the combination is about, less that about, or more than about 5, 10, 15, 20, 25, 30, 35, 40, 50, 60, 70, 80, 90, 100, 150, 200 or more cycles. In some embodiments, amplification is performed following the fill-in reaction.

In some embodiments, the amplification reaction can be carried out on at least about 1, 2, 3, 4, 5, 6, 7, 8, 9, 10, 12, 14, 16, 18, 20, 25, 30, 40, 50, 100, 200, 300, 400, 500, 600, 800, 1000 ng of the target DNA molecule. In other embodiments, the amplification reaction can be carried out on less than about 1, 2, 3, 4, 5, 6, 7, 8, 9, 10, 12, 14, 16, 18, 20, 25, 30, 40, 50, 100, 200, 300, 400, 500, 600, 800, 1000 ng of the target DNA molecule.

Amplification can be performed before or after pooling of target polynucleotides from independent samples.

Methods of the disclosure involve determining an amount of amplifiable nucleic acid present in a sample. Any known method may be used to quantify amplifiable nucleic acid, and an exemplary method is the polymerase chain reaction (PCR), specifically quantitative polymerase chain reaction (qPCR). qPCR is a technique based on the polymerase chain reaction, and is used to amplify and simultaneously quantify a targeted nucleic acid molecule. qPCR allows for both detection and quantification (as absolute number of copies or relative amount when normalized to DNA input or additional normalizing genes) of a specific sequence in a DNA sample. The procedure follows the general principle of polymerase chain reaction, with the additional feature that the amplified DNA is quantified as it accumulates in the reaction in real time after each amplification cycle. QPCR is described, for example, in Kurnit et al. (U.S. Pat. No. 6,033,854), Wang et al. (U.S. Pat. Nos. 5,567,583 and 5,348,853), Ma et al. (The Journal of American Science, 2(3), 2006), Heid et al. (Genome Research 986-994, 1996), Sambrook and Russell (Quantitative PCR, Cold Spring Harbor Protocols, 2006), and Higuchi (U.S. Pat. Nos. 6,171, 785 and 5,994,056). The contents of these are incorporated by reference herein in their entirety.

Other methods of quantification include use of fluorescent dyes that intercalate with double-stranded DNA, and modified DNA oligonucleotide probes that fluoresce when hybridized with a complementary DNA. These methods can be broadly used but are also specifically adapted to real-time PCR as described in further detail as an example. In the first method, a DNA-binding dye binds to all double-stranded (ds)DNA in PCR, resulting in fluorescence of the dye. An increase in DNA product during PCR therefore leads to an increase in fluorescence intensity and is measured at each cycle, thus allowing DNA concentrations to be quantified. The reaction is prepared similarly to a standard PCR reaction, with the addition of fluorescent (ds)DNA dye. The reaction is run in a thermocycler, and after each cycle, the levels of fluorescence are measured with a detector; the dye only fluoresces when bound to the (ds)DNA (i.e., the PCR product). With reference to a standard dilution, the (ds)DNA concentration in the PCR can be determined. Like other real-time PCR methods, the values obtained do not have absolute units associated with it. A comparison of a measured DNA/RNA sample to a standard dilution gives a fraction or ratio of the sample relative to the standard, allowing relative comparisons between different tissues or experimental conditions. To ensure accuracy in the quantification and/or expression of a target gene can be normalized with respect to a stably expressed gene. Copy numbers of unknown genes can similarly be normalized relative to genes of known copy number.

The second method uses a sequence-specific RNA or DNA-based probe to quantify only the DNA containing a probe sequence; therefore, use of the reporter probe significantly increases specificity, and allows quantification even in the presence of some non-specific DNA amplification. This allows for multiplexing, i.e., assaying for several genes in the same reaction by using specific probes with differently colored labels, provided that all genes are amplified with similar efficiency.

This method is commonly carried out with a DNA-based probe with a fluorescent reporter (e.g. 6-carboxyfluorescein) at one end and a quencher (e.g., 6-carboxy-tetramethylrhodamine) of fluorescence at the opposite end of the probe. The close proximity of the reporter to the quencher prevents detection of its fluorescence. Breakdown of the probe by the 5' to 3' exonuclease activity of a polymerase (e.g., Taq polymerase) breaks the reporter-quencher proximity and thus allows unquenched emission of fluorescence, which can be detected. An increase in the product targeted by the reporter probe at each PCR cycle results in a proportional increase in fluorescence due to breakdown of the probe and release of the reporter. The reaction is prepared similarly to a standard PCR reaction, and the reporter probe is added. As the reaction commences, during the annealing stage of the PCR both probe and primers anneal to the DNA target. Polymerization of a new DNA strand is initiated from the primers, and once the polymerase reaches the probe, its 5'-3'-exonuclease degrades the probe, physically separating the fluorescent reporter from the quencher, resulting in an increase in fluorescence. Fluorescence is detected and measured in a real-time PCR thermocycler, and geometric increase of fluorescence corresponding to exponential increase of the product is used to determine the threshold cycle in each reaction.

Relative concentrations of DNA present during the exponential phase of the reaction are determined by plotting fluorescence against cycle number on a logarithmic scale (so an exponentially increasing quantity will give a straight line). A threshold for detection of fluorescence above background is determined. The cycle at which the fluorescence from a sample crosses the threshold is called the cycle threshold, $C_t$. Since the quantity of DNA doubles every cycle during the exponential phase, relative amounts of DNA can be calculated, e.g. a sample with a $C_t$ of 3 cycles earlier than another has $2^3=8$ times more template. Amounts of nucleic acid (e.g., RNA or DNA) are then determined by comparing the results to a standard curve produced by a real-time PCR of serial dilutions (e.g. undiluted, 1:4, 1:16, 1:64) of a known amount of nucleic acid.

In certain embodiments, the qPCR reaction involves a dual fluorophore approach that takes advantage of fluorescence resonance energy transfer (FRET), e.g., LIGHTCYCLER hybridization probes, where two oligonucleotide probes anneal to the amplicon (e.g. see U.S. Pat. No. 6,174,670). The oligonucleotides are designed to hybridize in a head-to-tail orientation with the fluorophores separated at a distance that is compatible with efficient energy transfer. Other examples of labeled oligonucleotides that are structured to emit a signal when bound to a nucleic acid or incorporated into an extension product include: SCORPIONS probes (e.g., Whitcombe et al., Nature Biotechnology 17:804-807, 1999, and U.S. Pat. No. 6,326,145), Sunrise (or AMPLIFLOUR) primers (e.g., Nazarenko et al., Nuc. Acids Res. 25:2516-2521, 1997, and U.S. Pat. No. 6,117,635), and LUX primers and MOLECULAR BEACONS probes (e.g., Tyagi et al., Nature Biotechnology 14:303-308, 1996 and U.S. Pat. No. 5,989,823).

In other embodiments, a qPCR reaction uses fluorescent Taqman methodology and an instrument capable of measuring fluorescence in real time (e.g., ABI Prism 7700 Sequence Detector). The Taqman reaction uses a hybridization probe labeled with two different fluorescent dyes. One dye is a reporter dye (6-carboxyfluorescein), the other is a quenching dye (6-carboxytetramethylrhodamine). When the probe is intact, fluorescent energy transfer occurs and the reporter dye fluorescent emission is absorbed by the quenching dye. During the extension phase of the PCR cycle, the fluorescent hybridization probe is cleaved by the 5'-3' nucleolytic activity of the DNA polymerase. On cleavage of the probe, the reporter dye emission is no longer transferred efficiently to the quenching dye, resulting in an increase of the reporter dye fluorescent emission spectra. Any nucleic acid quantification method, including real-time methods or single-point detection methods may be used to quantify the amount of nucleic acid in the sample. The detection can be performed several different methodologies (e.g., staining, hybridization with a labeled probe; incorporation of biotinylated primers followed by avidin-enzyme conjugate detection; incorporation of 32P-labeled deoxynucleotide triphosphates, such as dCTP or dATP, into the amplified segment), as well as any other suitable detection method known in the art for nucleic acid quantification. The quantification may or may not include an amplification step.

In some embodiments, the disclosure provides labels for identifying or quantifying the linked DNA segments. In some cases, the linked DNA segments can be labeled in order to assist in downstream applications, such as array hybridization. For example, the linked DNA segments can be labeled using random priming or nick translation.

A wide variety of labels (e.g. reporters) may be used to label the nucleotide sequences described herein, including but not limited to during the amplification step. Suitable labels include radionuclides, enzymes, fluorescent, chemiluminescent, or chromogenic agents as well as ligands, cofactors, inhibitors, magnetic particles and the like. Examples of such labels are included in U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241, which are incorporated by reference in its entirety.

Additional labels include but are not limited to β-galactosidase, invertase, green fluorescent protein, luciferase, chloramphenicol, acetyltransferase, β-glucuronidase, exoglucanase and glucoamylase. Fluorescent labels may also be used, as well as fluorescent reagents specifically synthesized with particular chemical properties. A wide variety of ways to measure fluorescence are available. For example, some fluorescent labels exhibit a change in excitation or emission spectra, some exhibit resonance energy transfer where one fluorescent reporter loses fluorescence, while a second gains in fluorescence, some exhibit a loss (quenching) or appearance of fluorescence, while some report rotational movements.

Further, in order to obtain sufficient material for labeling, multiple amplifications may be pooled, instead of increasing the number of amplification cycles per reaction. Alternatively, labeled nucleotides can be incorporated in to the last cycles of the amplification reaction, e.g. 30 cycles of PCR (no label) +10 cycles of PCR (plus label).

In particular embodiments, the disclosure provides probes that can attach to the linked DNA segments. As used herein, the term "probe" refers to a molecule (e.g., an oligonucleotide, whether occurring naturally as in a purified restriction digest or produced synthetically, recombinantly or by PCR amplification), that is capable of hybridizing to another molecule of interest (e.g., another oligonucleotide). When probes are oligonucleotides they may be single-stranded or double-stranded. Probes are useful in the detection, identification and isolation of particular targets (e.g., gene sequences). In some cases, the probes may be associated with a label so that is detectable in any detection system, including, but not limited to enzyme (e.g., ELISA, as well as enzyme-based histochemical assays), fluorescent, radioactive, and luminescent systems With respect to arrays and microarrays, the term "probe" is used to refer to any hybridizable material that is affixed to the array for the purpose of detecting a nucleotide sequence that has hybridized to said probe. In some cases, the probes can about 10 bp to 500 bp, about 10 bp to 250 bp, about 20 bp to 250 bp, about 20 bp to 200 bp, about 25 bp to 200 bp, about 25 bp to 100 bp, about 30 bp to 100 bp, or about 30 bp to 80 bp. In some cases, the probes can be greater than about 10 bp, about 20 bp, about 30 bp, about 40 bp, about 50 bp, about 60 bp, about 70 bp, about 80 bp, about 90 bp, about 100 bp, about 150 bp, about 200 bp, about 250 bp, about 300 bp, about 400 bp, or about 500 bp in length. For example, the probes can be about 20 to about 50 bp in length. Examples and rationale for probe design can be found in WO95/11995, EP 717,113 and WO97/29212

In some cases, one or more probes can be designed such that they can hybridize close to the sites that are digested by a restriction enzyme. For example, the probe (s) can be within about 10 bp, about 20 bp, about 30 bp, about 40 bp, about 50 bp, about 60 bp, about 70 bp, about 80 bp, about 90 bp, about 100 bp, about 150 bp, about 200 bp, about 250 bp, about: 300 bp, about 400 bp, or about 500 bp of the restriction enzyme recognition site.

In other cases, a single, unique, probe can designed within about 10 bp, about 20 bp, about 30 bp, about 40 bp, about 50 bp, about 60 bp, about 70 bp, about 80 bp, about 90 bp, about 100 bp, about 150 bp, about 200 bp, about 250 bp, about 300 bp, about 400 bp, or about 500 bp at each side of the sites that are digested by the restriction enzyme. The probes can be designed such that they can hybridize at either side of the sites that are digested by the restriction enzyme. For example, a single probe at each side of the primary restriction enzyme recognition site can be used In further cases, 2, 3, 4, 5, 6, 7, 8, or more probes can be designed at each side of the restriction enzyme recognition site, which can then be used to investigate the same ligation event. For example, 2 or 3 probes can be designed at each side of the restriction enzyme recognition site. In some examples, the use of multiple (e.g. 2, 3, 4, 5, 6, 7 or 8 or more) probes per primary restriction enzyme recognition site can be useful to minimize the problem of obtaining false negative results from individual probes.

As used herein, the term "set of probes" refers to a suite or a collection of probes that can hybridize to one or more of the primary restriction enzyme recognition sites for a primary restriction enzyme in a genome.

In some cases, a set of probes can be complementary in sequence to the nucleic acid sequence adjacent to one or more of the primary restriction enzyme recognition sites for a restriction enzyme in genomic DNA. For example, the set of probes can be complementary in sequence the about 10 bp to 500 bp, about 10 bp to 250 bp, about 20 bp to 250 bp, about 20 bp to 200 bp, about 25 bp to 200 bp, about 25 bp to 100 bp, about 30 bp to 100 bp, or about 30 bp to 80 bp nucleotides that are adjacent to one or more of the restriction enzyme recognition sites in genomic DNA. The set of probes may be complementary in sequence to one (e.g. either) side or both sides of the restriction enzyme recognition site. Accordingly, the probes may be complementary in sequence to the nucleic acid sequence adjacent to each side of one or more of the primary restriction enzyme recognition sites in the genomic DNA. Further, the set of probes can be complementary in sequence to the nucleic acid sequence that is less than about 10 bp, about 20 bp, about 30 bp, about 40 bp, about 50 bp, about 60 bp, about 70 bp, about 80 bp, about 90 bp, about 100 bp, about 150 bp, about 200 bp, about 250 bp, about 300 bp, about 400 bp, or about 500 bp from one or more of the primary restriction enzyme recognition sites in genomic DNA In some cases, two or more probes can be designed to be capable of hybridizing to the sequence adjacent to one or more of the restriction enzyme recognition sites in genomic DNA. The probes may overlap or partially overlap.

The probes, array of probes or set of probes can be immobilized on a support. Supports (e.g. solid supports) can be made of a variety of materials-such as glass, silica, plastic, nylon or nitrocellulose. Supports are preferably rigid and have a planar surface. Supports can have from about 1 to 10,000,000 resolved loci. For example, a support can have about 10 to 10,000,000, about 10 to 5,000,000, about 100 to 5,000,000, about 100 to 4,000,000, about 1000 to 4,000,000, about 1000 to 3,000,000, about 10,000 to 3,000,000, about 10,000 to 2,000,000, about 100,000 to 2,000,000, or about 100,000 to 1,000,000 resolved loci. The density of resolved loci can be at least about 10, about 100, about 1000, about 10,000, about 100,000 or about 1,000,000 resolved loci within a square centimeter. In some cases, each resolves loci can be occupied by >95% of a single type of oligonucleotide. In other cases, each resolved locus can be occupied by pooled mixtures of probes or a set of probes. In further cases, some resolved loci are occupied by pooled mixtures of probes or a set of probes, and other resolved loci are occupied by >95% of a single type of oligonucleotide.

In some cases, the number of probes for a given nucleotide sequence on the array can be in large excess to the DNA sample to be hybridized to such array. For example, the array can have about 10, about 100, about 1000, about 10,000, about 100,000, about 1,000,000, about 10,000,000, or about 100,000,000 times the number of probes relative to the amount of DNA in the input sample.

In some cases, an array can have about 10, about 100, about 1000, about 10,000, about 100,000, about 1,000,000, about: 10,000,000, about 100,000,000, or about 1,000,000,000 probes.

Arrays of probes or sets of probes may be synthesized in a step-by-step manner on a support or can be attached in presynthesized form. Or method of synthesis is VLSIPS™ (as described in U.S. Pat. No. 5,143,854 and EP 476,014), which entails the use of light to direct the synthesis of oligonucleotide probes in high-density, miniaturized arrays. Algorithms for design of masks to reduce the number of synthesis cycles are described in U.S. Pat. No. 5,571,639 and U.S. Pat. No. 5,593,839. Arrays can also be synthesized in a combinatorial fashion by delivering monomers to cells of a support by mechanically constrained flowpaths, as described in EP 624,059. Arrays can also be synthesized by spotting reagents on to a support using an ink jet printer (see, for example, EP 728,520).

In some embodiments, the present disclosure provides methods for hybridizing the linked DNA segments onto an array. A "substrate" or an "array" is an intentionally created collection of nucleic acids which can be prepared either synthetically or biosynthetically and screened for biological activity in a variety of different formats (e.g., libraries of soluble molecules; and libraries of oligonucleotides tethered to resin beads, silica chips, or other solid supports). Additionally, the term. "array" includes those libraries of nucleic acids which can be prepared by spotting nucleic acids of essentially any length (e.g., from 1 to about 1000 nucleotide monomers in length) onto a substrate.

Array technology and the various associated techniques and applications are described generally in numerous textbooks and documents. For example, these include Lemieux et al., 1998, *Molecular Breeding* 4, 277-289; Schena and Davis, *Parallel Analysis with Biological Chips.* in *PCR Methods Manual* (eds. M. Innis, D. Gelfand, J. Sninsky); Schena and Davis, 1999, *Genes, Genomes and Chips.* In *DNA Microarrays: A Practical Approach* (ed. M. Schena), Oxford University Press, Oxford, UK, 1999); *The Chipping Forecast* (Nature Genetics special issue; January 1999 Supplement); Mark Schena (Ed.), *Microarray Biochip Technology*, (Eaton Publishing Company); Cortes, 2000, *The Scientist* 14[17]:25; Gwynn and Page, *Microarray analysis: the next revolution in molecular biology, Science,* 1999 Aug. 6; and Eakins and Chu, 1999, *Trends in Biotechnology*, 17, 217-218.

In general, any library may be arranged in an orderly manner into an array, by spatially separating the members of the library. Examples of suitable libraries for arraying include nucleic acid libraries (including DNA, cDNA, oligonucleotide, etc. libraries), peptide, polypeptide and protein libraries, as well as libraries comprising any molecules, such as ligand libraries, among others.

The library can be fixed or immobilized onto a solid phase (e.g. a solid substrate), to limit diffusion and admixing of the members. In some cases, libraries of DNA binding ligands may be prepared. In particular, the libraries may be immobilized to a substantially planar solid phase, including membranes and non-porous substrates such as plastic and glass. Furthermore, the library can be arranged in such a way that indexing (i.e., reference or access to a particular member) is facilitated. In some examples, the members of the library can be applied as spots in a grid formation. Common assay systems may be adapted for this purpose. For example, an array may be immobilized on the surface of a microplate, either with multiple members in a well, or with a single member in each well. Furthermore, the solid substrate may be a membrane, such as a nitrocellulose or nylon membrane (for example, membranes used in blotting experiments). Alternative substrates include glass, or silica based substrates. Thus, the library can be immobilized by any suitable method known in the art, for example, by charge interactions, or by chemical coupling to the walls or bottom of the wells, or the surface of the membrane. Other means of arranging and fixing may be used, for example, pipetting, drop-touch, piezoelectric means, ink-jet and bubblejet technology, electrostatic application, etc. In the case of silicon-based chips, photolithography may be utilized to arrange and fix the libraries on the chip.

The library may be arranged by being "spotted" onto the solid substrate; this may be done by hand or by making use of robotics to deposit the members. In general, arrays may be described as macroarrays or microarrays, the difference being the size of the spots. Macroarrays can contain spot sizes of about 300 microns or larger and may be easily imaged by existing gel and blot scanners. The spot sizes in microarrays can be less than 200 microns in diameter and these arrays usually contain thousands of spots. Thus, microarrays may require specialized robotics and imaging equipment, which may need to be custom made Instrumentation is described generally in a review by Cortese, 2000, *The Scientist* 14[11]:26.

Techniques for producing immobilized libraries of DNA molecules have been described in the art. Generally, most prior art methods described how to synthesize single-stranded nucleic acid molecule libraries, using for example masking techniques to build up various permutations of sequences at the various discrete positions on the solid substrate. U.S. Pat. No. 5,837,832 describes an improved method for producing DNA arrays immobilized to silicon substrates based on very large scale integration technology. In particular, U.S. Pat. No. 5,837,832 describes a strategy called "tiling" to synthesize specific sets of probes at spatially-defined locations on a substrate which may be used to produce the immobilized DNA libraries of the present disclosure. U.S. Pat. No. 5,837,832 also provides references for earlier techniques that may also be used. In other cases, arrays may also be built using photo deposition chemistry.

Arrays of peptides (or peptidomimetics) may also be synthesized on a surface in a manner that places each distinct library member (e.g., unique peptide sequence) at a discrete, predefined location in the array. The identity of each library member is determined by its spatial location in the array. The locations in the array where binding interactions between a predetermined molecule (e.g., a target or probe) and reactive library members occur is determined, thereby identifying the sequences of the reactive library members on the basis of spatial location. These methods are described in U.S. Pat. No. 5,143,854; WO90/15070 and WO92/10092; Fodor et al. (1991) *Science*, 251: 767; Dower and Fodor (1991) *Ann. Rep. Med. Chem.*, 26: 271

To aid detection, labels can be used (as discussed above) such as any readily detectable reporter, for example, a fluorescent, bioluminescent, phosphorescent, radioactive, etc. reporter. Such reporters, their detection, coupling to targets/probes, etc. are discussed elsewhere in this document. Labelling of probes and targets is also disclosed in Shalon et al., 1996, *Genome Res* 6(7):639-45.

Examples of some commercially available microarray formats are set out in Table 1 below (see also Marshall and Hodgson, 1998, *Nature Biotechnology*, 16(1), 27-31).

TABLE 1

Examples of currently available hybridization microarray formats

| Company | Product name | Arraying method | Hybridization step | Readout |
|---|---|---|---|---|
| Affymetrix, Inc., Santa Clara, California | GeneChip ® | In situ (on-chip) photolithographic synthesis of ~20-25-mer oligos onto silicon wafers, which are diced into 1.25 $cm^2$ or 5.25 $cm^2$ chips | 10,000-260,000 oligo features probed with labeled 30-40 nucleotide fragments of sample cDNA or antisense RNA | Fluorescence |
| Brax, Cambridge, UK | | Short synthetic oligo, synthesized off-chip | 1000 oligos on a "universal chip" probed with tagged nucleic acid | Mass spectrometry |
| Gene Logic, Inc., Columbia, Maryland | READS ™ | | | |
| Genometrix Inc., The Woodlands, Texas | Universal Arrays ™ | | | |
| GENSET, Paris, France | | | | |
| Hyseq Inc., Sunnyvale, California | HyChip ™ | 500-2000 nt DNA samples printed onto 0.6 $cm^2$ (HyGnostics) or ~18 $cm^2$ (Gene Discovery) membranes | 64 sample cDNA spots probed with 8,000 7-mer oligos (HyGnostics) or <=55,000 sample cDNA spots probed with 300 7-mer oligo (Gene Discovery) | Radioisotope |
| | | Fabricated 5-mer oligos printed as 1.15 $cm^2$ arrays onto glass (HyChip) | Universal 1024 oligo spots probed 10 kb sample cDNAs, labeled 5-mer oligo, and ligase | Fluorescence |
| Incyte Pharmaceuticals, Inc., Palo Alto, California | GEM | Piezoelectric printing for spotting PCR fragments and on-chip synthesis of oligos | <=1000 (eventually 10,000) oligo/PCR fragment spots probed with labeled RNA | Fluorescence and radioisotope |
| Molecular Dynamics, Inc., Sunnyvale, California | Storm ® FluorImager ® | 500-5000 nt cDNAs printed by pen onto ~10 $cm^2$ on glass slide | ~10,000 cDNA spots probed with 200-400 nt labeled sample cDNAs | Fluorescence |
| Nanogen, San Diego, California | Semiconductor Microchip | Prefabricated ~20-mer oligos, captured onto electroactive spots on silicon wafers, which are diced into <=1 $cm^2$ chips | 25, 64, 400 (and eventually 10,000) oligo spots polarized to enhance hybridization to 200-400 nt labeled sample cDNAs | Fluorescence |
| Protogene Laboratories, Palo Alto, California | | On-chip synthesis of 40-50-mer oligos onto 9 $cm^2$ glass chip via printing to a surface-tension array | <=8,000 oligo spots probed with 200-400 nt labeled sample nucleic acids | Fluorescence |

TABLE 1-continued

Examples of currently available hybridization microarray formats

| Company | Product name | Arraying method | Hybridization step | Readout |
|---|---|---|---|---|
| Sequenom, Hamburg, Germany, and San Diego, California | MassArray SpectroChip | Off-set printing of array; around 20-25-mer oligos | 250 locations per SpectroChip interrogated by laser desorbtion and mass spectrometry | Mass spectrometry |
| Synteni, Inc., Fremont, California | UniGEM ™ | 500-5,000 nt cDNAs printed by tip onto ~4 cm$^2$ glass chip | <=10,000 cDNA spots probed with 200-400 nt labeled sample cDNAs | Fluorescence |
| Nimblegen Systems Inc., Madison | Homo sapiens Whole-Genome 60mer Microarray | 38,000 transcripts with 5 probes per gene 17.4 mm × 13 mm | | 5-micron scanning platform |
| The German Cancer Institute, Heidelberg, Germany | | Prototypic PNA macrochip with on-chip synthesis of probes using f-moc or t-moc chemistry | Around 1,000 spots on a 8 × 12 cm chip | Fluorescence/mass spectrometry |

In order to generate data from array-based assays a signal can detected to signify the presence of or absence of hybridization between a probe and a nucleotide sequence. Further, direct and indirect labeling techniques can also be utilized. For example, direct labeling incorporates fluorescent dyes directly into the nucleotide sequences that hybridize to the array associated probes (e.g., dyes are incorporated into nucleotide sequence by enzymatic synthesis in the presence of labeled nucleotides or PCR primers). Direct labeling schemes can yield strong hybridization signals, for example by using families of fluorescent dues with similar chemical structures and characteristics, and can be simple to implement. In cases comprising direct labeling of nucleic acids, cyanine or alexa analogs can be utilized in multiple-fluor comparative array analyses. In other embodiments, indirect labeling schemes can be utilized to incorporate epitopes into the nucleic acids either prior to or after hybridization to the microarray probes. One or more staining procedures and reagents can be used to label the hybridized complex (e.g., a fluorescent molecule that binds to the epitopes, thereby providing a fluorescent signal by virtue of the conjugation of dye molecule to the epitope of the hybridized species).

In various embodiments, suitable sequencing methods described herein or otherwise known in the art will be used to obtain sequence information from nucleic acid molecules within a sample. Sequencing can be accomplished through classic Sanger sequencing methods which are well known in the art. Sequence can also be accomplished using high-throughput systems some of which allow detection of a sequenced nucleotide immediately after or upon its incorporation into a growing strand, i.e., detection of sequence in real time or substantially real time. In some cases, high throughput sequencing generates at least 1,000, at least 5,000, at least 10,000, at least 20,000, at least 30,000, at least 40,000, at least 50,000, at least 100,000 or at least 500,000 sequence reads per hour; where the sequencing reads can be at least about 50, about 60, about 70, about 80, about 90, about 100, about 120, about 150, about 180, about 210, about 240, about 270, about 300, about 350, about 400, about 450, about 500, about 600, about 700, about 800, about 900, or about 1000 bases per read.

In some embodiments, high-throughput sequencing involves the use of technology available by Illumina's Genome Analyzer IIX, MiSeq personal sequencer, or HiSeq systems, such as those using HiSeq 2500, HiSeq 1500, HiSeq 2000, or HiSeq 1000 machines. These machines use reversible terminator-based sequencing by synthesis chemistry. These machine can do 200 billion DNA reads or more in eight days. Smaller systems may be utilized for runs within 3, 2, 1 days or less time.

In some embodiments, high-throughput sequencing involves the use of technology available by ABI Solid System. This genetic analysis platform that enables massively parallel sequencing of clonally-amplified DNA fragments linked to beads. The sequencing methodology is based on sequential ligation with dye-labeled oligonucleotides.

The next generation sequencing can comprise ion semiconductor sequencing (e.g., using technology from Life Technologies (Ion Torrent)). Ion semiconductor sequencing can take advantage of the fact that when a nucleotide is incorporated into a strand of DNA, an ion can be released. To perform ion semiconductor sequencing, a high density array of micromachined wells can be formed. Each well can hold a single DNA template. Beneath the well can be an ion sensitive layer, and beneath the ion sensitive layer can be an ion sensor. When a nucleotide is added to a DNA, H+ can be released, which can be measured as a change in pH. The H+ ion can be converted to voltage and recorded by the semiconductor sensor. An array chip can be sequentially flooded with one nucleotide after another. No scanning, light, or cameras can be required. In some cases, an ION-PROTON™ Sequencer is used to sequence nucleic acid. In some cases, an IONPGM™ Sequencer is used. The Ion Torrent Personal Genome Machine (PGM). The PGM can do 10 million reads in two hours.

In some embodiments, high-throughput sequencing involves the use of technology available by Helicos BioSciences Corporation (Cambridge, Mass.) such as the Single Molecule Sequencing by Synthesis (SMSS) method. SMSS is unique because it allows for sequencing the entire human genome in up to 24 hours. Finally, SMSS is described in part in US Publication Application Nos. 20060024711; 20060024678; 20060012793; 20060012784; and 20050100932.

In some embodiments, high-throughput sequencing involves the use of technology available by 454 Lifesciences, Inc. (Branford, Conn.) such as the PicoTiterPlate device which includes a fiber optic plate that transmits chemiluminescent signal generated by the sequencing reaction to be recorded by a CCD camera in the instrument. This use of fiber optics allows for the detection of a minimum of 20 million base pairs in 4.5 hours.

Methods for using bead amplification followed by fiber optics detection are described in Marguiles, M., et al. "Genome sequencing in microfabricated high-density pricoliter reactors", Nature, doi:10.1038/nature03959; and well as in US Publication Application Nos. 20020012930; 20030068629; 20030100102; 20030148344; 20040248161; 20050079510, 20050124022; and 20060078909.

In some embodiments, high-throughput sequencing is performed using Clonal Single Molecule Array (Solexa, Inc.) or sequencing-by-synthesis (SBS) utilizing reversible terminator chemistry. These technologies are described in part in U.S. Pat. Nos. 6,969,488; 6,897,023; 6,833,246; 6,787,308; and US Publication Application Nos. 20040106110; 20030064398; 20030022207; and Constans, A., The Scientist 2003, 17(13):36.

The next generation sequencing technique can comprises real-time (SMRT™) technology by Pacific Biosciences. In SMRT, each of four DNA bases can be attached to one of four different fluorescent dyes. These dyes can be phospho-linked. A single DNA polymerase can be immobilized with a single molecule of template single stranded DNA at the bottom of a zero-mode waveguide (ZMW). A ZMW can be a confinement structure which enables observation of incorporation of a single nucleotide by DNA polymerase against the background of fluorescent nucleotides that can rapidly diffuse in an out of the ZMW (in microseconds). It can take several milliseconds to incorporate a nucleotide into a growing strand. During this time, the fluorescent label can be excited and produce a fluorescent signal, and the fluorescent tag can be cleaved off. The ZMW can be illuminated from below. Attenuated light from an excitation beam can penetrate the lower 20-30 nm of each ZMW. A microscope with a detection limit of 20 zepto liters ($10''$ liters) can be created. The tiny detection volume can provide 1000-fold improvement in the reduction of background noise. Detection of the corresponding fluorescence of the dye can indicate which base was incorporated. The process can be repeated.

In some cases, the next generation sequencing is nanopore sequencing (See, e.g., Soni G V and Meller A. (2007) Clin Chem 53: 1996-2001). A nanopore can be a small hole, of the order of about one nanometer in diameter. Immersion of a nanopore in a conducting fluid and application of a potential across it can result in a slight electrical current due to conduction of ions through the nanopore. The amount of current which flows can be sensitive to the size of the nanopore. As a DNA molecule passes through a nanopore, each nucleotide on the DNA molecule can obstruct the nanopore to a different degree. Thus, the change in the current passing through the nanopore as the DNA molecule passes through the nanopore can represent a reading of the DNA sequence. The nanopore sequencing technology can be from Oxford Nanopore Technologies; e.g., a GridlON system. A single nanopore can be inserted in a polymer membrane across the top of a microwell. Each microwell can have an electrode for individual sensing. The microwells can be fabricated into an array chip, with 100,000 or more microwells (e.g., more than 200,000, 300,000, 400,000, 500,000, 600,000, 700,000, 800,000, 900,000, or 1,000,000) per chip. An instrument (or node) can be used to analyze the chip. Data can be analyzed in real-time. One or more instruments can be operated at a time. The nanopore can be a protein nanopore, e.g., the protein alpha-hemolysin, a heptameric protein pore. The nanopore can be a solid-state nanopore made, e.g., a nanometer sized hole formed in a synthetic membrane (e.g., $SiN_x$, or $SiO_2$). The nanopore can be a hybrid pore (e.g., an integration of a protein pore into a solid-state membrane). The nanopore can be a nanopore with an integrated sensors (e.g., tunneling electrode detectors, capacitive detectors, or graphene based nano-gap or edge state detectors (see e.g., Garaj et al. (2010) Nature vol. 67, doi: 10.1038/nature09379)). A nanopore can be functionalized for analyzing a specific type of molecule (e.g., DNA, RNA, or protein). Nanopore sequencing can comprise "strand sequencing" in which intact DNA polymers can be passed through a protein nanopore with sequencing in real time as the DNA translocates the pore. An enzyme can separate strands of a double stranded DNA and feed a strand through a nanopore. The DNA can have a hairpin at one end, and the system can read both strands. In some cases, nanopore sequencing is "exonuclease sequencing" in which individual nucleotides can be cleaved from a DNA strand by a processive exonuclease, and the nucleotides can be passed through a protein nanopore. The nucleotides can transiently bind to a molecule in the pore (e.g., cyclodextran). A characteristic disruption in current can be used to identify bases.

Nanopore sequencing technology from GENIA can be used. An engineered protein pore can be embedded in a lipid bilayer membrane. "Active Control" technology can be used to enable efficient nanopore-membrane assembly and control of DNA movement through the channel. In some cases, the nanopore sequencing technology is from NABsys. Genomic DNA can be fragmented into strands of average length of about 100 kb. The 100 kb fragments can be made single stranded and subsequently hybridized with a 6-mer probe. The genomic fragments with probes can be driven through a nanopore, which can create a current-versus-time tracing. The current tracing can provide the positions of the probes on each genomic fragment. The genomic fragments can be lined up to create a probe map for the genome. The process can be done in parallel for a library of probes. A genome-length probe map for each probe can be generated. Errors can be fixed with a process termed "moving window Sequencing By Hybridization (mwSBH)." In some cases, the nanopore sequencing technology is from IBM/Roche. An electron beam can be used to make a nanopore sized opening in a microchip. An electrical field can be used to pull or thread DNA through the nanopore. A DNA transistor device in the nanopore can comprise alternating nanometer sized layers of metal and dielectric. Discrete charges in the DNA backbone can get trapped by electrical fields inside the DNA nanopore. Turning off and on gate voltages can allow the DNA sequence to be read.

The next generation sequencing can comprise DNA nanoball sequencing (as performed, e.g., by Complete Genomics; see e.g., Drmanac et al. (2010) Science 327: 78-81). DNA can be isolated, fragmented, and size selected. For example, DNA can be fragmented (e.g., by sonication) to a mean length of about 500 bp. Adaptors (Ad1) can be attached to the ends of the fragments. The adaptors can be used to hybridize to anchors for sequencing reactions. DNA with adaptors bound to each end can be PCR amplified. The adaptor sequences can be modified so that complementary single strand ends bind to each other forming circular DNA. The DNA can be methylated to protect it from cleavage by a type IIS restriction enzyme used in a subsequent step. An adaptor (e.g., the right adaptor) can have a restriction recognition site, and the restriction recognition site can remain non-methylated. The non-methylated restriction recognition site in the adaptor can be recognized by a restriction enzyme (e.g., AcuI), and the DNA can be cleaved by AcuI 13 bp to the right of the right adaptor to form linear double stranded DNA. A second round of right and left adaptors (Ad2) can be ligated onto either end of the linear DNA, and all DNA with both adapters bound can be PCR amplified (e.g., by PCR). Ad2 sequences can be modified to allow them to bind each other and form circular DNA. The DNA can be methylated, but a restriction enzyme recognition site can remain non-methylated on the left Adl adapter. A restriction enzyme (e.g., AcuI) can be applied, and the DNA can be cleaved 13 bp to the left of the Adl to form a linear DNA fragment. A third round of right and left adaptor (Ad3) can be ligated to the right and left flank of the linear DNA, and the resulting fragment can be PCR amplified. The adaptors can be modified so that they can bind to each other and form circular DNA. A type III restriction enzyme (e.g., EcoP15) can be added; EcoP15 can cleave the DNA 26 bp to the left of Ad3 and 26 bp to the right of Ad2. This cleavage can remove a large segment of DNA and linearize the DNA once again. A fourth round of right and left adaptors (Ad4) can be ligated to the DNA, the DNA can be amplified (e.g., by PCR), and modified so that they bind each other and form the completed circular DNA template.

Rolling circle replication (e.g., using Phi 29 DNA polymerase) can be used to amplify small fragments of DNA. The four adaptor sequences can contain palindromic sequences that can hybridize and a single strand can fold onto itself to form a DNA nanoball (DNB™) which can be approximately 200-300 nanometers in diameter on average. A DNA nanoball can be attached (e.g., by adsorption) to a microarray (sequencing flowcell). The flow cell can be a silicon wafer coated with silicon dioxide, titanium and hexamehtyldisilazane (HMDS) and a photoresist material. Sequencing can be performed by unchained sequencing by ligating fluorescent probes to the DNA. The color of the fluorescence of an interrogated position can be visualized by a high resolution camera. The identity of nucleotide sequences between adaptor sequences can be determined.

In some embodiments, high-throughput sequencing can take place using AnyDot.chips (Genovoxx, Germany). In particular, the AnyDot.chips allow for 10×-50× enhancement of nucleotide fluorescence signal detection. AnyDot.chips and methods for using them are described in part in International Publication Application Nos. WO 02088382, WO 03020968, WO 03031947, WO 2005044836, PCT/EP 05/05657, PCT/EP 05/05655; and German Patent Application Nos. DE 101 49 786, DE 102 14 395, DE 103 56 837, DE 10 2004 009 704, DE 10 2004 025 696, DE 10 2004 025 746, DE 10 2004 025 694, DE 10 2004 025 695, DE 10 2004 025 744, DE 10 2004 025 745, and DE 10 2005 012 301.

Other high-throughput sequencing systems include those disclosed in Venter, J., et al. Science 16 Feb. 2001; Adams, M. et al. Science 24 Mar. 2000; and M. J. Levene, et al. Science 299:682-686, January 2003; as well as US Publication Application No. 20030044781 and 2006/0078937. Overall such system involve sequencing a target nucleic acid molecule having a plurality of bases by the temporal addition of bases via a polymerization reaction that is measured on a molecule of nucleic acid, i.e. the activity of a nucleic acid polymerizing enzyme on the template nucleic acid molecule to be sequenced is followed in real time. Sequence can then be deduced by identifying which base is being incorporated into the growing complementary strand of the target nucleic acid by the catalytic activity of the nucleic acid polymerizing enzyme at each step in the sequence of base additions. A polymerase on the target nucleic acid molecule complex is provided in a position suitable to move along the target nucleic acid molecule and extend the oligonucleotide primer at an active site. A plurality of labeled types of nucleotide analogs are provided proximate to the active site, with each distinguishable type of nucleotide analog being complementary to a different nucleotide in the target nucleic acid sequence. The growing nucleic acid strand is extended by using the polymerase to add a nucleotide analog to the nucleic acid strand at the active site, where the nucleotide analog being added is complementary to the nucleotide of the target nucleic acid at the active site. The nucleotide analog added to the oligonucleotide primer as a result of the polymerizing step is identified. The steps of providing labeled nucleotide analogs, polymerizing the growing nucleic acid strand, and identifying the added nucleotide analog are repeated so that the nucleic acid strand is further extended and the sequence of the target nucleic acid is determined.

In particular embodiments, the present disclosure further provides kits comprising ore or more components of the disclosure. The kits can be used or any application apparent to those of skill in the art, including those described above. The kits can comprise, for example, a plurality of association molecules, a fixative agent, a restriction endonuclease, a ligase, and/or a combination thereof. In some cases, the association molecules can be proteins including, for example, histones. In some cases, the fixative agent can be formaldehyde or any other DNA crosslinking agent.

In some cases, the kit can further comprise a plurality of beads. The beads can be paramagnetic and/or are coated with a capturing agent. For example, the beads can be coated with streptavidin and/or an antibody.

In some cases, the kit can comprise adaptor oligonucleotides and/or sequencing primers. Further, the kit can comprise a device capable of amplifying the read-pairs using the adaptor oligonucleotides and/or sequencing primers.

In some cases, the kit can also comprise other reagents including but not limited to lysis buffers, ligation reagents (e.g. dNTPs, polymerase, polynucleotide kinase, and/or ligase buffer, etc.), and PCR reagents (e.g. dNTPs, polymerase, and/or PCR buffer, etc.).

The kit can also include instructions for using the components of the kit and/or for generating the read-pairs.

Figure 8:
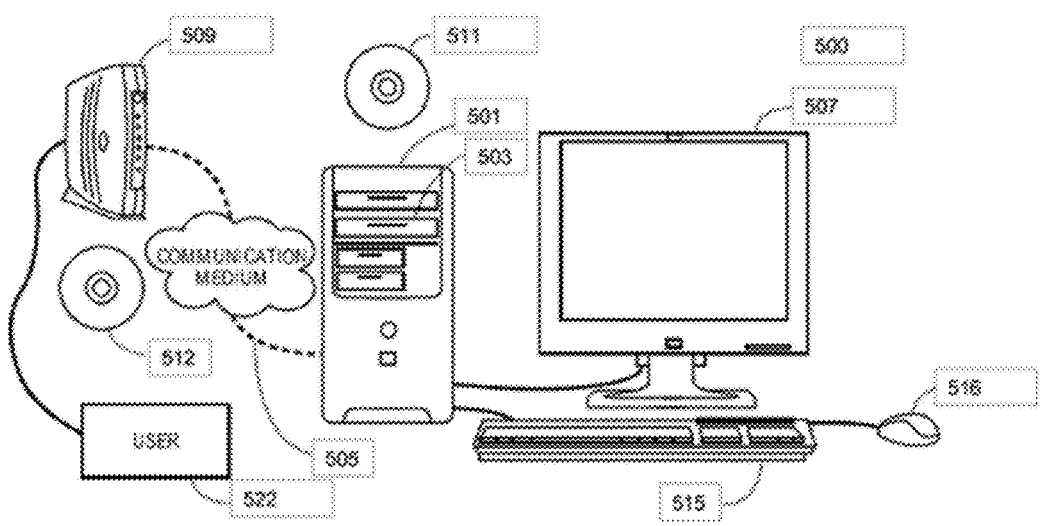
FIG. 8 illustrates various components of an exemplary computer system according to various embodiments of the present disclosure.

The computer system 500 illustrated in FIG. 8 may be understood as a logical apparatus that can read instructions from media 511 and/or a network port 505, which can optionally be connected to server 509 having fixed media 512. The system, such as shown in FIG. 8 can include a CPU 501, disk drives 503, optional input devices such as keyboard 515 and/or mouse 516 and optional monitor 507. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 522 as illustrated in FIG. 8.

Figure 9:
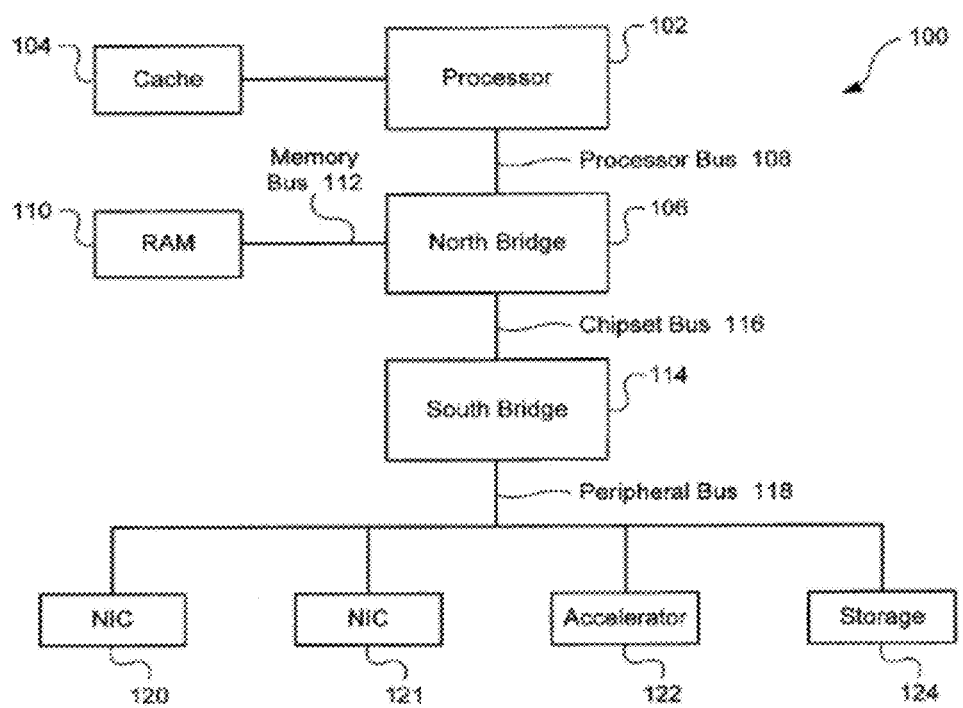
FIG. 9 is a block diagram illustrating the architecture of an exemplary computer system that can be used in connection with various embodiments of the present disclosure.

FIG. 9 is a block diagram illustrating a first example architecture of a computer system 100 that can be used in connection with example embodiments of the present disclosure. As depicted in FIG. 9, the example computer system can include a processor 102 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices.

As illustrated in FIG. 9, a high speed cache 104 can be connected to, or incorporated in, the processor 102 to provide a high speed memory for instructions or data that have been recently, or are frequently, used by processor 102. The processor 102 is connected to a north bridge 106 by a processor bus 108. The north bridge 106 is connected to random access memory (RAM) 110 by a memory bus 112 and manages access to the RAM 110 by the processor 102. The north bridge 106 is also connected to a south bridge 114 by a chipset bus 116. The south bridge 114 is, in turn, connected to a peripheral bus 118. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 118. In some alternative architectures, the functionality of the north bridge can be incorporated into the processor instead of using a separate north bridge chip.

In some embodiments, system 100 can include an accelerator card 122 attached to the peripheral bus 118. The accelerator can include field programmable gate arrays (FPGAs) or other hardware for accelerating certain processing. For example, an accelerator can be used for adaptive data restructuring or to evaluate algebraic expressions used in extended set processing.

Software and data are stored in external storage 124 and can be loaded into RAM 110 and/or cache 104 for use by the processor. The system 100 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present disclosure.

In this example, system 100 also includes network interface cards (NICs) 120 and 121 connected to the peripheral bus for providing network interfaces to external storage, such as Network Attached Storage (NAS) and other computer systems that can be used for distributed parallel processing.

Figure 10:
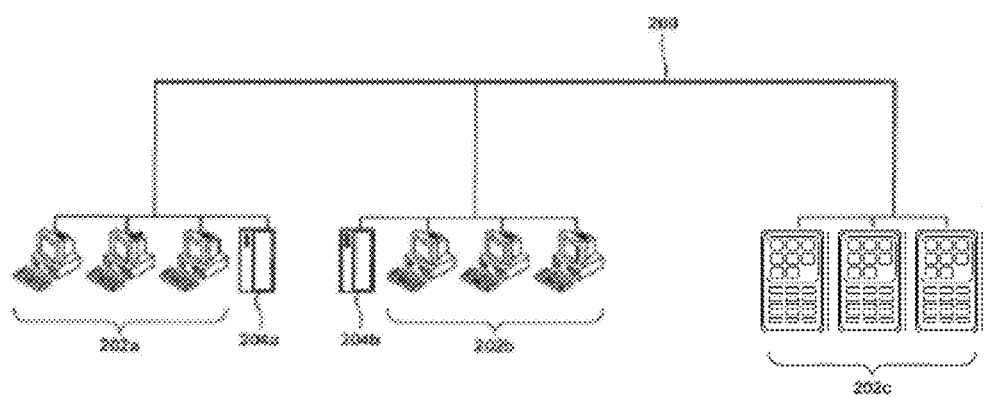
FIG. 10 is a diagram illustrating an exemplary computer network that can be used in connection with various embodiments of the present disclosure.

FIG. 10 is a diagram showing a network 200 with a plurality of computer systems 202a, and 202b, a plurality of cell phones and personal data assistants 202c, and Network Attached Storage (NAS) 204a, and 204b. In example embodiments, systems 202a, 202b, and 202c can manage data storage and optimize data access for data stored in Network Attached Storage (NAS) 204a and 204b. A mathematical model can be used for the data and be evaluated using distributed parallel processing across computer systems 202a, and 202b, and cell phone and personal data assistant systems 202c. Computer systems 202a, and 202b, and cell phone and personal data assistant systems 202c can also provide parallel processing for adaptive data restructuring of the data stored in Network Attached Storage (NAS) 204a and 204b. FIG. 10 illustrates an example only, and a wide variety of other computer architectures and systems can be used in conjunction with the various embodiments of the present disclosure. For example, a blade server can be used to provide parallel processing. Processor blades can be connected through a back plane to provide parallel processing. Storage can also be connected to the back plane or as Network Attached Storage (NAS) through a separate network interface.

In some example embodiments, processors can maintain separate memory spaces and transmit data through network interfaces, back plane or other connectors for parallel processing by other processors. In other embodiments, some or all of the processors can use a shared virtual address memory space.

Figure 11:
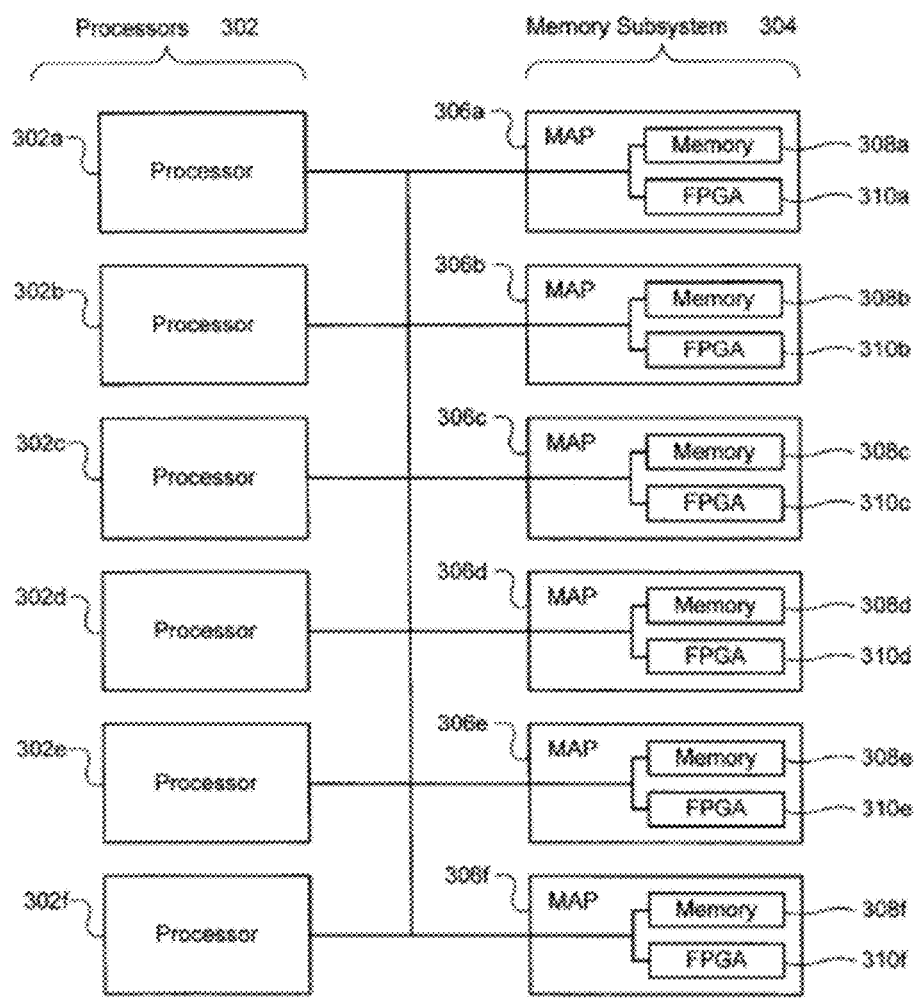
FIG. 11 is a block diagram illustrating the architecture of another exemplary computer system that can be used in connection with various embodiments of the present disclosure.

FIG. 11 is a block diagram of a multiprocessor computer system 300 using a shared virtual address memory space in accordance with an example embodiment. The system includes a plurality of processors 302a-f that can access a shared memory subsystem 304. The system incorporates a plurality of programmable hardware memory algorithm processors (MAPs) 306a-f in the memory subsystem 304. Each MAP 306a-f can comprise a memory 308a-f and one or more field programmable gate arrays (FPGAs) 310a-f. The MAP provides a configurable functional unit and particular algorithms or portions of algorithms can be provided to the FPGAs 310a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 308a-f, allowing it to execute tasks independently of, and asynchronously from, the respective microprocessor 302a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 11, system on chips (SOCs), application specific integrated circuits (ASICs), or other processing and logic elements. For example, the Set Processor and Optimizer can be implemented with hardware acceleration through the use of a hardware accelerator card, such as accelerator card 122 illustrated in FIG. 9.

The following examples are intended to illustrate but not limit the disclosure. While they are typical of those that might be used, other procedures known to those skilled in the art may alternatively be used.

EXAMPLES

Example 1. Methods to Generate Chromatin In Vitro

Two approaches to reconstitute chromatin are of particular attention: one approach is to use ATP-independent random deposition of histones onto DNA, while the other approach uses ATP-dependent assembly of periodic nucleosomes. The disclosure allows the use of either approach with one or more methods disclosed herein. Examples of both approaches to generate chromatin can be found in Lusser et al. ("Strategies for the reconstitution of chromatin," Nature Methods (2004), 1(1):19-26), which is incorporated herein by reference in its entirety, including the references cited therein.

Example 2. Genome Assembly Using HI-C Based Techniques

A genome from a human subject was fragmented into pseudo-contigs having a size of 500 kb. Using a Hi-C based method, a plurality of read pairs were generated by probing the physical layout of chromosomes within living cells. Any number of Hi-C based methods can be used to generate read pairs, including the method presented in Lieberman-Aiden et al. ("Comprehensive mapping of long range interactions reveals folding principles of the human genome," *Science* (2009), 326(5950):289-293), which is incorporated herein in-full, including the references cited therein. Read pairs were mapped to all pseudo-contigs and those pairs that mapped to two separate pseudo-contigs, were used to construct an adjacency matrix based upon the mapping data. At least about 50%, about 60%, about 70%, about 80%, about 90%, about 95% or about 99% of the read pairs were weighted by taking a function of the read's distance to the edge of the pseudo-contig so as to mathematically incorporate the empirically known higher probability of shorter contacts than longer contacts. Then, for each pseudo-contig, the adjacency matrix was analyzed to determine a path through the pseudo-contigs by finding the single best neighbor pseudo-contig, which was determined by having the highest sum-of-weights. By performing these methods, it was found that >97% of all pseudo-contigs identified their correct neighbor. Additional experiments can be performed to test the impact of shorter contigs and alternate weighting and path-finding schemes.

Alternatively, genome assembly using Hi-C data can include computational methods that exploit the signal of genomic proximity in Hi-C data sets for ultra-long scaffolding of de novo genome assemblies. Examples of such computational methods that can used with the methods disclosed herein, include the ligating adjacent chromatin method by Burton et al. (*Nature Biotechnology* 31:1119-1125 (2013)); and a DNA triangulation method by Kaplan et al. (*Nature Biotechnology* 31:1143-47 (2013)), which references are incorporated herein in-full, and any references cited therein. Further, it should be understood that these computational methods can be used in combination, including with the other genome assembly methods presented herein.

For example, a ligating adjacent chromatin method based on Burton et al. comprising the steps of (a) clustering contigs to chromosome groups, (b) ordering the contigs within one or more chromosome group, and then (c) assigning relative orientations to individual contigs, can be used with the methods disclosed herein. For step (a), contigs are placed into groups using hierarchical clustering. A graph is built, with each node initially representing one contig, and each edge between nodes having a weight equal to the number of Hi-C read-pairs linking the two contigs. The contigs are merged together using hierarchical agglomerative clustering with an average-linkage metric, which is applied until the number of groups are reduced to the expected number of distinct chromosomes (counting only groups with more than one contig). Repetitive contigs (contigs whose average link density with other contigs, normalized by number of restriction fragment sites, is greater than two times the average link density) and contigs with too few restriction fragment sites are not clustered. However, after clustering, each of these contigs is assigned to a group if its average link density with that group is greater than four times its average link densities with any other group. For step (b), a graph is built as in the clustering step, but with the edge weights between nodes equal to the inverse of the number of Hi-C links between the contigs, normalized by the number of restriction fragment sites per contig. Short contigs are excluded from this graph. A minimum spanning tree is calculated for this graph. The longest path in this tree, the "trunk", is found. The spanning tree is then modified so as to lengthen the trunk by adding to it contigs adjacent to the trunk, in ways that keep the total edge weight heuristically low. After a lengthened trunk is found for each group, it is converted into a full ordering as follows. The trunk is removed from the spanning tree, leaving a set of "branches" containing all contigs not in the trunk. These branches are reinserted into the trunk, the longest branches first, with the insertion sites chosen so as to maximize the number of links between adjacent contigs in the ordering. Short fragments are not reinserted; as a result, many small contigs that were clustered are left out of the final assembly. For step (c), the orientation of each contig within its ordering is determined by taking into account the exact position of the Hi-C link alignments on each contig. It is assumed that the likelihood of a Hi-C link connecting two reads at a genomic distance of x is roughly $1/x$ for $x \geq \sim 100$ Kb. A weighted, directed, acyclic graph (WDAG) is built representing all possible ways to orient the contigs in the given order. Each edge in the WDAG corresponds to a pair of adjacent contigs in one of their four possible combined orientations, and the edge weight is set to the log-likelihood of observing the set of Hi-C link distances between the two contigs, assuming they are immediately adjacent with the given orientation. For each contig, a quality score for its orientation is calculated as follows. The log-likelihood of the observed set of Hi-C links between this contig, in its current orientation, and its neighbors, is found. Then the contig is flipped and the log-likelihood is calculated again. The first log-likelihood is guaranteed to be higher because of how the orientations are calculated. The difference between the log-likelihoods is taken as a quality score.

An alternative DNA triangulation method similar to Kaplan et al. can also be used in the methods disclosed herein to assemble a genome from contigs and read pairs. DNA triangulation is based upon the use of high-throughput in vivo genome-wide chromatin interaction data to infer genomic location. For the DNA triangulation method, the CTR pattern is first quantified by partitioning a genome into 100-kb bins, each representing a large virtual contig, and calculating for each placed contig its average interaction frequency with each chromosome. To evaluate localization over long ranges, interaction data of a contig with its flanking 1 mb on each side is omitted. The average interaction frequency strongly separates inter-from intrachromosomal interactions, and is highly predictive of which chromosome a contig belongs to. Next, a simple multiclass model, a naive Bayes classifier, is trained to predict the chromosome of each contig based on its average interaction frequency with each chromosome. The assembled portion of the genome is used to fit a probabilistic single-parameter exponential decay model describing the relationship between Hi-C interaction frequency and genomic distance (the DDD pattern). In each turn, a contig is removed from the chromosome, along with a flanking region of 1 Mb on each side. It is then estimated the most likely position for each contig based upon the interaction profile and decay model. The prediction error is quantified as the absolute value of the distance between the predicted position and the actual position.

By combining the DNA triangulation method with long-insert libraries the predictability for each contig can be further improved. By knowing the chromosomal assignment and approximate location of each contig could significantly reduce the computational complexity of long-insert scaffolding, as each contig need only be paired with contigs in its vicinity; thereby resolving ambiguous contig joining, and reduce assembly errors where contigs which are located at distant regions of a chromosome or on different chromosomes, are incorrectly joined.

Example 3. Methods for Haplotype Phasing

Because the read pairs generated by the methods disclosed herein are generally derived from intra-chromosomal contacts, any read pairs that contain sites of heterozygosity will also carry information about their phasing. Using this information, reliable phasing over short, intermediate and even long (megabase) distances can be performed rapidly and accurately. Experiments designed to phase data from one of the 1000 genomes trios (a set of mother/father/offspring genomes) have reliably inferred phasing. Additionally, haplotype reconstruction using proximity-ligation similar to Selvaraj et al. (*Nature Biotechnology* 31:1111-1118 (2013)) can also be used with haplotype phasing methods disclosed herein.

For example, a haplotype reconstruction using proximity-ligation based method can also be used in the methods disclosed herein in phasing a genome. A haplotype reconstruction using proximity-ligation based method combines a proximity-ligation and DNA sequencing with a probabilistic algorithm for haplotype assembly. First, proximity-ligation sequencing is performed using a chromosome capture protocol, such as Hi-C protocol. These methods can capture DNA fragments from two distant genomic loci that looped together in three-dimensional space. After shotgun DNA-sequencing of the resulting DNA library, paired-end sequencing reads have 'insert sizes' that range from several hundred base pairs to tens of millions of base pairs. Thus, short DNA fragments generated in a Hi-C experiment can yield small haplotype blocks, long fragments ultimately can link these small blocks together. With enough sequencing coverage, this approach has the potential to link variants in discontinuous blocks and assemble every such block into a single haplotype. This data is then combined with a probabilistic algorithm for haplotype assembly. The probabilistic algorithm utilizes a graph in which nodes correspond to heterozygous variants and edges correspond to overlapping sequence fragments that may link the variants. This graph might contain spurious edges resulting from sequencing errors or trans interactions. A max-cut algorithm is then used to predict parsimonious solutions that are maximally consistent with the haplotype information provided by the set of input sequencing reads. Because proximity ligation generates larger graphs than conventional genome sequencing or mate-pair sequencing, computing time and number of iterations are modified so that the haplotypes can be predicted with reasonable speed and high accuracy. The resulting data can then be used to guide local phasing using Beagle software and sequencing data from the genome project to generate chromosome-spanning haplotypes with high resolution and accuracy.

Example 4. Methods for Meta-Genomic Assembly

Microbes are collected from an environment and fixed with a fixative agent, such as formaldehyde, in order to form cross-links within the microbial cells. A plurality of contigs from the microbes is generated by using high-throughput sequencing. A plurality of read pairs are generated by using Hi-C based techniques. Read pairs that map to different contigs indicate which contigs are from the same species.

Example 5. Methods for Producing Extremely Long-Range Read Pairs (XLRPs)

Using commercially available kits, DNA is extracted to fragments sizes up to 150 kbp. The DNA is assembled into a reconstituted chromatin structure in vitro using a commercial kit from Activ Motif. The chromatin is biotinylated, fixed with formaldehyde, and immobilized onto streptavidin beads. The DNA fragments are digested with a restriction enzyme and incubated overnight. The resulting sticky ends are filled-in with an alpha-thio-dGTP and a biotinylated dCTP to generate blunt ends. The blunt ends are ligated with T4 ligase. The reconstituted chromatin is digested with a proteinase to recover the ligated DNA. The DNA is extracted from the beads and subject to an exonuclease digestion to remove biotin from unligated ends. The DNA recovered is sheared and the ends are filled-in with dNTPs. The biotinylated fragments are purified by a pull-down with streptavidin beads. In some cases, adaptors are ligated and the fragments are PCT amplified for high-throughput sequencing.

Example 6. Methods for Producing a High Quality Human Genome Assembly

With the knowledge that read pairs spanning considerable genomic distances can be generated by the disclosure, the utilization of this information for genomic assembly can be tested. The disclosure can significantly improve the linkage of de novo assemblies, potentially to chromosome-length scaffolds. An assessment can be performed on how complete an assembly can be produced and how much data will be required using the disclosure. To evaluate the efficacy of the present method for producing data that is valuable for assembly, a standard Illumina shotgun library and XLRP libraries can be built and sequenced. In one case, data from 1 Illumina HiSeq lane each of a standard shotgun library and an XLRP library are used. The data generated from each method is tested and compared with various existing assemblers. Optionally, a new assembler is also written to specifically tailor to the unique data produced by the disclosure. Optionally, a well-characterized human sample is used to provide a reference to compare the assembly produced by the present method against to assess its accuracy and completeness. Using the knowledge gained in the previous analyses, an assembler is produced to increase efficient and effective utilization the XLRP and shotgun data. A genome assembly of the quality of the December 2002 mouse genome draft, or better is generated using methods described herein.

One sample that can be used for this analysis is NA12878. DNA from sample cells are extracted using a variety of published techniques designed to maximize DNA fragment length. A standard Illumina TruSeq shotgun library and an XLRP library are each built. A single HiSeq lane of 2×150 bp sequence is obtained for each library, which may yield approximately 150 million read pairs per library. The shotgun data are assembled into contigs using algorithms for whole genome assembly. Examples of such algorithms include: Meraculous as described in Chapman et al. (PLOS ONE 6(8):e2350 (2011)) or SGA as described in Simpson et al. (Genome research 22(3):549-56 (2012)). The XLRP library reads are aligned to the contigs produced by the initial assembly. The alignments are used to further link the contigs. Once the effectiveness of the XLRP library for connecting contigs is ascertained, the Meraculous assembly is extended to integrate both the shotgun and XLRP libraries simultaneously into a single assembly process. Meraculous provides a strong foundation for the assembler. Optionally, an all-in-one assembler is produced to suit the specific needs of the disclosure. The human genome assembled by the disclosure is compared to any known sequence to evaluate the quality in the assembly of the genome.

Example 7. Methods for Phasing of Heterozygous SNPs for a Human Sample at High Accuracy from a Small Data Set In one experiment, approximately 44% of the heterozygous variants in a test human sample dataset are phased. All or nearly all phasing variants that are within one read-length's distance of a restriction site are captured. By using in silico analysis, more variants for phasing can be captured by using longer read lengths and using one or more combinations restriction enzymes for digestion. Using a combination of restriction enzymes with different restriction sites increases the proportion of the genome (and therefore heterozygous sites) that is within range of one of the two restriction sites that participate in each read pair. In silico analysis shows that the methods of the disclosure can phase more than 95% of known heterozygous positions using various combinations of two restriction enzymes. Additional enzymes and greater read lengths further increase the fraction of heterozygous sites that are observed and phased, up to a complete coverage and phasing.

Heterozygous site coverages achievable with various combinations of two restriction enzymes are calculated. The top three combinations, in terms of heterozygous sites in read proximity, are tested with the protocol. For each of these combinations, an XLRP library is produced and sequenced. The resulting reads are aligned to a human reference genome and compared to the known haplotypes of the sample to determine the accuracy of the protocol. Up to 90% or more of the heterozygous SNPs for a human sample are phased at an accuracy of 99% or greater using only 1 lane of Illumina HiSeq data. In addition, further variants are captured by increasing the read length to 300 bp. The read area around the observable restriction sites is effectively doubled. Additional restriction enzyme combinations are implemented increasing the coverage and accuracy.

Example 8. Extraction and Effects of High Molecular Weight DNA

Figure 7:
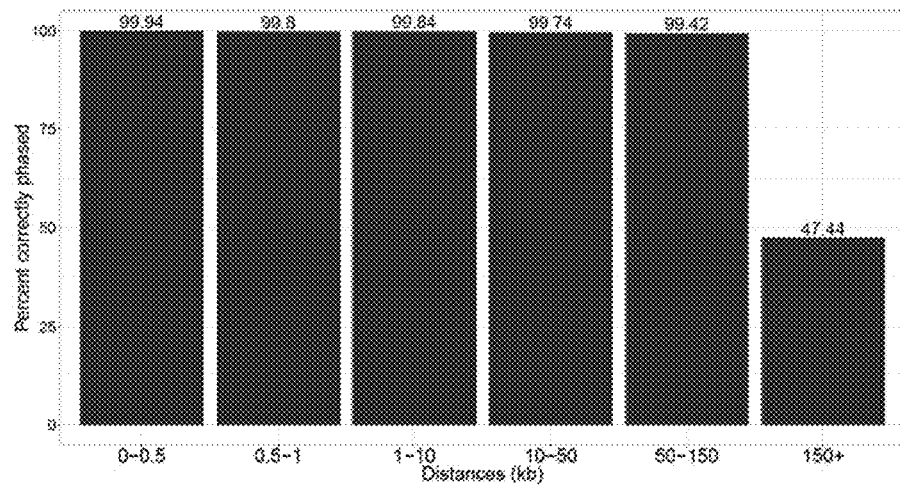
FIG. 7 illustrates the phasing accuracy for a sample with well-characterized haplotypes, NA12878. Indicated distances are those between the SNPs being phased.

DNA up to 150 kbp was extracted with commercially available kits. FIG. 7 demonstrates that XLRP libraries can be generated from capture read pairs up to maximum fragment lengths of the extracted DNA. Accordingly, the methods disclosed herein can be expected to be capable of generating read pairs from even longer stretches of DNA. There are numerous well-developed processes for high molecular weight DNA recovery, and these methods can be used with the methods or protocols disclose herein. Using an extraction method to produce large fragment lengths of DNA, an XLRP library is created from these fragments and the read pairs that are produced can be evaluated. For example, large molecular weight DNA can be extracted by, (1) gentle lysis of the cells according to Teague et al. (Proc. Nat. Acad. Sci. USA 107(24): 10848-53 (2010)) or Zhou et al. (PLOS Genetics, 5(11):e1000711 (2009)); and (2) agarose gel plugs according to Wing et al. (The Plant Journal: for Cell and Molecular Biology, 4(5):893-8 (1993)), which references are incorporated herein in-full, including any references cited therein, or by using the Aurora System from Boreal Genomics. These methods are capable of generating long DNA fragments beyond what is routinely required for next generation sequencing; however, any other suitable methods known in the art can be substituted for achieving similar results. The Aurora System provides exceptional results and can separate and concentrate DNA from tissue or other preparations up to, and beyond, a megabase in length. DNA extractions are prepared using each of these methodologies, beginning from a single GM12878 cell culture to control for possible differences at the sample level. The size distribution of the fragments can be evaluated by pulsed field gel electrophoresis according to Herschleb et al. (*Nature Protocols* 2(3):677-84 (2007)). Using the foregoing methods, extremely large stretches of DNA can be extracted and used to build XLRP libraries. The XLRP library is then sequenced and aligned. The resulting read data are analyzed by comparing the genomic distance between read pairs to the fragment sizes observed from the gel.

Example 9. Reducing Read-Pairs from Undesired Genomic Regions

RNA complementary to the undesired genomic regions is produced by in vitro transcription and added to the reconstructed chromatin prior to crosslinking. As the supplemented RNA binds to one or more undesired genomic regions, RNA binding decreases the crosslinking efficiency at these regions. The abundance of DNA from these regions in the cross-linked complexes is thereby reduced. The reconstructed chromatin is biotinylated and immobilized, and used as described above. In some cases, the RNA is designed to target repetitive regions in the genome.

Example 10. Increasing Read-Pairs from Desired Chromatin Regions

DNA from desired chromatin regions is produced in double stranded form for gene assembly or haplotyping.

Representation of DNA from undesired regions is accordingly reduced. Double-stranded DNA from desired chromatin regions is generated by primers that tile at such regions in multi-kilobase intervals. In other implementations of the method, the tiling intervals are varied to address desired regions of different sizes with desired replication efficiency. Primer binding sites across the desired regions are contacted with primers, optionally by melting the DNA. New strands of DNA are synthesized using the tiled primers. Undesired regions are reduced or eliminated, for example by targeting these regions with an endonuclease specific to single-stranded DNA. The remaining desired regions can be optionally amplified. The prepared sample is subjected to the sequencing library preparation methods as described elsewhere herein. In some implementations, read-pairs spanning distances up to the length of each desired chromatin regions are generated from each such desired chromatin region.

While preferred embodiments of the disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of generating a first read pair from a first DNA molecule, comprising:
   (a) providing at least one DNA-binding molecule to the first DNA molecule, wherein the first DNA molecule comprises a first DNA segment and a second DNA segment, and further wherein the at least one DNA-binding molecule binds to the first DNA molecule, thereby forming at least one complex;
   (b) contacting the at least one complex with a cross-linking agent;
   (c) cleaving the first DNA molecule between the first DNA segment and the second DNA segment, thereby generating a first DNA segment end and a second DNA segment end;
   (d) attaching the first DNA segment end to the second DNA segment end to form an attachment product; and
   (e) sequencing at least a portion of the attachment product such that sequence from the first DNA segment and the second DNA segment is obtained;
   thereby generating the first read pair information identifying the first DNA segment and the second DNA segment as originating from the first DNA molecule.

2. The method of claim 1, wherein the at least one DNA-binding molecule comprises a protein.

3. The method of claim 1, wherein the cross-linking agent comprises formaldehyde.

4. The method of claim 1, wherein attaching the first DNA segment end to the second DNA segment end to form an attachment product comprises ligating the first DNA segment end to the second DNA segment end.

5. The method of claim 1, comprising attaching at least one of the first DNA segment end and the second DNA segment end to at least one affinity label prior to sequencing.

6. The method of claim 1, comprising assigning contigs to which the first DNA segment map and the second DNA segment map to a first common scaffold.

7. The method of claim 1, further comprising generating a second read-pair from a second DNA molecule, comprising:
   (a) providing at least one DNA-binding molecule to the second DNA molecule, wherein the second DNA molecule comprises a third DNA segment and a fourth DNA segment, and further wherein the at least one DNA-binding molecule binds to the second DNA molecule, thereby forming at least one complex;
   (b) contacting the at least one complex with a cross-linking agent;
   (c) cleaving the second DNA molecule between the third DNA segment and the fourth DNA segment, thereby generating a third DNA segment end and a fourth DNA segment end;
   (d) attaching the third DNA segment end to the fourth DNA segment end to form an attachment product; and
   (e) sequencing at least a portion of the attachment product such that sequence from the third DNA segment and the fourth DNA segment is obtained;
   thereby generating the second read-pair information identifying the third DNA segment and the fourth DNA segment as originating from the second DNA molecule.

8. The method of claim 7, wherein less than 40% of the DNA segments from the first DNA molecule are attached to DNA segments from the second DNA molecule.

9. The method of claim 1, wherein the first DNA molecule is from a human subject.

10. The method of claim 1, wherein the first DNA molecule is cleaved using at least one restriction enzyme.

11. The method of claim 1, further comprising assembling at least one contig of the first DNA molecule using the first read pair.

12. The method of claim 1, comprising attaching at least one of the first DNA segment end and the second DNA segment end to a barcode.

13. The method of claim 2, wherein the protein comprises a histone.

14. The method of claim 5, wherein the at least one affinity label comprises biotin.

15. The method of claim 5, wherein the method further comprises immobilizing the affinity label on a solid support.

16. The method of claim 7, wherein attaching the third DNA segment end to the fourth DNA segment end to form an attachment product comprises ligating the third DNA segment end to the fourth DNA segment end.

17. The method of claim 7, further comprising attaching at least one of the third DNA segment end and the fourth DNA segment end to at least one affinity label prior to sequencing.

18. The method of claim 7, comprising attaching at least one of the third DNA segment end and the fourth DNA segment end to a barcode.

* * * * *